US009291493B2

United States Patent
Angelsen et al.

(10) Patent No.: US 9,291,493 B2
(45) Date of Patent: Mar. 22, 2016

(54) NONLINEAR IMAGING WITH DUAL BAND PULSE COMPLEXES

(71) Applicant: SURF Technology AS, Trondheim (NO)

(72) Inventors: Bjørn A. J. Angelsen, Trondheim (NO); Thor Andreas Tangen, Trondheim (NO)

(73) Assignee: SURF Technology AS, Trondheim (NO)

( * ) Notice: Subject to any disclaimer, the term of this patent is extended or adjusted under 35 U.S.C. 154(b) by 478 days.

(21) Appl. No.: 13/573,697

(22) Filed: Oct. 3, 2012

(65) Prior Publication Data
US 2013/0279294 A1    Oct. 24, 2013

Related U.S. Application Data

(60) Provisional application No. 61/542,511, filed on Oct. 3, 2011.

(51) Int. Cl.
| | |
|---|---|
| A61B 8/00 | (2006.01) |
| G01S 7/52 | (2006.01) |
| G01H 9/00 | (2006.01) |
| A61B 8/14 | (2006.01) |
| A61B 5/05 | (2006.01) |
| A61B 8/08 | (2006.01) |

(52) U.S. Cl.
CPC ........ *G01H 9/008* (2013.01); *A61B 5/05* (2013.01); *A61B 8/14* (2013.01); *G01S 7/52022* (2013.01); *G01S 7/52042* (2013.01); *G01S 7/52077* (2013.01); *A61B 8/485* (2013.01); *G01S 7/52049* (2013.01)

(58) Field of Classification Search
USPC .......................................................... 367/7
See application file for complete search history.

(56) References Cited

U.S. PATENT DOCUMENTS

| | | | |
|---|---|---|---|
| 4,610,255 | A | 9/1986 | Shimura et al. |
| 4,844,082 | A | 7/1989 | Fukukita et al. |
| 4,936,308 | A | 6/1990 | Fukukita et al. |
| 6,186,951 | B1 | 2/2001 | Lizzi et al. |
| 6,312,383 | B1 | 11/2001 | Lizzi et al. |
| 6,461,303 | B2 * | 10/2002 | Angelsen ............... 600/458 |

(Continued)

FOREIGN PATENT DOCUMENTS

EP        0 279 314        8/1988

OTHER PUBLICATIONS

Fukukita et al. "Ultrasound pulse reflection mode measurement of nonlinearity parameter B/A and attenuation coefficient", vol. 99, No. 5, May 1996, pp. 2775-2782. (See Fig. 1).

*Primary Examiner* — James Hulka
(74) *Attorney, Agent, or Firm* — Cozen O'Connor

(57) ABSTRACT

The invention presents methods and instrumentation for measurement or imaging of a region of an object with waves of a general nature, for example electromagnetic (EM) and elastic (EL) waves, where the material parameters for wave propagation and scattering in the object depend on the wave field strength. The invention specially addresses suppression of $3^{rd}$ order multiple scattering noise, referred to as pulse reverberation noise, and also suppression of linear scattering components to enhanced signal components from nonlinear scattering. The pulse reverberation noise is divided into three classes where the invention specially addresses Class I and Class II $3^{rd}$ order multiple scattering that are generated from the same three scatterers, but in opposite sequence.

44 Claims, 8 Drawing Sheets

(56) References Cited

U.S. PATENT DOCUMENTS

Figure 1A:
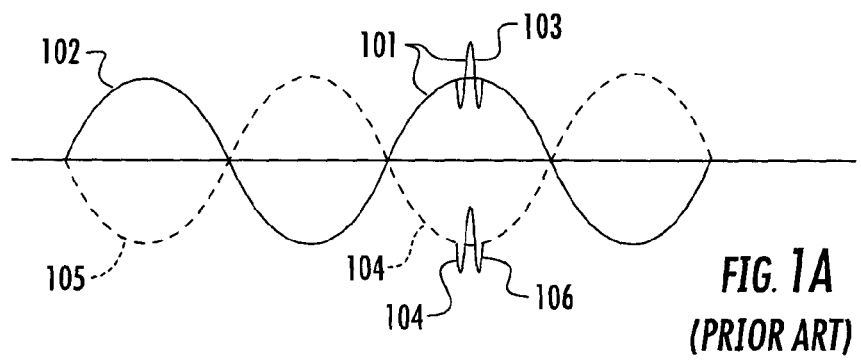

| | | | |
|---|---|---|---|
| 7,641,613 B2* | 1/2010 | Angelsen et al. | 600/458 |
| 7,727,156 B2* | 6/2010 | Angelsen et al. | 600/459 |
| 8,037,582 B2* | 10/2011 | Okada et al. | 24/297 |
| 8,038,616 B2* | 10/2011 | Angelsen et al. | 600/437 |
| 8,182,428 B2* | 5/2012 | Angelsen et al. | 600/459 |
| 8,550,998 B2* | 10/2013 | Angelsen et al. | 600/437 |
| 8,793,079 B2* | 7/2014 | Angelsen et al. | 702/33 |
| 2004/0267129 A1* | 12/2004 | Angelsen et al. | 600/458 |
| 2004/0267130 A1* | 12/2004 | Angelsen et al. | 600/458 |
| 2005/0203416 A1* | 9/2005 | Angelsen et al. | 600/463 |
| 2005/0277835 A1* | 12/2005 | Angelsen et al. | 600/437 |
| 2006/0052699 A1* | 3/2006 | Angelsen et al. | 600/437 |
| 2007/0035204 A1* | 2/2007 | Angelsen et al. | 310/311 |
| 2009/0000085 A1* | 1/2009 | Okada et al. | 24/453 |
| 2009/0178483 A1* | 7/2009 | Angelsen et al. | 73/597 |
| 2009/0182237 A1* | 7/2009 | Angelsen et al. | 600/459 |
| 2010/0036244 A1* | 2/2010 | Angelsen et al. | 600/438 |
| 2012/0095699 A1* | 4/2012 | Angelsen et al. | 702/33 |
| 2012/0269385 A1* | 10/2012 | Lee et al. | 382/103 |

* cited by examiner

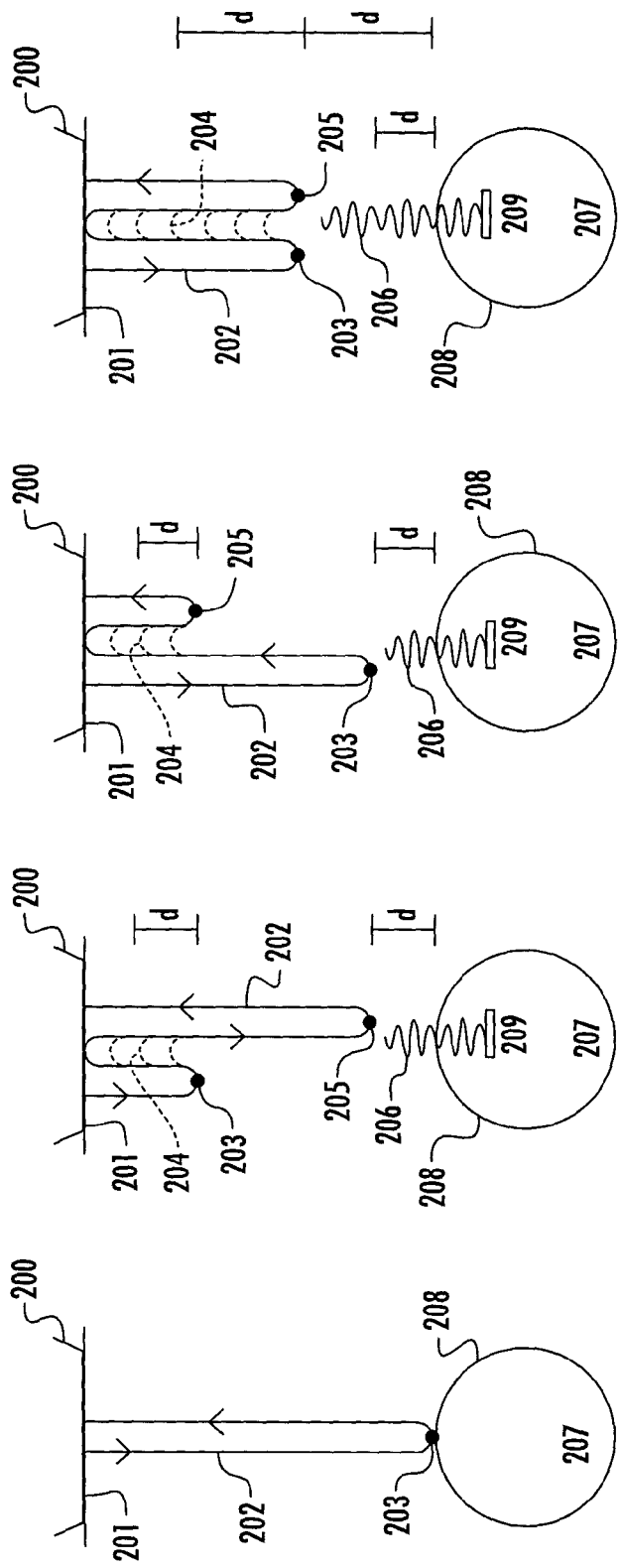

NONLINEAR IMAGING WITH DUAL BAND PULSE COMPLEXES

CROSS-REFERENCE TO RELATED APPLICATION

The application claims priority from U.S. Provisional Patent Application Ser. No. 61/542,511, filed Oct. 3, 2011, the contents of which are incorporated by reference herein.

1. FIELD OF THE INVENTION

The present invention is directed towards real time ultrasound imaging of the heart and visualization and analysis of the images for detection of regional deficiencies in myocardial (MC) contraction and relaxation function.

2. BACKGROUND OF THE INVENTION

Material properties that determine electromagnetic (EM) or elastic (EL) wave propagation and scattering in the materials often show a variation with the field strength in the waves. Such materials are termed non-linear and give rise to nonlinear wave propagation and nonlinear scattering of both EM and EL waves. Measurements or imaging of nonlinear scattering sources are in many situations useful to identify properties of such materials.

Both the forward wave propagation and local scattering of EM or EL waves have mathematical similarities, and methods and instrumentation for imaging therefore have similar structures. Examples of uses of EL waves are material testing both with shear waves and compression waves, ultrasound medical imaging with compression waves, SONAR sub-sea and geological measurements, and seismic imaging. EM waves have similar uses, where particularly new developments of EM technology appear useful for both geological and medical imaging, providing added information to elastic wave images. EM imaging in the infra-red and optical frequency ranges also provides useful information both for material testing and medical imaging.

The nonlinear scattering can for EM or EL waves be separated into a parametric and a resonant scattering type. For EL waves, the parametric scattering originates from a nonlinear variation of the local elasticity parameters with the amplitude of the local elastic wave field, where spatial variations of the nonlinear variation produce the nonlinear scattering. For EM waves, the parametric scattering originates from a nonlinear variation of the local dielectric constant or magnetic permeability with the amplitude of the local EM wave field, where spatial variations of the nonlinear variation produce the nonlinear scattering. With elastic compression waves, referred to as acoustic waves, one for example gets strong nonlinear parametric scattering at the interface between soft materials and hard materials, for example as found with ultrasound nonlinear scattering from micro calcifications in soft tissue or acoustic scattering from hard objects in soil like mines or other objects. One also gets strong nonlinear scattering at the interface between harder materials and much softer materials, for example as found with ultrasound scattering from gas micro-bubbles in blood or gas filled swim-bladders of fish and the like in water.

Resonant nonlinear scattering has a time lag involved, which in some situations can be used to separate signal components from local nonlinear scattering and forward propagation distortion of the incident waves. However, the current invention provides further advantages for imaging of local resonant nonlinear scattering sources.

For acoustic waves, gas micro-bubbles show resonant scattering, for example, where the resonance originates from the energy exchange between the nonlinear elasticity of the bubble with shell and gas, and a co-oscillating fluid mass around the bubble with a volume approximately 3 times the bubble volume. As both the elasticity and the mass vary with bubble compression, the resonance frequency is nonlinearly affected by the incident acoustic wave field, producing a particularly strong nonlinear scattering with a large amount of harmonic components of the incident frequency (n-times the incident frequency) and even sub-harmonic components of the incident frequency (a fraction of the incident frequency) in the scattered field, and supra-harmonic components (bands around the harmonic components) of the incident frequency. However, for imaging at frequencies well above the bubble resonance frequency, the nonlinear scattering is much lower, and the present invention provides solutions for enhanced imaging of micro-bubbles at frequencies above the resonance frequency.

Resonant nonlinear EM scattering originates in the interaction between the wavefield and the atoms and molecules, which is best described within the realm of quantum physics. An example of EM resonant scattering is fluorescence which has similarities to sub-harmonic acoustic scattering. When for example the incident frequency is in the ultraviolet range, the scattered frequency can be in the visible range. The scattered frequency can also be the same as the incident frequency which is termed "resonant fluorescence". Another example is two-photon quantum scattering that is similar to $2^{nd}$ harmonic parametric scattering, but includes detailed atomic dynamics with time lags in the process.

There is also found a nonlinear interaction between EM and EL waves in materials, where for example EL compression waves change the EM material parameters in the process called the acousto-optic effect. Absorption of EM waves in materials produces a rapid, local heating of the material that generates acoustic waves in a process called the photo-acoustic effect. The invention hence addresses both EM and EL waves, and combinations of these, where the waves referred to in the description and claims can be both EM and/or EL waves.

With a single frequency band incident wave, the parametric nonlinear scattering produces harmonic components of the incident frequency band in the scattered wave. With dual band incident waves that interact locally, the parametric nonlinear scattering produces bands around convolutions of the incident frequency bands, resulting in bands around sums and differences of the incident frequencies. However, the nonlinear variation of the material parameters also produces an accumulative nonlinear distortion of the forward propagating wave. When the pulse length of the high frequency pulse increases above approximately a period of the low frequency pulse, the linear scattering from the nonlinear forward propagation distortion has a similar signature to the local nonlinear scattering, and it is in this case difficult to distinguish the signal components that arises from linear scattering of the nonlinear propagation distortion of the incident wave, and the signal components that occur from local nonlinear scattering. This is for example the situation with current harmonic imaging with medical ultrasound imaging.

On the contrary, when the pulse length of the high frequency pulse becomes shorter than approximately a half period of the low frequency pulse, it is possible to highly suppress the linear scattering components to measure or image the nonlinear scattering components, for example as shown in U.S. Pat. No. 8,038,616 and U.S. patent application Ser. Nos. 12/351,766, 12/500,518, and 13/213,965. Multiple scattering of EL and EM waves from strong scatterers often produce strongly disturbing noise in the measurements and images. When the pulse length of the high frequency pulse becomes shorter than half the wave length of the low frequency pulse, it is possible to highly suppress this multiple scattering noise, where some methods are presented in the cited US Patent applications. Based on this background, the object of the current invention is to present improved methods and instrumentation for measurement and imaging of nonlinear scattering components and suppression of the multiple scattering noise, both with elastic and electromagnetic waves.

3. SUMMARY OF THE INVENTION

An overview of the invention is presented. The overview is meant for illustration purposes only, and by no means represents limitations of the invention, which in its broadest aspect is defined by the claims appended hereto.

The invention presents methods and instrumentation for measurement or imaging of a region of an object with waves of a general nature, for example electromagnetic (EM) or elastic (EL) waves, where the material parameters for wave propagation and scattering in the object depend on the wave field strength. Such materials are termed non-linear, and wave propagation in such materials defines the concepts of nonlinear wave propagation and scattering. The invention specially addresses strong suppression of $3^{rd}$ order multiple scattering noise, referred to as pulse reverberation noise, and also suppression of linear scattering components to enhance signal components from nonlinear scattering. The pulse reverberation noise is divided into three classes where the invention specially addresses Class I and II $3^{rd}$ order multiple scattering that are generated from the same three scatterers, but in opposite sequence. One specially addresses methods to achieve close to similar Class I and II pulse reverberation noise in the measurements, which simplifies the suppression of both classes combined, and methods for combined suppression of Class I and II noise that compensate for a difference in Class I and II noise in the measurements.

The methods are based on transmission of dual band pulse complexes composed of a low frequency (LF) pulse and a high frequency (HF) pulse, where the LF pulse is used to nonlinearly manipulate the object material parameters observed by the co-propagating HF pulse. One or both of scattered and transmitted components from the HF pulse are picked up and gives HF receive signals that are further processed to suppress pulse reverberation noise and enhance nonlinear scattering components.

One typically wants the HF pulse to propagate along the crest or trough of the co-propagating LF pulse. The nonlinear manipulation of the object properties by the LF pulse produces a change in the wave propagation velocity for the co-propagating HF pulse. This change in propagation velocity introduces a nonlinear propagation delay given by the LF field strength and polarity at the center of the HF pulse, where said nonlinear propagation delay accumulates with propagation distance. For a given polarity of the LF pulse one can get a negative nonlinear propagation delay, which represents propagation advancement. We shall however use the generalized concept of delay, which can be both positive and negative. A variation of the LF field strength along the co-propagating HF pulse produces a nonlinear pulse form distortion of the HF pulse that also accumulates with propagation distance. Spatial variations of the nonlinear object parameters, produces a scattering of the HF pulse that depends on the local value of the co-propagating LF pulse.

In addition to the nonlinear manipulation by the LF pulse of the propagation velocity and scattering of the co-propagating HF pulse, the nonlinearity of the object parameters introduces a self-distortion of the HF pulse by its own field strength. This self-distortion of the HF pulse introduces harmonic bands in the HF pulse around harmonic components of the fundamental, transmitted HF band, and is the basis for current methods of harmonic imaging. The transfer of energy into harmonic bands are observed as a nonlinear attenuation of the fundamental HF band that is compensated for in the model based methods of estimation of noise suppression according to the invention.

At the first scattering of the pulse complex, the amplitude of the both the LF and HF pulses generally drops so much that the nonlinear effect on HF pulse propagation and scattering can be neglected after this first scattering. This opens for the use of the methods to suppress multiple scattering noise in the HF receive signal, as the nonlinear effects on $1^{st}$ order and multiple order scattering of the waves at the same propagation lag are different.

To observe multiple scattering noise, the first scatterer must be inside the transmit beam and the last scatterer must be inside the receive beam. With single, fairly narrow transmit beams, this implies that we with back-scattering measurements mainly observe odd order scattering. As the pulse amplitude drops for each scattering, we mainly observe $3^{rd}$ order multiple scattering noise (i.e. three scatterers), where the $1^{st}$ scatterer is inside the transmit beam, and the $3^{rd}$ scatterer is inside the receive beam. With multiple transmits of very wide transmit beams where the receive signals are reconstructed for narrow, synthetic transmit beams, the situation is the same. However, with very wide transmit beams, or parallel transmit beams, overlapped with multiple parallel, highly focused receive beams, it is in principle possible to observe $2^{nd}$ order multiple scattering, where the $1^{st}$ scatterer is inside a transmit beam at a distance from the $2^{nd}$ scatterer inside a highly focused receive beam. However, the main disturbing multiple scattering noise originates from fatty layers inside muscle or parenchyma tissue, where the transmit and receive beams have close to normal incidence to the layers. Such anatomy makes such $2^{nd}$ order scattering low. Ribs or other similar structures can however have spatial relations to the beams that make $2^{nd}$ order scattering noise visible in special situations.

With a sequence of $3^{rd}$ order scatterers at positions $\underline{r}_1 => \underline{r}_2 => \underline{r}_3$, where $\underline{r}_1$ is inside the transmit beam and $\underline{r}_3$ is inside the receive beam, we will also have $3^{rd}$ order scattering from the same scatterers in the opposite sequence, i.e. $\underline{r}_3 => \underline{r}_2 => \underline{r}_1$, where $\underline{r}_3$ is inside the transmit beam and $\underline{r}_1$ is inside the receive beam. We therefore divide the $3^{rd}$ order scattering noise into three classes, where for Class I the sequence of scatterers is $\underline{r}_1 => \underline{r}_2 => \underline{r}_3$ where for the $1^{st}$ scatterer $r_1 < r/2$ for $r = ct/2$ as the depth of the image point with t being the time of signal arrival (fast time) and c is the wave propagation velocity. For the Class I noise to occur at $r = ct/2$ we have for the $3^{rd}$ scatterer that $r_3 > r/2$. For Class II noise the situation is opposite where for the $1^{st}$ scatterer $r_3 > r/2$ and for the $3^{rd}$ scatterer $r_1 < r/2$. For Class III noise, both the $1^{st}$ and $3^{rd}$ scatterers are close to r, i.e. deeper than r/2. Class III noise can with the model based estimation of noise suppression be suppressed in combination with Class I and Class II noise. However Class III noise is in many situations weaker than the combined Class I and II noise.

At a defined fast time arrival of echoes, t, the HF receive signal is composed of several overlapping pulses, both from $1^{st}$ and $3^{rd}$ order scattered components of the transmitted HF pulses. These several overlapping pulses will interfere both constructively and destructively depending on the detailed arrival time of the pulses, and this interference hence produces a depth variation in the envelope of the HF receive signal that is typical for coherent imaging systems, and which we refer to as speckle. The LF pulse will generally introduce both a nonlinear propagation delay/advancement of the HF receive signal, and also an LF pulse dependent variation in the HF receive signal speckle.

A central part of the methods according to the invention is hence processing of said HF receive signal to form measurement or image signals wherein said processing comprises correcting at least one of said HF receive signals by at least one of
  i) delay corrections using correction delays in a fast time (depth-time), and
  ii) speckle corrections using speckle corrections in the fast time, to form corrected HF signals, and
further processing said corrected HF signals to form at least one of a noise suppressed HF signal with suppression of pulse reverberation noise and a nonlinear scattering signal with suppression of linear scattering components.

For HF receive signals where the bandwidth is wide compared to the frequency of the LF pulse, the main effect of the pulse form distortion in the HF receive signal is found at the edges of the HF receive band. One gets interesting correction for the pulse form distortion by reducing the bandwidth of the HF receive signal through band pass filtering.

For the $1^{st}$ order scattered signal, the nonlinear propagation delay is given by the accumulated change in propagation velocity by the LF pulse at the site of the co-propagating HF pulse up to the image depth $r=ct/2$. For the combined Class I and II pulse reverberation noise, the nonlinear noise delay is given by an average of the nonlinear noise delay for Class I and Class II, which both are averages of the nonlinear propagation delays for the distribution of $1^{st}$ scatterers that contribute to the Class I and II noise at $r=ct/2$. The relationship between the LF pulse and the combined Class I and II nonlinear noise delay is hence more complex than for $1^{st}$ order scattering. However, for HF transmit and receive beams that are close to equal and a linear variation of the nonlinear propagation delay $t(t)$ with fast time arrival $t$ of the HF receive signal, the noise correction delay can be approximated to $t(t)/2$.

The dependency of the $1^{st}$ order scattered signal speckle on the LF pulse is mainly given by the pulse form distortion of the transmitted HF pulse by the co-propagating LF pulse that produces the $1^{st}$ order scattered signal at fast time $t$. The phase of a focused LF pulse will slide 90 deg from the near field to the diffraction limited focal region, and the co-propagating HF pulse will then at certain depth ranges observe a non-negligible gradient of the LF field along the HF pulse, producing a HF pulse compression/expansion depending on the LF field gradient and its polarity along the HF pulse. With wide LF transmit beams where diffraction plays a negligible role, one can position the HF pulse at the crest or trough of the co-propagating LF pulse for the whole measurement or image depth, reducing the pulse form distortion of the HF pulse by the LF pulse. However, if the HF pulse has a non-negligible pulse length compared to the LF pulse oscillation period, one will in this case get a non-negligible HF pulse form distortion of the HF pulse up to the first scattering.

A variation of the nonlinear propagation delay for the $1^{st}$ order scattered pulses that overlap at a fast time $t$ of the HF receive signal, will also produce a LF pulse dependent speckle of the HF receive signal from $1^{st}$ order scattered components. A main reason for such a variation is that the HF receive beam is so weakly focused that the nonlinear propagation delay varies across the receive beam. A remedy to reduce this effect is stronger HF receive beam focusing with lower F-number. However, this can introduce a difference between the HF transmit and receive beams that complicates the estimation of the combined Class I and II nonlinear noise delay. Several solutions to these problems is given in this invention, such as the use of multiple transmit foci, or transmit of broad LF and HF transmit beams in different directions with synthetic transmit focusing in a large group of image points, or using model based estimation of the corrections for both $1^{st}$ order nonlinear signal delay and speckle. The effect on signal speckle from variations of the nonlinear propagation delay along the beam axis, is reduced by using short HF pulses.

The dependency of the combined Class I and Class II noise speckle on the LF pulse is as for the nonlinear noise delay more complex than for the $1^{st}$ order scattering components. The reason for this is that a large number of combined Class I and II noise pulses with a wide distribution of positions of $1^{st}$ scatterers can overlap at the same fast time point $t=2r/c$ of the HF receive signal. The pulses with different $1^{st}$ scatterers have different nonlinear propagation delays and pulse form distortion due to different accumulative propagation lengths to the $1^{st}$ scatterer along different propagation paths, and hence have different variations with the field strength and polarity of the LF pulse, making the interference and noise speckle much more sensitive to variations in the LF pulse compared to for the $1^{st}$ order scattered components in the HF receive signal at a defined fast time $t$. A special situation is found when the HF transmit and receive beams are equal, with negligible pulse form distortion of the transmitted HF pulse, and linear variation with fast time $t$ of the nonlinear propagation delay, where the combined Class I and II noise speckle is independent on the polarity of the LF pulse, that is useful for suppression of the combined Class I and II pulse reverberation noise. In other situations we show how to obtain corrections for both nonlinear noise delay and noise speckle of combined Class I and II pulse reverberation noise through model based estimation.

In a first embodiment according to the invention the HF receive and transmit apertures and HF receive and transmit foci are selected so that a difference between Class I and II pulse reverberation noise in the HF receive signal is substantially minimized. In a further specialized embodiment of this method, the HF transmit and receive apertures and foci are set equal. To obtain adequate beam focusing over a depth range, the invention devices to transmit multiple groups of pulse complexes along each image line with different HF transmit and receive focal depths for each group of pulse complexes, to obtain focus at more than one depth range in the image. The invention also devices to use transversal filtering of the HF receive signal for multiple, neighboring image lines to obtain a depth variable focusing of the combined HF transmit and receive beams with fixed focus. The invention alternatively proposes to transmit multiple pulse complexes with wide transmit beams with different directions, and receive and store all HF receive element signals from a HF receiver array, and carry through synthetic image reconstruction for a large group of image points providing synthetic HF transmit and receive beams that for the image points of said group can be selected to provide substantially similar Class I and II pulse reverberation noise, that greatly simplifies the processing for combined suppression of Class I and II pulse reverberation noise in said group of image points. Substantially similar Class I and II pulse reverberation noise can in many situations be obtained in an image point by choosing the synthetic transmit and receive beams to be equal in said image point. With this method it is desirable, but not necessary, to use transmit wave fronts that are close to plane, at least in one direction, often referred to as plane wave imaging. With little difference between the Class I and II pulse reverberation noise in the HF receive signal, it is an advantage to select the LF and HF transmit apertures so that the nonlinear propagation delay t(t) for the transmitted HF pulse has a substantially linear variation with the fast time t, and for combined suppression of Class I and II pulse reverberation noise, said correction delays are set equal to t(t)/2.

In a further modification of the methods, one do not search to minimize a difference between Class I and II pulse reverberation noise in the HF receive signal, where instead at least one of said correction delays and said speckle corrections are estimated to compensate for a difference between Class I and II noise in said HF receive signal.

In the estimation of correction delays and speckle corrections one frequently makes use of simulation of the nonlinear wave propagation in the object utilizing defined material parameters. Said defined material parameters can be adjusted for suppression in a processed HF receive signal of at least one of i) pulse reverberation noise, and ii) $1^{st}$ order linear scattering components to provide nonlinear scattering components, through one or both of a) manual adjustment of said object material parameters based on observations in a displayed image, and
b) computer based adjustment of said object material parameters to minimize the total power in said processed HF receive signal in a region of an image.

For advanced suppression of combined Class I and II noise with differences between the Class I and II noise in the HF receive signal, the invention devices:

obtaining the nonlinear propagation delay and pulse form distortions for the transmitted HF pulses as a function of position of the $1^{st}$ scatterers through simulations of a nonlinear wave equation for the actual LF/HF pulse complexes with defined parameters, and obtaining estimates of parameters relating to relative reflection coefficients of strong reflectors as a function of depth along the beam from the measured HF receive signal, and obtaining estimates of noise correction delays and speckle corrections in a process that includes combining in a mathematical model for pulse reverberation noise, said nonlinear propagation delays and pulse form distortions up to the $1^{st}$ scatterer obtained through simulations, and said estimates of parameters relating to relative reflection coefficients obtained from the measured HF receive signal. Said method can also be extended to suppress Class I/II/III pulse reverberation noise combined.

In this situation one would typically carry through the process in steps where each step applies the method as in the previous paragraph, and for each step said defined parameters are adjusted to increase suppression of pulse reverberation noise, where said adjustment is carried through as one or both of a) manual adjustment based on observation of a displayed image, and
b) automatic adjustment to minimize the total power in a processed HF receive signal in a region of an image.

The invention further devices to carry through said simulations of a nonlinear wave equation for different sets of parameters before the measurements, and electronically store the results of said simulations for said set of parameters, and in the estimation process the simulations for defined parameters is retrieved from memory based on a memory address related to said defined parameters.

The invention further devices to obtain and store from simulations of a nonlinear wave equation for a typical set of material parameters, both the nonlinear propagation delay and pulse form distortion and also gradients of these so that nonlinear propagation delay and pulse form distortions for different material parameters can be obtained through a Taylor or Fourier series representation of these as a function of variations in the material parameters.

For combined suppression of Class I and II pulse reverberation noise in echo weak regions, the same HF receive signal obtained with a non-zero LF pulse is delay corrected with two different correction delays to provide two corrected HF signals, and said two corrected HF signals are combined to provide a noise suppressed HF signal. This method reduces the need for speckle corrections.

The methods further comprises combined suppression of pulse reverberation noise and enhancement of nonlinear scattering components, wherein said step of transmitting includes transmitting at least 3 pulse complexes with different LF pulses, and wherein said step of correcting includes correcting and combining the HF receive signals to form at least two noise suppressed HF signals, and said at least the two noise suppressed HF signals are further processed by at least one of
  i) delay corrections using correction delays in a fast time (depth-time), and
  ii) speckle corrections using speckle corrections in the fast time,
to form at least two corrected intermediate HF signals, and said corrected intermediate HF signals are combined to suppress linear scattering components to form nonlinear measurement or imaging HF signals.

The invention further defines instruments for carrying through the methods of the invention, where said instruments comprises transmit means comprising a low frequency (LF) transmit aperture and a high frequency (HF) transmit aperture for transmitting at least two pulse wave complexes towards said region, each of said pulse complexes being composed of an LF pulse with frequencies in an LF band transmitted from the LF aperture and an HF pulse with frequencies in an HF band transmitted from the HF aperture, the HF pulse propagating spatially so close to the LF pulse that the HF pulse observes a manipulation of the object material parameters by the co-propagating LF pulse at least for a part of a propagation depth of the HF pulse, and at least the transmitted LF pulse varies for each transmitted pulse complex to produce different manipulations of the object, and receive and beam forming means comprising a HF receive aperture that picks up HF receive signals from one or both of scattered and transmitted HF components from the at least two transmitted pulse complexes, and correction means for processing said HF receive signal to form measurement or image signals wherein said processing comprises correcting at least one of said received HF signals by at least one of
  i) delay corrections using correction delays in a fast time (depth-time), and
  ii) speckle corrections using speckle corrections in the fast time,
to form corrected HF signals, and means for further processing said corrected HF signals to form at least one of a noise suppressed HF signal with suppression of pulse reverberation noise and a nonlinear scattering signal with suppression of linear scattering components.

Embodiments of the instrument comprises means for selecting HF transmit and receive apertures and HF transmit and receive foci to minimize a difference between Class I and II pulse reverberation noise in the HF receive signal. To obtain good focusing in a depth range, embodiments of the instrument can comprise means for transmitting multiple pulse complexes with different HF focal depths along each image line, and means for selecting HF receive apertures and foci for each transmit pulse focus to minimize a difference between Class I and II pulse reverberation noise. In many situations it is satisfactory to choose equal HF transmit and receive apertures and HF transmit and receive foci.

Embodiments of the instrument further comprises means for transmitting more than one pulse complex with wide beams and different directions towards said object, and said receive means comprises a HF receive aperture comprising an array of more than one HF receive element that allows receiving and storing HF receive element signals for each HF receive element and each transmitted pulse complex, and means for image reconstruction for a large group of image points that comprises means for combining said HF receive element signals from said transmitted pulse complexes for each image point of said group to provide synthetic HF transmit and receive beams so that a difference between Class I and II pulse reverberation noise is substantially minimized in the reconstructed HF receive signal for said group of image points. This can in many situations be obtained by choosing the image reconstruction for an image point so that the synthetic HF transmit and receive beams become substantially equal. In one embodiment said transmit means allows transmit of LF and HF pulse waves with wave fronts that are substantially plane in at least one direction.

The instrument further comprises estimation means for estimation of at least one of said correction delays and speckle corrections either according to known methods, or new methods according to this invention where said means for estimation of said correction delays and said speckle corrections are designed to compensate for a difference in Class I and II pulse reverberation noise in said HF receive signal, for combined suppression of Class I and II pulse reverberation noise. Said estimation methods can be further extended to also suppress Class I/II/III pulse reverberation noise combined.

In further embodiments of the invention said transmit means allow the LF and HF transmit apertures to be selected so that the nonlinear propagation delay t(t) for the transmitted HF pulse has a substantially linear variation with the fast time $t=2r/c$. When the HF transmit and receive apertures and foci, both real and synthetic, are selected so that a difference between the Class I and II noise is minimized, said correction delays for suppression of pulse reverberation noise at fast time t can be set close to $t(t)/2$.

In further embodiments according to the invention said estimation means comprises means for simulations of nonlinear wave propagation in the object utilizing defined material parameters, where said nonlinear propagation delays and pulse form distortions up to the $1^{st}$ scatterer are obtained from the simulated HF pulse wave. Said means for simulation can comprise means for storage of a set of simulations with different defined parameters where said set of simulations are carried through before the measurements, and in the estimation process the simulation for defined parameters is retrieved from memory based on a memory address related to said defined parameters.

Said means for simulation can also comprise means for storage of the nonlinear propagation delay and pulse form distortion and gradients of the same, simulated for a given set of material parameters, so that the estimates of the nonlinear propagation delay and pulse form distortion for other material parameters can be obtained through a Taylor series representation of their variation with the material parameters.

Said estimation means further can comprise means for adjusting said defined parameters to increase the suppression of one or both of i) pulse reverberation noise and ii) $1^{st}$ order linear scattering components in a processed HF receive signal, where said adjusting is carried through as one or both of
 a) manual adjusting based on observation of a displayed image, and
 b) automatic adjusting to minimize the total power in the processed HF receive signal in a region of an image.

In a particular model based estimation for suppression of pulse reverberation noise, said means for simulation provides estimates of at least one of the nonlinear propagation delays and pulse form distortions of the propagating HF pulses up to the $1^{st}$ scatterer, and said means for estimation further comprises means for obtaining estimates of parameters relating to the relative reflection coefficients of strong reflectors as a function of depth along the beam from the measured HF receive signal, and means for obtaining estimates of noise correction delays and speckle corrections in a process that includes combining in a mathematical model for pulse reverberation noise, said nonlinear propagation delays and pulse form distortions obtained through simulations, and said estimates of parameters relating to relative reflection coefficients obtained from the measured HF receive signal.

To provide combined suppression of pulse reverberation noise and enhancement of nonlinear scattering components in the HF receive signal, said transmit means comprises means for transmitting at least 3 pulse complexes with different LF pulses towards the object, and said correction means comprises correcting and combining the HF receive signals to form at least two noise suppressed HF signals, and means for further processing of said at least two noise suppressed HF signals including at least one of
 i) delay corrections using correction delays in a fast time (depth-time), and
 ii) speckle corrections using speckle corrections in the fast time,
to form at least two corrected intermediate HF signals, and means for combining said corrected intermediate HF signals to suppress linear scattering components to enhance nonlinear scattering components in the HF receive signals.

4. SUMMARY OF THE DRAWINGS

Figure 3:
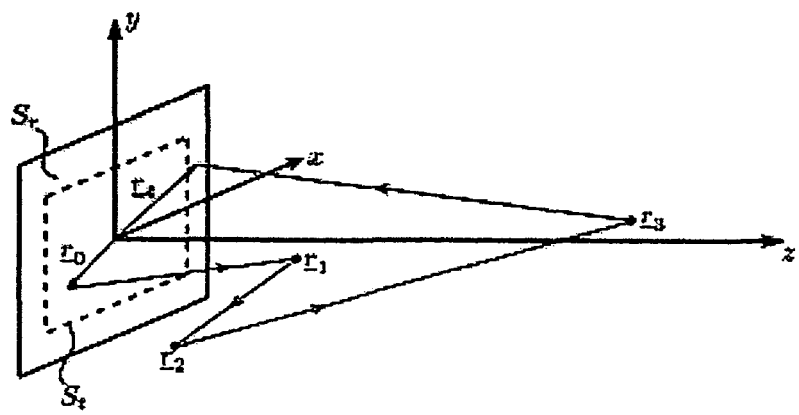
Figure 4:
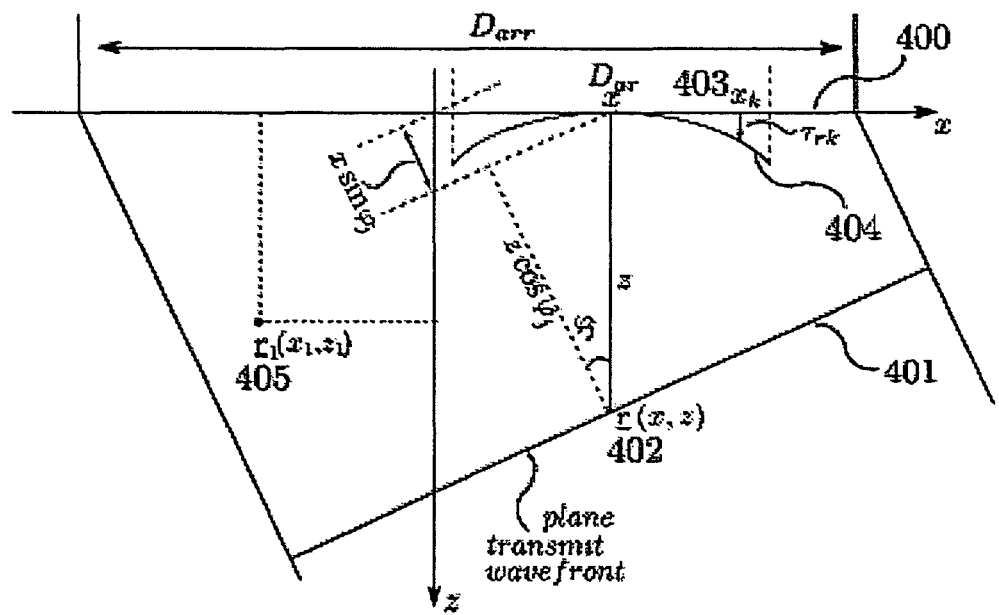
Figure 5:
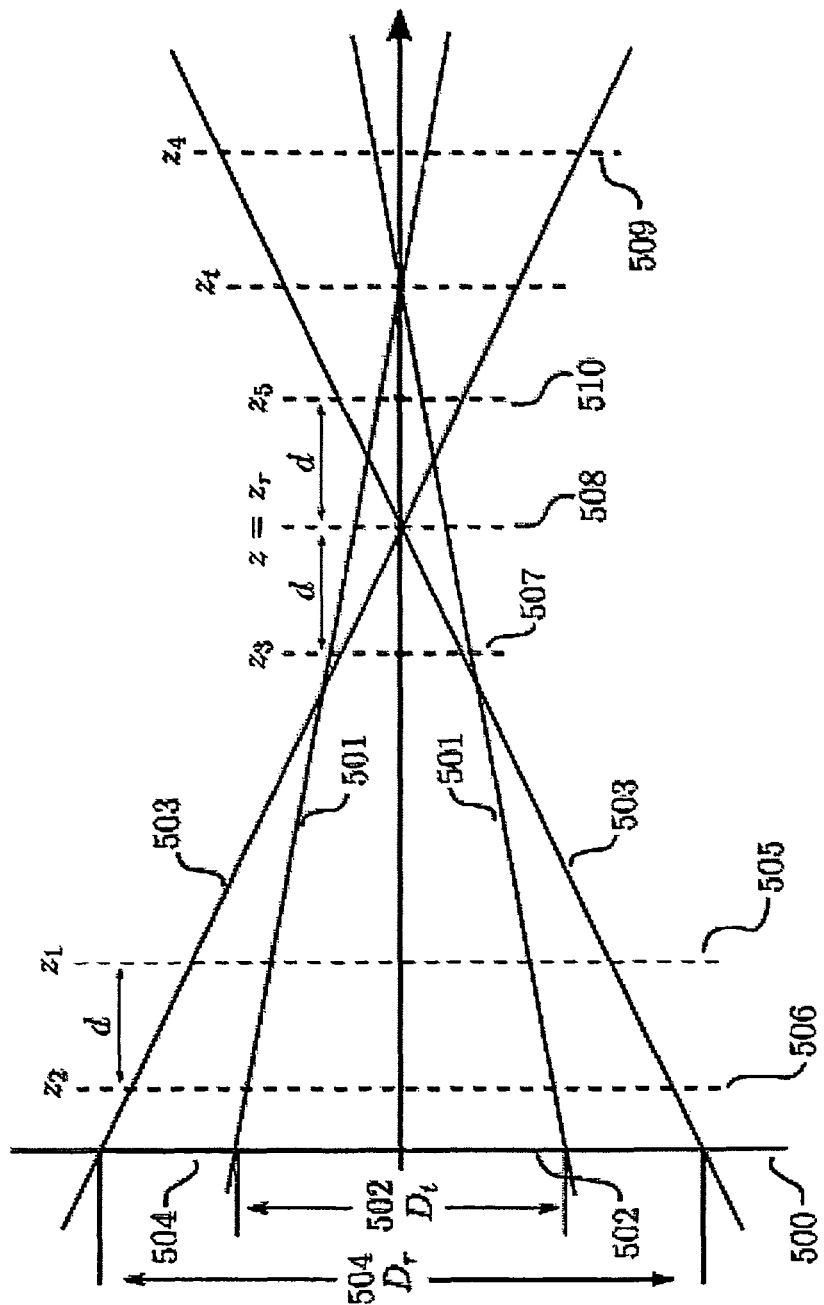
Figure 6:
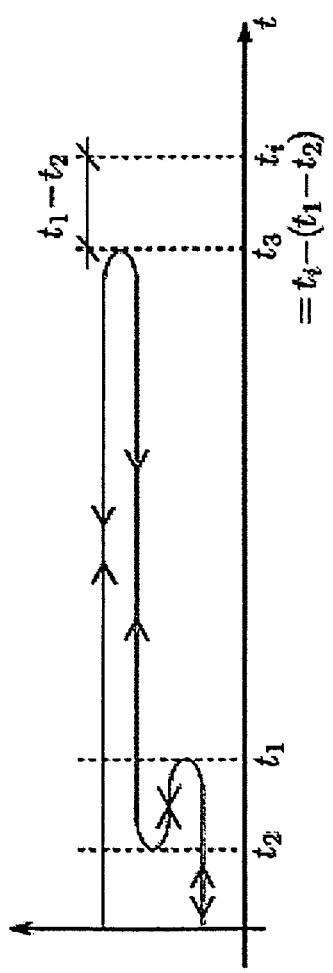
Figure 7A:
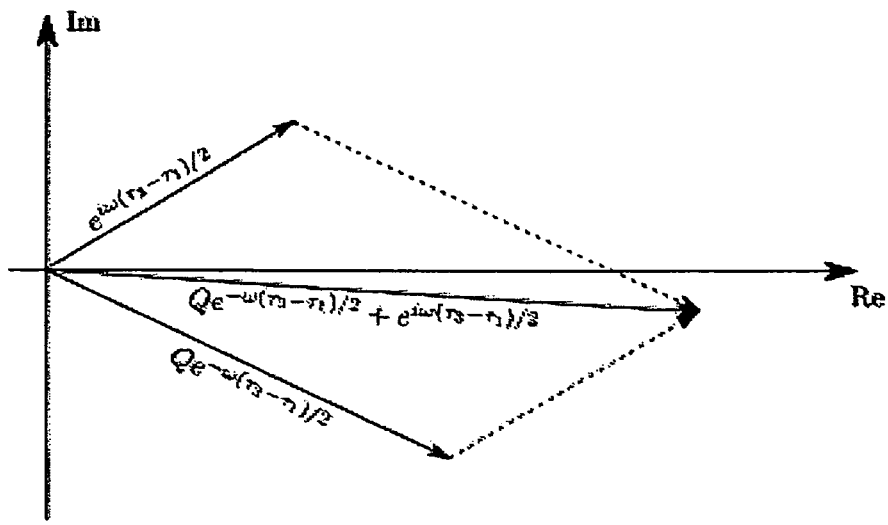
Figure 7B:
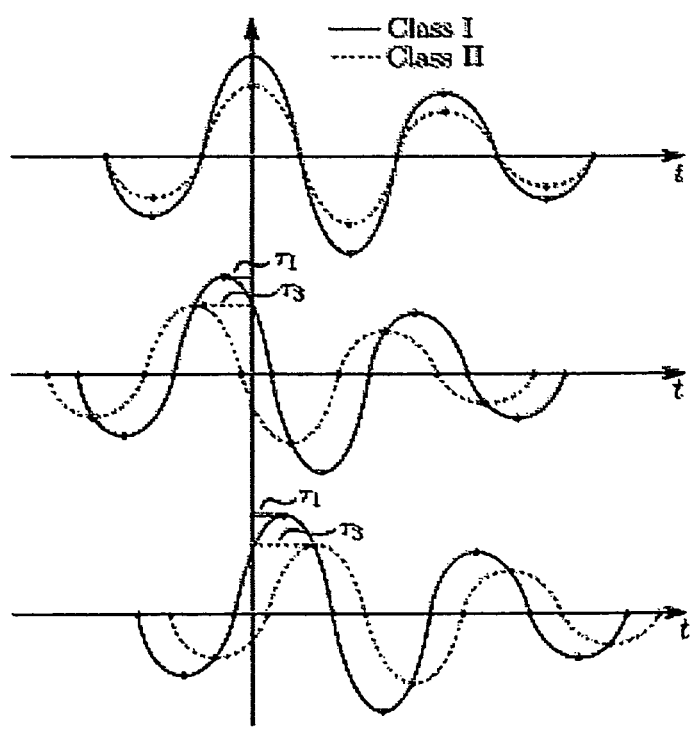
Figure 8:
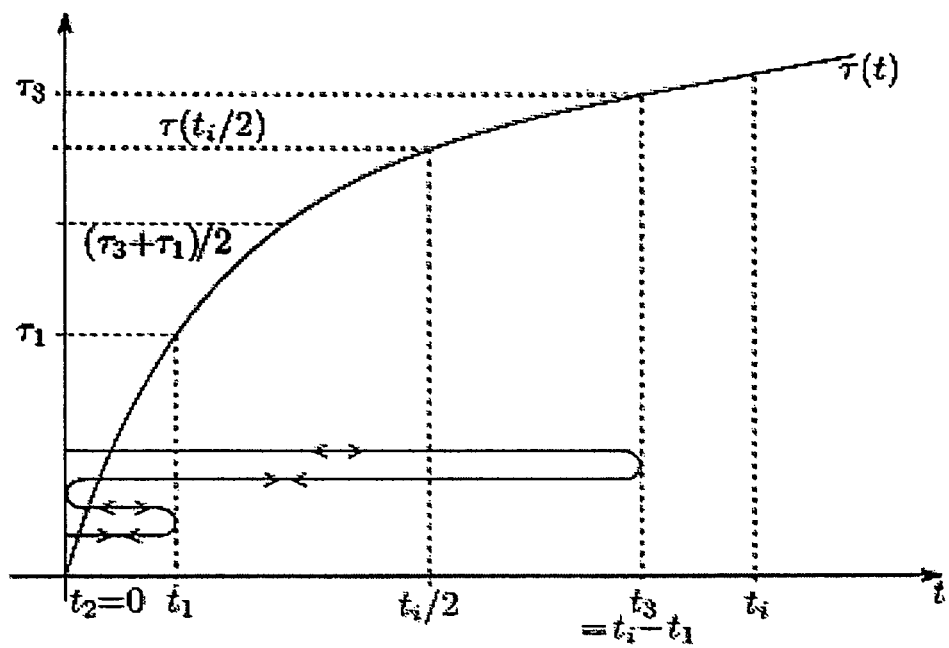
Figure 9:
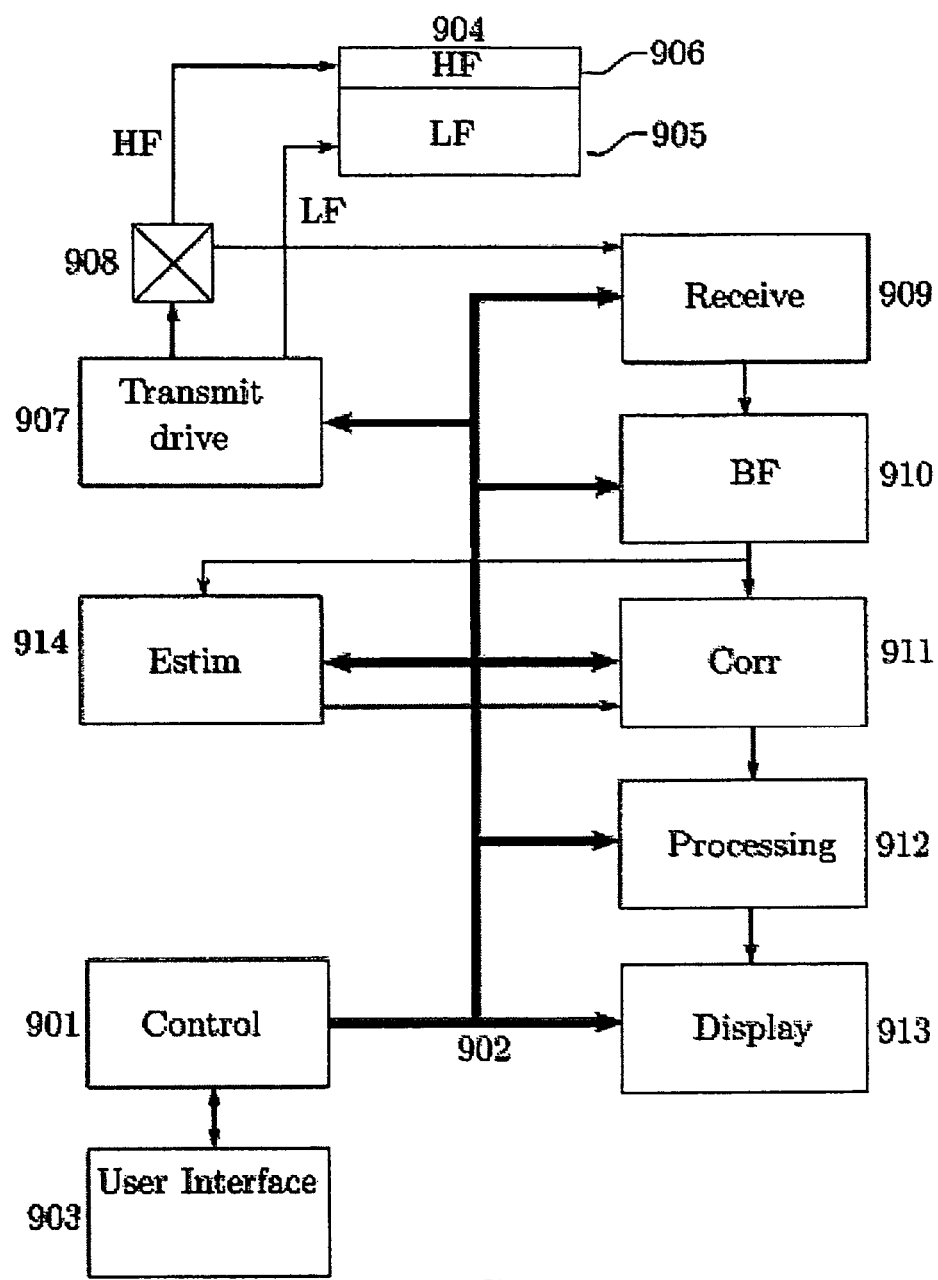

FIG. 1 Shows Prior Art dual band pulse complexes for suppression of multiple scattering noise and/or $1^{st}$ order scattering to show nonlinear scattering with pulse wave measurements or imaging, and FIG. 2 Shows a classification of different types of multiple scattering noise that is found in a typical ultrasound image of an organ, and FIG. 3 Illustrates coordinates and volumes for calculating the received $1^{st}$ and $3^{rd}$ order scattered signals, and FIG. 4 Shows and illustration of image reconstruction from multi component transmit of broad beams, and FIG. 5 Shows example plane reflectors that generate strong $3^{rd}$ order pulse reverberation noise, and FIG. 6 Shows coordinates for $1^{st}$ to $3^{rd}$ reflectors in the fast time domain, and FIG. 7 Shows interference between Class I and II pulse reverberation noise when Q>1, and FIG. 8 Shows illustration of the effect on noise correction delay for nonlinear variation with fast time of the nonlinear propagation delay, and FIG. 9 Shows a block diagram of an instrument according to the invention.

5. DETAILED DESCRIPTION OF THE INVENTION

5.1 Background of $1^{st}$ and $3^{rd}$ Order Scattering

Example embodiments according to the invention, are presented in the following. The methods and structure of the instrumentation are applicable to both electromagnetic (EM) and elastic (EL) waves, and to a wide range of frequencies with a wide range of applications. For EL waves one can apply the methods and instrumentation to both shear waves and compression waves, both in the subsonic, sonic, and ultrasonic frequency ranges. We do in the embodiments describe by example ultrasonic measurements or imaging, both for technical and medical applications. This presentation is meant for illustration purposes only, and by no means represents limitations of the invention, which in its broadest aspect is defined by the claims appended hereto.

The most damaging noise in pulse echo wave measurements and imaging has its origin in multiple scattering of the transmitted pulse. We refer to this noise as multiple scattering noise, or pulse reverberation noise. As the amplitude of the scattered pulse drops for each scattering, the $2^{nd}$ and $3^{rd}$ order scattering dominates the noise. With back scatter imaging we mainly have $3^{rd}$ order scattering noise, where the $1^{st}$ scatterer is inside the transmit beam, and the last ($3^{rd}$) scatterer is inside the receive beam. With very wide transmit beams, like with plane wave imaging and similar, we can also observe $2^{nd}$ order scattering noise. However, the major type of strong scatterers are layers of fat and muscles in the body wall, that are fairly parallel, which requires $3^{rd}$ order scattering also with wide transmit beams. Bone structures and air in lungs and intestines can produce $2^{nd}$ order scattering noise with synthetic multi beam imaging (e.g. plane wave imaging)

The invention presents methods and instrumentation for suppression of such multiple scattering noise, and also for measurement and imaging of nonlinear scattering of waves. Such methods and instruments are also presented in U.S. Pat. No. 8,038,616 and U.S. patent application Ser. Nos. 12/351, 766, 12/500,518, and 13/213,965, where the current invention presents new and more advanced methods and instrumentation, utilizing transmission of similar dual band pulse complexes as in said applications.

An example of such a dual band transmitted pulse complex is shown as 101 in FIG. 1a, composed of a low frequency (LF) pulse (102) and a high frequency (HF) pulse (103). The HF pulse is typically shorter than ½ the period of the LF pulse, and the methods utilize the nonlinear manipulation of the object material parameters (e.g. object elasticity) by LF pulse as observed by the co-propagating HF pulse. One typically transmits at least two pulse complexes with differences in the LF pulse, and processes HF receive signals picked up from one or both of scattered and transmitted HF pulses of the at least two transmitted pulse complexes, to suppress the pulse reverberation noise and/or measure or image nonlinear scattering from the object.

Figure 1B:
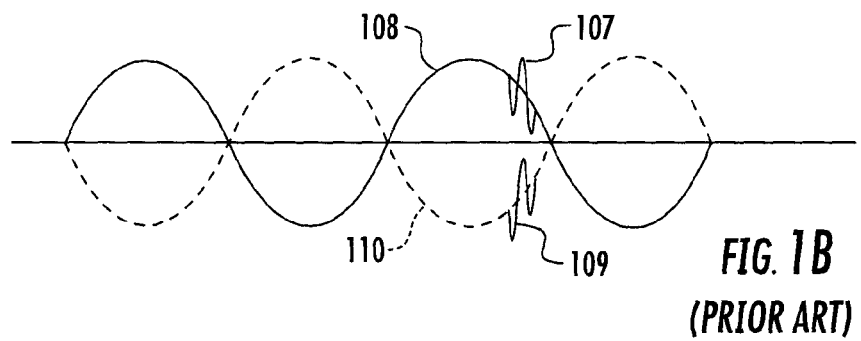

In FIG. 1a is for example shown two pulse complexes (101, 104) with opposite polarities of the LF pulse, shown as 102 versus 105. The same is shown in FIG. 1b with the two polarities (108, 110) of the LF pulse. In FIG. 1a the HF pulse 103 is found at the crest of the LF pulse 102 with a temporal pulse length, $T_{pH}$, so short in relation to the LF pulse oscillation period, $T_L$, that it mainly observes a constant manipulation of the material parameters by the LF pulse observed by the co-propagating HF pulse, and hence both the HF pulse wave propagation velocity and the HF pulse scattering from spatial variations in the parameters. When switching polarity of the LF pulse to 105 so that the HF pulse 106 is found at the trough of the LF pulse, the HF pulse observes a different manipulation of the propagation velocity and scattering by the LF pulse. In FIG. 1b the HF pulses 107 and 109 are found at gradients of the LF pulses 108 and 110 so that the LF manipulation of the propagation velocity varies along the HF pulse, producing a pulse form distortion of the co-propagating HF pulses that accumulates with propagation distance. Due to diffraction of the LF pulse, the position of the HF pulse along the LF pulse oscillation can slide with propagation distance, indicated as the different positions 111, 112, 113 of the HF pulse along the LF pulse oscillation in FIG. 1c, providing mainly a pulse form distortion at positions 111 and 113, and a propagation advancement/delay at position 112.

For more detailed analysis of the reverberation noise we refer to FIG. 2, which in FIG. 2a schematically illustrates the situation for $1^{st}$ order scattering, and in FIG. 2b-c schematically illustrates 3 different classes of $3^{rd}$ order multiple scattering noise, defined as Class I-III. The Figures all show an ultrasound transducer array 200 with a front transmit/receive and reflecting surface 201. The pulse propagation path and direction is indicated with the lines and arrows 202, where the $1^{st}$ scatterer is indicated by the dot 203, and in FIG. 2a with $1^{st}$ order scattering, the transmitted pulse complex propagates to the $1^{st}$ scatterer 203 and back to the transducer where it is transformed to an electrical signal and further processed to form measurement or image signals.

In FIG. 2b-c the backscattered signal from the $1^{st}$ scatterer 203 is reflected/scattered by a $2^{nd}$ scatterer 204 that can have multiple positions as indicated in the Figure. The pulse complex then propagates to a a $3^{rd}$ scatterer 205 where it is reflected back to the transducer 200 where the signal is picked up and further processed to provide measurement or image signals with strong suppression of pulse reverberation nois and/or suppression of linear scattering to enhance HF receive signal components from nonlinear scattering. Due to the multiple positions of the $2^{nd}$ scatterers the two $1^{st}$ and $3^{rd}$ scatterers 203 and 205 then generates a tail of pulse reverberation noise 206 following the deepest of the $1^{st}$ and $3^{rd}$ scatterers. 207 shows for illustrative example a low echogenic region, for example in medicine the cross section of a vessel or a cyst, with a scattering surface 208 that we want to image with high suppression of pulse reverberation noise. The object has so low internal scattering that the pulse reverberation noise 206 generated in the different classes produces disturbances in the definition of the scattering surface 208.

To obtain visible, disturbing reverberation noise in the image, the $1^{st}$-$3^{rd}$ scatterers must be of a certain strength, where the $1^{st}$ scatterer must be inside the transmit beam, and the $3^{rd}$ scatterer must be inside the receive beam. In medical ultrasound applications this is often found by fat layers in the body wall, while in technical applications one can encounter many different structures, depending on the application. In ultrasound applications, the strongest $2^{nd}$ scatterer is often the ultrasound transducer array surface itself, as this can have a reflection coefficient that is ~10 dB or more higher than the reflection coefficient from other soft tissue structures. The pulse reverberation noise that involves the transducer surface as the $2^{nd}$ scatterer, is therefore particularly strong indicated by 209. The definition of Class I-III pulse reverberation noise is in more detail Class I (FIG. 2.1b) is the situation where the $1^{st}$ scatterer (203) is closest to the transducer at fast time (depth time) of $t_1 = 2z_1/c$, where $z_1$ is the depth of the $1^{st}$ scatterer in the $3^{rd}$ order scattering sequence of scatterers, and c is the elastic wave propagation velocity. For Class I pulse reverberations we have $t_1 < t/2$ and $t=2z/c$ is the fast time (depth time) for the reception of the $1^{st}$ order back scattered signal from a scatterer 703 at depth z in FIG. 2a. The $2^{nd}$ scatterer (204) is at the depth $z_2$ and fast time $t_2=2z_2/c$. The distance between the $3^{rd}$ scatterer 205 and the noise point, which in the Figure coincides with the object surface 208, is the same as the distance $d=t_1-t_2$ between the $1^{st}$ and the $2^{nd}$ scatterers. With varying positions of the $2^{nd}$ scatterer 204, we get a tail 206 of pulse reverberation noise. When the transducer surface 201 is the strongest $2^{nd}$ scatterer, we get particularly strong noise at 209.

Class II (FIG. 2.1c) Class II pulse reverberation noise has the same three scatterers as the Class I noise, with $1^{st}$ and $3^{rd}$ scatterers interchanged. Class I and II pulse reverberation noise hence always co-exist, and for Class II noise we have a fast time for the $1^{st}$ scatterer 203 $t_1 > t/2 = z/c$. The reasoning for the tail of pulse reverberation noise 206 is the same as that for Class I, where a strongly reflecting transducer surface gives the noise 209. When the $2^{nd}$ scatterer is the ultrasound transducer array itself, we can define as follows:

Class I reverberations: $1^{st}$ scatterer $z_1 < z/2$ and $3^{rd}$ scatterer $z_3 > z/2$, $z_3 = z - z_1$ Class II reverberations: $1^{st}$ scatterer $z_3 < z/2$ and $3^{rd}$ scatterer $z_1 > z/2$, $z_1 = z - z_3$ Harmonic imaging will mainly suppress Class I pulse reverberation noise where $z_1$ is close to the transducer, where we in the following will show that methods according to this invention suppresses Class I and II pulse reverberation noise combined, regardless of the value of $z_1$, as the nonlinear propagation delay and pulse form distortion of the combined Class I and II noise is quite different from that for the $1^{st}$ oreder scattering Class III (FIG. 2.1d) This is a situation where Class I and Class II merges, i.e. the $1^{st}$ and the $3^{rd}$ scatterers are at the same depth, and the $1^{st}$ scatterer is close to z, i.e. all 3 scatterers are close to z. The nonlinear propagation delay and pulse form distortion for the Class III is therefore similar to that for $1^{st}$ order scattering at the depth the noise is observed, and it is then difficult to suppress Class III noise relative to $1^{st}$ order scattering. When Class III noise co-exists with Class I and II noise and interferes at the same depth, the model based estimation of correction delays and speckle corrections for the noise is able to suppress Class I, II and III noise combined.

We shall first start by analyzing the situation with linear wave propagation.

5.2 Signal Models for $1^{st}$ and $3^{rd}$ Order Scattering in a Linear Material

A. Models for $1^{st}$ Order Scattering

We first analyze the HF receive signal from the $1^{st}$ order scattered wave components within the realm of pressure independent elasticity of the object, i.e. linear elasticity. With reference to FIG. 3 we get the linearly transmitted field as [1]

$$P_t(\underline{r}_1, w; \underline{r}_t) = P_t(w) ik H_t(\underline{r}_1, w; \underline{r}_t) \qquad (1)$$

$$H_t(\underline{r}_1, w; \underline{r}_t) = \int_{S_t} d^2 r_0 2 G(\underline{r}_0, \underline{r}_1; w) e^{-iwt_t(\underline{r}_0, \underline{r}_t)} w_t(\underline{r}_0) H_{abc}(\underline{r}_0, w; \underline{r}_t)$$

$$c t_t(\underline{r}_0, \underline{r}_t) = r_t - |\underline{r}_0 - \underline{r}_t|$$

where w is the angular frequency, $k=w/c$ is the wave number with c as the wave propagation velocity, $P_t(w)$ is the Fourier transform of the transmitted pressure waveform at the transducer surface, $t_t(\underline{r}_0, \underline{r}_1)$ is the transmit delays for focusing the transmit beam at $\underline{r}_t$ in a homogeneous material, $G(\underline{r}_0, \underline{r}_1; w)$ is the Greens function for wave propagation from a source at $\underline{r}_0$ to a field point at $\underline{r}_1$ in the linear, heterogeneous material (i.e. spatial variation in wave propagation velocity), $w_t(\underline{r}_0)$ is an apodization function, and $H_{abc}(\underline{r}_0, w; \underline{r}_t)$ is an aberration correction filter for spatial variations in the wave propagation velocity of the heterogeneous material for focusing at $\underline{r}_t$. In a homogeneous material where the wave propagation velocity parameters are constant in space, we have $H_{abc}(\underline{r}_0, w; \underline{r}_t) = 1$. If $H_{abc}(\underline{r}_0, w; \underline{r}_t)$ is set equal to unity in a heterogeneous material, the beam focusing will be sub-optimal, but the theory presented below will still be valid.

The contribution to the $1^{st}$ order scattered field from scatterer density $u(\underline{r}_1)$ of the infinitesimal volume element $d^3 r_1$ at location $\underline{r}_1$ in $R_1$ in the object (See FIG. 3) is [1]

$$dP_{s1}(\underline{r}, w; \underline{r}_1) = -k^2 P_t(w) ik G(\underline{r}, \underline{r}_1; w) H_t(\underline{r}_1, w; \underline{r}_t) u(\underline{r}_1) d^3 r_1 \qquad (2)$$

For back scattering we have $u(\underline{r}_1) = s_1(\underline{r}_1) - g(\underline{r}_1)$, where $s_1$ and g are the relative spatial variation of the material compressibility and mass density [1]. The total $1^{st}$ ordered scattered field is then found by integration of $dP_{s1}(\underline{r}, w; \underline{r}_1)$ over $\underline{r}_1$ across $R_1$. The $1^{st}$ order received signal for transducer element or sub aperture located at $\underline{r}$ on the receiver transducer $$dS_1(\underline{r}, w; \underline{r}_1) = -k^2 U(w) G(\underline{r}, \underline{r}_1; w) H_t(\underline{r}_1, w; \underline{r}_t) u(\underline{r}_1) d^3 r_1 \qquad (3)$$

where $U(w) = H_{rt}(w) ik P_t(w)$ is the received pulse for the element at $\underline{r}$ from a unit plane reflector [1]. Beam forming this signal over the array with receive beam focus at $\underline{r}_r$, we get the following received $1^{st}$ order scattered signal from $u(\underline{r}_1)$ as [BA]

$$dY_1(w; \underline{r}_1) = \int_{S_r} d^2 r_4 e^{-iwt_r(\underline{r}_4, \underline{r}_r)} w_r(\underline{r}_4) H_{abc}(\underline{r}_4, w; \underline{r}_r) dS_1(\underline{r}_4, w; \underline{r}_1) \qquad (4)$$

$$c t_r(\underline{r}_4, \underline{r}_r) = r_r - |\underline{r}_4 - \underline{r}_r|$$

where $\underline{r}_4$ is the integration coordinate over the receive array surface $S_r$, and $t_r(\underline{r}_4, \underline{r}_r)$ is the beam forming delays for the receiver beam focused at the receiver beam focus $\underline{r}_r$, calculated on the assumption of constant propagation velocity c in the tissue, $w_r(\underline{r}_4)$ is an apodization function, and $H_{abc}(\underline{r}_4, w; \underline{r}_r)$ is the aberration correction filter that compensates for material heterogeneity to focus the receive beam at $\underline{r}_r$. As for the transmit beam, we have $H_{abc}(\underline{r}_4, w; \underline{r}_r) = 1$ for the homogeneous material. Inserting Eq.(3) we can express the received $1^{st}$ order scattered signal as $$dY_1(w; \underline{r}_1) = -k^2 U(w) H_r(\underline{r}_1, w; \underline{r}_r) H_t(\underline{r}_1, w; \underline{r}_t) u(\underline{r}_1) d^3 r_1 \qquad (5)$$

$$H_r(\underline{r}_1, w; \underline{r}_r) = \int_{S_r} d^2 r_4 2 G(\underline{r}_4, \underline{r}_1; w) e^{-iwt_r(\underline{r}_4, \underline{r}_r)} w_r(\underline{r}_4) H_{abc}(\underline{r}_4, w; \underline{r}_r)$$

where $H_r(\underline{r}_1, w; \underline{r}_r)$ is the aberration corrected receive beam at the field point $\underline{r}_1$ when the beam is focused at $\underline{r}_r$.

B. Models for $3^{rd}$ Order Scattering

Multiple scattering is produced because the $1^{st}$ order scattered field in Eq.(2) is in turn scattered from a scatterer at $\underline{r}_2$ in $R_2$ to produce a $2^{nd}$ order scattered field $$dP_{s2}(\underline{r}, w; \underline{r}_1) = \int_{R_2} d^3 r_2 G(\underline{r}, \underline{r}_2; w) s(\underline{r}_2, w) dP_{s1}(\underline{r}_2, w; \underline{r}_1) \qquad (6)$$

where $s(\underline{r}_2,w)$ typically is either a strong volume scatterer distribution $u(\underline{r}_2)$, for example structured fatty layers, where we have $$s(\underline{r}_2,w) = -k^2 u(\underline{r}_2) \tag{7}$$

or reflection from a layer surface or the transducer surface as $$s(\underline{r}_2,w) = ik2R(\underline{r}_2,w)d(S_R(\underline{r}_2)) \tag{8}$$

where $R(\underline{r}_2,w)$ is the reflection coefficient of the reflecting surface $S_R(\underline{r}_2)=0$. In technical applications one often have strongly reflecting surfaces at a distance from the transducer, for example a surface of a metal layer, which can be modeled as Eq.(8) where $S_R(\underline{r}_2)=0$ now defines the layer surface. Strong volume scatterers are modeled as in Eq.(7).

The $2^{nd}$ order scattered field is then scattered a $3^{rd}$ time from the volume scatterer distribution $u(\underline{r}_3)$ and produces a received signal for transducer element or sub aperture located at $\underline{r}_4$ on the receiver transducer $$dS_3(\underline{r}_4,w;\underline{r}_1,\underline{r}_3) = k^2 H_{rt}(\underline{r}_4,w) 2G(\underline{r}_4,\underline{r}_3;w) dP_{s2}(\underline{r}_3,w;\underline{r}_1) u(\underline{r}_3) \tag{9}$$

where $H_{rt}(w)$ is defined in relation to Eq.(3). Introducing the expression for $P_{s1}(\underline{r}_2,w)$ and $P_{s2}(\underline{r}_3,w)$ and from Eqs.(2,6) we can express the received $3^{rd}$ order reverberation element signal as $$dS_3(\underline{r}_4, w; \underline{r}_1, \underline{r}_3) = k^4 U(w) 2G(\underline{r}_4, \underline{r}_3; w) \tag{10}$$
$$u(\underline{r}_3) d^3 r_3 H_{rev}(\underline{r}_3, \underline{r}_1; w) H_t(\underline{r}_1, w; \underline{r}_t) u(\underline{r}_1) d^3 r_1$$

$$H_{rev}(\underline{r}_3, \underline{r}_1; w) = \int_{R_2} d^3 r_2 G(\underline{r}_3, \underline{r}_2; w) s(\underline{r}_2, w) G(\underline{r}_2, \underline{r}_1; w)$$

where $R_2$ is the region of the second scatterers $U(w)=H_{rt}(w)ikP_t(w)$ is the received pulse for the element at $\underline{r}$ for a reflected wave front conformal to the array surface, defined in relation to Eq.(3). Beam forming this signal over the array with receive beam focus at $\underline{r}_r$, we get the following received reverberation beam signal for the reverberations as $$dY_3(w; \underline{r}_1, \underline{r}_3) = \tag{11}$$
$$\int_{S_r} d^2 r_4 e^{-iwt_r(\underline{r}_4,\underline{r}_r)} w_r(\underline{r}_4) H_{abc}(\underline{r}_4, w; \underline{r}_r) dS_3(\underline{r}_4, w; \underline{r}_1, \underline{r}_3)$$

$$ct_r(\underline{r}_4, \underline{r}_r) = r_r - |\underline{r}_4 - \underline{r}_r|$$

where $\underline{r}_4$ is the integration coordinate over the receive array surface $S_r$, and the other functions are as defined in relation to Eqs.(4,5). Inserting Eq.(10) we can express the $3^{rd}$ order reverberation signal as $$dY_3(w;\underline{r}_1,\underline{r}_3) = k^4 U)(w) H_r(\underline{r}_3,w;\underline{r}_r) u(\underline{r}_3) d^3 r_3 H_{rev}(\underline{r}_3, \underline{r}_1;w) H_t(\underline{r}_1 w;\underline{r}_t) u(\underline{r}_1) d^3 r_1 \tag{12}$$

where $H_r(\underline{r}_3,w;\underline{r}_r)$ is the aberration corrected receive beam at the field point $\underline{r}_3$ when the beam is focused at $\underline{r}_r$ as defined in Eq.(5)

5.3 Nonlinear Propagation and Scattering

A. Wave Equation for $2^{nd}$ Order Nonlinear Elasticity

Nonlinear material parameters influences both the wave propagation velocity and the scattering from spatial variations in the nonlinear parameters. For acoustic waves in fluids and solids, the bulk elasticity can generally be approximated to the $2^{nd}$ order in the pressure, i.e. the volume compression dV of a small volume DV, is related to the pressure p $$\frac{dV}{DV} = -\underline{y} = (1 - b_p(\underline{r})p)k(\underline{r})p + h_{ab} \tilde{\otimes}_t k(\underline{r})p \tag{13}$$

where $\underline{y}(\underline{r},t)$ is the acoustic particle displacement vector, $p(\underline{r},t)$ is the acoustic pressure, $k(\underline{r})$ is the linear bulk compressibility of the material, and $b_p(\underline{r})=b_n(\underline{r})k(\underline{r})$ where $b_n(\underline{r})=1+B(\underline{r})/2A(\underline{r})$ is a nonlinearity parameter of the bulk compressibility, and $h_{ab}(\underline{r},t)$ is a convolution kernel that represents absorption of wave energy to heat. The $2^{nd}$ order approximation holds for soft tissue in medical imaging, fluids and polymers, and also rocks that show special high nonlinear bulk elasticity due to their granular micro-structure. Gases generally show stronger nonlinear elasticity, where higher order terms in the pressure often might be included. Micro gas-bubbles with diameter much lower than the acoustic wavelength in fluids, also show a resonant compression response to an oscillating pressure, which is discussed above. When the material parameters can be approximated to $2^{nd}$ order in the wave fields, we can for example for ultrasonic pressure waves formulate a wave equation that includes nonlinear forward propagation and scattering phenomena as [2,3]

$$\underbrace{^2 p(\underline{r}, t) - \frac{1}{c_0^2(\underline{r})} \frac{\partial^2 p(\underline{r}, t)}{\partial t^2}}_{(1) Linear\ propagation} + \tag{14}$$

$$\underbrace{\frac{b_p(\underline{r})}{c_0^2(\underline{r})} \frac{\partial^2 p(\underline{r}, t)^2}{\partial t^2}}_{(2) Nonlinear\ propagation} - \underbrace{h_{ab}(\underline{r}, t) \tilde{\otimes}_t \frac{1}{c_0^2} \frac{\partial^2 p(\underline{r}, t)}{\partial t^2}}_{(3) Absorption} =$$

$$\underbrace{\frac{s_l(\underline{r})}{c_0^2(\underline{r})} \frac{\partial^2 p(\underline{r}, t)}{\partial t^2} + (g(\underline{r}) p(\underline{r}, t))}_{(4) Linear\ scattering\ source\ terms} - \underbrace{\frac{s_n(\underline{r})}{c_0^2(\underline{r})} \frac{\partial^2 p(\underline{r}, t)^2}{\partial t^2}}_{(5) Nonlinear\ scattering\ source\ term}$$

where $c_0(\underline{r})$ is the linear wave propagation velocity for low field amplitudes, $s_l(\underline{r})$ and $g(\underline{r})$ are linear scattering parameters given by the relative spatial variation of the material compressibility and mass density, and $s_n(\underline{r})$ is a nonlinear scattering parameter. The left side propagation parameters vary with $\underline{r}$ on a scale>approximately the wavelength, while the right side scattering parameters vary with $\underline{r}$ on a scale<approximately the wave length. A similar equation for shear waves and electromagnetic waves can be formulated that represents similar nonlinear propagation and local scattering phenomena for the shear and EM waves.

B. Nonlinear Interaction in Dual Band Pulse Complexes

The different terms of Eq.(14) have different effects on the wave propagation and scattering: The linear propagation terms (1) guide the forward spatial propagation of the incident wave without addition of new frequency components. The linear scattering source terms (4) produce local scattering of the incident wave without addition of new frequency components, i.e. the linearly scattered wave has the same frequency components as the incident wave, with an amplitude modification $\sim w^2$ produced by $2^{nd}$ order differentiation in the scattering terms.

For materials with adequately high nonlinearity in the material parameters relative to the wave field amplitude, the nonlinearity affects both the propagation and local scattering of the wave. A slow variation (close to constant on scale>~wave length) of the nonlinear parameters give a value to $b_p(\underline{r})$ that provides a nonlinear forward propagation distortion of the incident waves that accumulates in amplitude with propagation distance through term (2). A rapid variation of the nonlinear material parameters (on scale<~wavelength) gives a value to $s_n(\underline{r})$ that produces a local nonlinear scattering of the incident wave through term (5).

We study the situation where the total incident wave is the sum of the LF and HF pulses, i.e. $p(\underline{r},t)=p_L(\underline{r},t)+p_H(\underline{r},t)$. The nonlinear propagation and scattering are in this $2^{nd}$ order approximation both given by $$\sim p(r,t)^2 = \qquad (15)$$
$$(p_L(\underline{r},t)+p_H(\underline{r},t))^2 = \underbrace{p_L(\underline{r},t)^2}_{\text{nonlin self distortion}} + \underbrace{2p_L(\underline{r},t)p_H(\underline{r},t)}_{\text{nonlin interaction}} + \underbrace{p_H(\underline{r},t)^2}_{\text{nonlin self distortion}}$$

A multiplication of two functions in the temporal domain produces a convolution of the functions temporal Fourier transforms (i.e. temporal frequency spectra) introducing frequency components in the product of the functions that are sums and differences of the frequency components of the factors of the multiplication. The squares $p_L^2$ and $p_H^2$ then produces a self-distortion of the incident pulses that pumps energy from the incident fundamental bands into harmonic components of the fundamental bands, and is hence found as a nonlinear attenuation of the fundamental bands of both the LF and HF waves. However, the wave amplitude determines the self-distortion per wave length, and the LF pulse typically propagates only up to ~30 LF wavelengths into the object which allows us to neglect both nonlinear self distortion and nonlinear attenuation for the LF wave. The HF wave, thereagainst, propagates up to ~250 HF wavelengths into the object, so that both the nonlinear self-distortion an the nonlinear attenuation becomes observable. We return to these phenomena for simulations of the wave propagation in Section 5.8B.

C. Nonlinear Propagation and Scattering for Dual Band Pulse Complexes

When the temporal HF pulse length $T_{pH}$ is much shorter than half the period of the LF pulse, $T_L/2$, i.e. the bandwidth of the HF pulse $B_{HF} > w_L/2$, where $w_L = 2p/T_L$ is the angular frequency of the LF wave, the sum and difference frequency spectra overlaps with each other and the fundamental HF spectrum. This is the situation illustrated in FIG. 1. For the further analysis we assume that $|2b_p(\underline{r})p_L(\underline{r},t)|=|x|<<1$ which allows the approximation $1-x \approx 1/(1+x)$ and the propagation terms of the left side of Eq.(14) can for the manipulation of the HF pulse by the co-propagating LF pulse be approxiomated as $$\nabla^2 p_H(\underline{r},t) - \underbrace{\frac{1}{c_0^2(\underline{r})}\frac{\partial^2 p_H(\underline{r},t)}{\partial t^2}}_{(1)\text{Linear propagation}} + \underbrace{\frac{2b_p(\underline{r})p_L(\underline{r},t)}{c_0^2(\underline{r})}\frac{\partial^2 p_H(\underline{r},t)}{\partial t^2}}_{(2)\text{Nonlinear propagation}} \gg \qquad (16)$$

$$\nabla^2 p_H(\underline{r},t) - \frac{1}{c_0^2(\underline{r})(1+2b_p(\underline{r})p_L(\underline{r},t))}\frac{\partial^2 p_H(\underline{r},t)}{\partial t^2}$$

The numerator in front of the temporal derivative in this propagation operator is the square propagation velocity, and we hence see that the LF pulse pressure $p_L$ modifies the propagation velocity for the co-propagating HF pulse $p_H$ as $$c(\underline{r},p_L) = \sqrt{c_0^2(\underline{r})(1+2b_p(\underline{r})p_L)} \gg c_0(\underline{r})(1+b_p(\underline{r})p_L) \qquad (17)$$

where $p_L$ is the actual LF field variable along the co-propagating HF pulse. The orthogonal trajectories of the HF pulse wave fronts are paths of energy flow in the HF pulse propagation. The propagation lag of the HF pulse along the orthogonal trajectories of the HF pulse wave-fronts, $G(\underline{r})$, can then be approximated as $$t(\underline{r}) = \int_{G(\underline{r})} \frac{ds}{c(s, p\, p_L(s))} \gg \int_{G(\underline{r})} \frac{ds}{c_0} - p\int_{G(\underline{r})} \frac{ds}{c_0} b_p(s) p_L(s) = \qquad (18)$$
$$t_0(\underline{r}) + pt(\underline{r})$$

$$t_0(\underline{r}) = \int_{G(\underline{r})} \frac{ds}{c_0(s)}$$

$$pt(\underline{r}) = -p\int_{G(\underline{r})} \frac{ds}{c_0(s)} b_p(s) p_L(s)$$

where $p\, p_L(\underline{s})$ is the LF pressure at the center of gravity at $\underline{s}$ of the co-propagating HF pulse, and $p$ is a scaling/polarity variable for the LF pulse that is extracted to more clearly show results of scaling the amplitude and changing the polarity of the LF pulse. The propagation lag without manipulation of the propagation velocity by the LF pulse is $t_0(\underline{r})$. $t(\underline{r})$ is the added nonlinear propagation delay produced by the nonlinear manipulation of the propagation velocity for the HF pulse by the LF pressure $p_L(\underline{s})$. We note that when the $1^{st}$ scattering/reflection occurs, the LF pressure $p_L$ drops so much that the LF modification of the propagation velocity is negligible for the scattered HF wave. This means that we only get contribution in the integral for $t(\underline{r})$ up to the $1^{st}$ scattering, an effect that we will use to suppress multiple scattered waves in the received signal and to enhance the nonlinear scattering components.

Variations of the LF pressure along the co-propagating HF pulse produces a variation of the propagation velocity along the HF pulse, that in turn produces a nonlinear pulse from distortion of the HF pulse that accumulates with propagation distance. When $B_{HF} > w_{LF}/2$ the nonlinear propagation distortion can be described by a filter, as shown below in Eqs.(19, 23).

In summary, the nonlinear propagation term, i.e. term (2) in Eq.(14) produces:

i) A nonlinear propagation delay $t(\underline{r})$ produced by the LF pressure at the center of gravity of the co-propagating HF pulse according to Eq.(18), and is accumulated up to the 1st scattering, where the amplitude of the LF pulse drops so much that the effect of the LF pulse can be neglected after this point.

ii) A nonlinear propagation distortion of the HF pulse produced by the variation of the LF pulse field along the co-propagating HF pulse that accumulates with propagation distance up to the $1^{st}$ scattering, where the amplitude of the LF pulse drops so much that the effect of the LF pulse can be neglected after this point.

iii) A nonlinear self-distortion of the HF pulse which up to the $1^{st}$ scattering transfers energy from the fundamental HF band to harmonic components of the fundamental HF band, and is hence found as a nonlinear attenuation of the fundamental band of the HF pulse.

When $B_{HF} > w_{LF}/2$ the transmitted HF pulse field $P_t(\underline{r}_1,w;\underline{r}_t)$ hence observes a nonlinear propagation distortion as described by point i)-iii) above and takes the form $P_{tp}(\underline{r}_1,w;\underline{r}_t)$ $$P_{tp}(\underline{r}_1, w; \underline{r}_t) = V_p(\underline{r}_1, w; \underline{r}_t) P_t(\underline{r}_1, w; \underline{r}_t) \qquad (19)$$

-continued
$$V_p(\underline{r}_1, w; \underline{r}_t) = \frac{P_{tp}(\underline{r}_1, w; \underline{r}_t)}{P_t(\underline{r}_1, w; \underline{r}_t)} = \tilde{V}_p(\underline{r}_1, w; \underline{r}_t)e^{-iwpt(\underline{r}_1)}$$

where the subscript p designates the amplitude/polarity/phase of the LF pulse. $P_t(\underline{r}_1,w;\underline{r}_t)$ is given in Eq.(1), and $V_p$ includes all nonlinear forward propagation distortion, where the linear phase component of $V_p$ is separated out as the nonlinear propagation delay $pt(\underline{r}_1)$ up to the point $\underline{r}_1$. $\tilde{V}_p$ hence represents the nonlinear pulse form distortion of the HF pulse by the co-propagating LF pulse, and also the nonlinear attenuation produced by the nonlinear self distortion of the HF pulse.

The nonlinear scattering term (5) in Eq.(14) can for the nonlinear interaction term be approximated within the same regime as $$\underbrace{\frac{s_n(\underline{r})}{c_0^2(\underline{r})}\frac{\P^2 p(\underline{r},t)}{\P t^2} \gg \frac{2s_n(\underline{r})p\ p_L(\underline{r},t)}{c_0^2(\underline{r})}\frac{\P^2 p_H(\underline{r},t)}{\P t^2}}_{\text{(5)Nonlinear scattering source term}}$$
(20)

We hence see that when the temporal pulse length of the HF pulse $T_{pH} < T_L/2$, the local LF pulse pressure at the co-propagating HF pulse exerts an amplitude modulation of the scattered wave, proportional to $p\ 2s_n(\underline{r})p_L(\underline{r},t)$. For the nonlinear self-distortion, term (5) produces harmonic components in the scattered wave, and is not noticed in the fundamental HF band.

The effect of nonlinearity of material parameters on the scattered signal, can hence be split into two groups:

Group A originates from the linear scattering, i.e. term (4) of Eq.(14), of the forward, accumulative nonlinear propagation distortion of the incident wave, i.e. combination of term (2) and term (4) in Eq.(14), which is split into a nonlinear propagation delay according to Eq.(18) (i above), a nonlinear pulse form distortion (ii above), and a nonlinear attenuation of the HF pulse (iii above), and Group B originates directly in the local nonlinear scattering, i.e. term (5), of the original frequency components in the incident wave, i.e. interaction between term (1), the nonlinear propagation delay of term (2) and term (5), where the local LF pulse pressure at the co-propagating HF pulse exerts an amplitude modulation of the scattered wave, proportional to $p\ 2s_n(\underline{r})p_L(\underline{r},t)$.

There is also a Group C found as local nonlinear scattering from term (5) of the forward accumulative nonlinear propagation distortion components in the incident wave, i.e. interaction between the pulse distortion component of term (2) and term (5) in Eq.(14), but typical nonlinear material parameters are so low that this group is negligible.

5.4 Signal Models for Nonlinear Propagation and Scattering

A. Models for $1^{st}$ Order Scattering

The $1^{st}$ order linear and nonlinear scattered wave that hits the receiver array at $\underline{r}$ is then from Eq.(2,19,20)

$$dP_{l1}(\underline{r},w;\underline{r}_1) = -k^2 G(\underline{r},\underline{r}_1;w) P_{tp}(\underline{r}_1,w;\underline{r}_t) u(\underline{r}_1) d^3 r_1$$

$$dP_{n1}(\underline{r},w;\underline{r}_1) = -k^2 G(\underline{r},\underline{r}_1;w) P_{tp}(\underline{r}_1,w;\underline{r}_t) 2p_L(\underline{r}_1) s_n(\underline{r}_1) d^3 r_1$$
(21)

The received signal from the $1^{st}$ order linear and nonlinear scattering of the forward nonlinear distorted pressure pulse for the focused and aberration corrected receive beam is hence $$dY_{l1}(w;\underline{r}_1) = -k^2 H_r(\underline{r}_1,w;\underline{r}_r) U_p(\underline{r}_1,w;\underline{r}_t) u(\underline{r}_1) d^3 r_1$$

$$dY_{n1}(w;\underline{r}_1) = -k^2 H_r(\underline{r}_1,w;\underline{r}_r) U_p(\underline{r}_1,w;\underline{r}_t) 2p_L(\underline{r}_1) s_n(\underline{r}_1) d^3 r_1$$

$$U_p(\underline{r}_1,w;\underline{r}_t) = H_{rt}(w) P_{tp}(\underline{r}_1,w;\underline{r}_t) = V_p(\underline{r}_1,w;\underline{r}_t) U(w) H_t(\underline{r}_1,w;\underline{r}_t)$$
(22)

where we have assumed that the pressure to signal transfer function $H_{rt}(w)$ of the transducer elements, is the same for all receiver array elements. Introducing the scaling variable p for the LF field, $p_L(\underline{r}_1)$ fi $p\ p_L(\underline{r}_1)$, the total $1^{st}$ order scattered wave takes the form $$dY_{1p}(w;\underline{r}_1) = V_p(\underline{r}_1,w;\underline{r}_t)\{dX_l(w;\underline{r}_1) + pdX_n(w;\underline{r}_1)\}$$
(23)

$$dX_l(w;\underline{r}_1) = -k^2 U(w) H_r(\underline{r}_1,w;\underline{r}_r) H_t(\underline{r}_1,w;\underline{r}_t) u(\underline{r}_1) d^3 r_1$$

$$dX_n(w;\underline{r}_1) = -k^2 U(w) H_r(\underline{r}_1,w;\underline{r}_r) H_t(\underline{r}_1,w;\underline{r}_t) 2s_n(\underline{r}_1) p_L(\underline{r}_1) d^3 r_1$$

$$V_p(\underline{r}_1,w;\underline{r}_t) = \frac{U_p(\underline{r}_1,w;\underline{r}_t)}{U(w) H_t(\underline{r}_1,w;\underline{r}_t)} = \tilde{V}_p(\underline{r}_1,w;\underline{r}_t)e^{-iwpt(\underline{r}_1)}$$

The magnitude of the nonlinear scattering component is generally much lower than the linear scattering component. To estimate this nonlinear scattering component one could typically transmit two pulse complexes with opposite polarities of the LF pulse, giving the HF receive signals $$dY_+(w;\underline{r}_1) = V_+(\underline{r}_1,w;\underline{r}_t) dX_l(w;\underline{r}_1) + V_+(\underline{r}_1,w;\underline{r}_t) dX_n(w;\underline{r}_1)$$

$$dY_-(w;\underline{r}_1) = V_-(\underline{r}_1,w;\underline{r}_t) dX_l(w;\underline{r}_1) - V_-(\underline{r}_1,w;\underline{r}_t) dX_n(w;\underline{r}_1)$$
(24)

The nonlinear scattering component is then obtained as $$2dX_n(w;\underline{r}_1) = V_+(\underline{r}_1,w;\underline{r}_t)^{-1} dY_+(w;\underline{r}_1) - V_-(\underline{r}_1,w;\underline{r}_t)^{-1} dY_-(w;\underline{r}_1)$$
(25)

where $V_-(\underline{r}_1,w;\underline{r}_t)^{-1} = \tilde{V}_-(\underline{r}_1,w;\underline{r}_t)^{-1} e^{iwpt(\underline{r}_1)}$ are the inverse filters of $V_-(\underline{r}_1,w;\underline{r}_t)$ in Eq.(24). The inverse filter is hence composed of a delay correction $\mp pt(\underline{r}_1)$, and a pulse distortion correction $\tilde{V}_-(\underline{r}_1,w;\underline{r}_t)^{-1}$.

The signal is received as a function of the fast time (or depth-time) t, where we assign a depth z in the image as $z = ct/2$. When one have a distribution of scatterers, one must sum over the scatterer coordinate $\underline{r}_1$, and the LF pressure can in addition to the non-linear propagation delay produce a LF pressure dependent speckle in the received signal that we discuss in Section 5.7. One then needs to generalize the correction for nonlinear propagation delay to correction with a correction delay that is an average nonlinear propagation delay, and generalize the pulse form correction to a speckle correction, as further discussed in Sections 5.7 and 5.8.

C. Models for $3^{rd}$ Order Scattering

For $3^{rd}$ order multiple scattering, the nonlinear propagation delay and pulse form distortion will be a function of the first scatterer coordinate $\underline{r}_{1,3}$, as both the LF and HF pulse amplitudes drop so much in this first scattering that we get linear propagation after the $1^{st}$ scattering. The nonlinear effect with dual band pulse complexes as above, hence modifies the $3^{rd}$ order scattered signals in Eq.(12) to $$dY_{Ip}(w;\underline{r}_1,\underline{r}_3) = k^4 H_r(\underline{r}_3,w;\underline{r}_r) u(\underline{r}_3) d^3 r_3 H_{rev}(\underline{r}_3,\underline{r}_1;w) U_p(\underline{r}_1,w;\underline{r}_t) u(\underline{r}_1) d^3 r_1$$

$$dY_{IIp}(w;\underline{r}_1,\underline{r}_3) = k^4 H_r(\underline{r}_1,w;\underline{r}_r) u(\underline{r}_1) d^3 r_1 H_{rev}(\underline{r}_1,\underline{r}_3;w) 4 U_p(\underline{r}_3,w;\underline{r}_t) u(\underline{r}_3) d^3 r_3$$
(26)

where $dY_{Ip}(w;\underline{r}_1,\underline{r}_3)$ and $dY_{IIp}(w;\underline{r}_1,\underline{r}_3)$ are Class I and II multiple scattering noise with non-zero LF pulse, $U_p$ is the HF receive pulse from a plane reflector. The sum of the Class I and Class II pulse reverberation noise can then be written as $$dY_p(w; \underline{r}_1, \underline{r}_3) = dY_{Ip}(w; \underline{r}_1, \underline{r}_3) + dY_{IIp}(w; \underline{r}_1, \underline{r}_3) = \quad (27)$$

$$\left\{ \frac{H_r(\underline{r}_3, w; \underline{r}_r)U_p(\underline{r}_1, w; \underline{r}_t)}{H_r(\underline{r}_1, w; \underline{r}_r)H_t(\underline{r}_3, w; \underline{r}_t)U(w)} + \frac{U_p(\underline{r}_3, w; \underline{r}_t)}{H_t(\underline{r}_3, w; \underline{r}_t)U(w)} \right\}$$

$$dY_{3II}(w; \underline{r}_1, \underline{r}_3)$$

where $dY_{3II}(w;\underline{r}_1,\underline{r}_3)$ is Class II multiple scattering with zero LF pulse, i.e. linear wave propagation as given from Eq.(12) with $r_3 > r_1$ $$dY_{3II}(w;\underline{r}_1,\underline{r}_3) = k^4 U(w) H_r(\underline{r}_1,w;\underline{r}_r) u(\underline{r}_1) d^3 r_1 H_{rev}(\underline{r}_1, \underline{r}_3;w) H_t(\underline{r}_3,w;\underline{r}_t) u(\underline{r}_3) d^3 r_3 \quad (28)$$

Comparing with Eqs. (19,22,23) we can rewrite Eq.(27) as $$dY_p(w; \underline{r}_1, \underline{r}_3) = K_p(w; \underline{r}_1, \underline{r}_3) dY_{3II}(w; \underline{r}_1, \underline{r}_3) \quad (29)$$

$$K_p(w; \underline{r}_1, \underline{r}_3) = Q(w; \underline{r}_1, \underline{r}_3) V_p(\underline{r}_1, w; \underline{r}_t) + V_p(\underline{r}_3, w; \underline{r}_t)$$

$$Q(w; \underline{r}_1, \underline{r}_3) = \frac{H_t(\underline{r}_1, w; \underline{r}_t) H_r(\underline{r}_3, w; \underline{r}_r)}{H_r(\underline{r}_1, w; \underline{r}_r) H_t(\underline{r}_3, w; \underline{r}_t)} = \frac{\hat{Q}(w; \underline{r}_3)}{\hat{Q}(w; \underline{r}_1)}$$

$$\hat{Q}(w; \underline{r}) = \frac{H_r(\underline{r}, w; \underline{r}_r)}{H_t(\underline{r}, w; \underline{r}_t)}$$

The nonlinear modification by the LF pulse of the HF pulse $U_p$ from the linear form $UH_t$ is hence given by $V_p$ that is defined in Eqs.(19,22,23), while Q represents the difference between Class I and Class II pulse reverberations in the linear propagation regime. Note that when $\underline{r}_1$ fi $\underline{r}_3$, we have Q fi 1 and $V_{p3}$ fi $V_{p1}$. The linear phase component of $V_p$ represents the nonlinear propagation delay $pt(\underline{r}_i)$ up to the point $\underline{r}_i$, $i=1,3$, of the 1$^{st}$ scatterer where the amplitude of both the LF and HF pulses drops so much that one have basically linear wave propagation after this point. The nonlinear pulse form distortion due to variations of the LF pulse along the co-propagating HF pulse and also the nonlinear attenuation of the fundamental band of the HF pulse due to self distortion of the HF pulse, is included in $\tilde{V}_p$ of Eqs. (19,23). This nonlinear attenuation reduces the magnitude of $\tilde{V}_p(\underline{r},w;\underline{r}_t)$ with depth up to the 1$^{st}$ scatterer, hence reducing $|\tilde{V}_p(\underline{r}_3,w;\underline{r}_t)|$ compared to $|\tilde{V}_p(\underline{r}_1,w;\underline{r}_t)|$ in Eq. (29)

In Eq. (29) the total pulse reverberation noise with nonzero LF pulse is hence a filtered version of the Class II reverberation with zero LF pulse, $dY_{3II}(w;\underline{r}_1,\underline{r}_3)$, where the filter depends on the LF pulse in relation to the co-propagating HF pulse and has the form $$K_p(w; \underline{r}_1, \underline{r}_3) = Q(w; \underline{r}_1, \underline{r}_3) \tilde{V}_p(\underline{r}_1, w; \underline{r}_t) e^{-iwpt(\underline{r}_1)} + \quad (30)$$

$$\tilde{V}_p(\underline{r}_3, w; \underline{r}_t) e^{-iwpt(\underline{r}_3)}$$

$$= e^{-iwp[t(\underline{r}_1)+t(\underline{r}_3)]/2} \tilde{K}_p(w; \underline{r}_1, \underline{r}_3)$$

$$\tilde{K}_p(w; \underline{r}_1, \underline{r}_3) =$$

$$Q(w; \underline{r}_1, \underline{r}_3) \tilde{V}_p(w; \underline{r}_1) e^{iwp[t(\underline{r}_3)-t(\underline{r}_1)]/2} + \tilde{V}_p(w; \underline{r}_3) e^{-iwp[t(\underline{r}_3)-t(\underline{r}_1)]/2}$$

The effect of this filter for a distribution of scatterers is discussed in Section 5.7B below.

5.5 Synthetic Transmit and Receive Beams

A. 1$^{st}$ Order Scattering with Multi-Component Transmit

With synthetic transmit and receive beams it is possible to obtain Q=1 in a large group of image points without loosing frame rate. With such methods, one transmits a set of wide transmit beams $\{H_{tj}(\underline{r},w); j=1, \ldots, J\}$ with different directions. With a linear array shown as 400 in FIG. 4, $H_{tj}(\underline{r},w)$ can for example be beams with close to plane wave fronts with different directions in the azimuth direction, while the elevation variation of the beams are the same as with standard fixed focusing. With two-dimensional arrays, $H_{tj}(\underline{r},w)$ can have close to plane wave fronts in both the azimuth and elevation directions. An example of such a plane wave front in the azimuth direction is shown in 401 of FIG. 4. The plane wave is transmitted at an angle $j_j$ to the array, and we define t=0 so that the center element transmits at t=0. For each transmit beam direction, the HF receive signal is picked up in parallel at all array elements.

The signal is received on all elements for each transmit beam that gives the following set $\{Y_{jk}(w); j=1, \ldots, J; k=1, \ldots, K\}$ HF receive element signals from element #k with transmit beam #j. The 1$^{st}$ order scattered HF receive signal is in its linear approximation given from Eq.(5) as $$dY_{jk}(w;\underline{r}_1) = -k^2 U(w) H_{rk}(\underline{r}_1,w) H_{tj}(\underline{r}_1,w) u(\underline{r}_1) d^3 r \quad (31)$$

where $H_{rk}(\underline{r}_1,w)$ is the receive beam of element #k at the location $\underline{r}_1$ (405) of a scatterer. For the image reconstruction we use the time signal of the HF receive element signal obtained as the inverse Fourier transform of Eq. (31)

$$dy_{jk}(t; \underline{r}_1) = c^{-2} \ddot{u}(t) \overset{\sim}{*}_t h_{rk}(\underline{r}_1, t) \overset{\sim}{*}_t h_{tj}(\underline{r}_1, t) u(\underline{r}_1) d^3 r_1 \quad (32)$$

where $h_{rk}(\underline{r}_1,t)$ is the spatial impulse response of array element #k, and $h_{tj}(\underline{r}_1,t)$ is the spatial impulse response for transmit beam #j, both obtained by inverse Fourier transform of the spatial frequency responses $H_{rk}(\underline{r}_1,w)$ and $H_{tj}(\underline{r}_1,w)$ in Eq.(31).

We reconstruct an image signal in a spatial location $\underline{r}$ (402) of the image with a synthetic receive beam and a synthetic transmit beam that are both focused at $\underline{r}$ as $$dz(\underline{r}; \underline{r}_1) = \quad (33)$$

$$dy(2r/c; \underline{r}_1) = \sum_{j,k} a_k(\underline{r}) b_j(\underline{r}) dy_{jk}(2r/c - t_{rk}(\underline{r}) - t_{tj}(\underline{r}); \underline{r}_1)$$

$$ct_{rk}(x, z) = z - \sqrt{(x_k - x)^2 + z^2}$$

$$ct_{tj}(x, z) = x \sin j_j + z(\cos j_j - 1)$$

where $r=|\underline{r}|$ and $t_{rk}(\underline{r})$ is the focusing delay for HF receive element #k (404) for focusing the receive beam centered around x onto $\underline{r}=x\underline{e}_x+z\underline{e}_z$, $a_k(\underline{r})$ is a receive beam apodization function, $t_{tj}(\underline{r})$ is a delay for component transmit beam #j to provide a synthetic transmit beam focused at $\underline{r}$, and $b_j(\underline{r})$ is a transmit beam apodization function. Introducing the HF receive element signals from Eq. (32), the reconstructed image signal is $$dz_1(\underline{r}; \underline{r}_1) = c^{-2} \ddot{u}(2r/c) \otimes_t \sum_k a_k h_{rk}(\underline{r}_1, r/c - \tau_{rk}(\underline{r})) \otimes_t \quad (34)$$

$$\sum_j b_j h_{tj}(\underline{r}_1, r/c - \tau_{tj}(\underline{r})) v(\underline{r}_1) d^3 r_1$$

$$= c^{-2} \ddot{u}(2r/c) \otimes_t h_r(\underline{r}_1, t; \underline{r}) \otimes_t h_t(\underline{r}_1, t; \underline{r}) v(\underline{r}_1) d^3 r_1$$

-continued $$h_r(\underline{r}_1, t; \underline{r}) = \sum_k a_k h_{rk}(\underline{r}_1, t - \tau_{rk}(\underline{r}))$$

$$h_t(\underline{r}_1, t; \underline{r}) = \sum_j b_j h_{tj}(\underline{r}_1, t - \tau_{tj}(\underline{r}))$$

$h_r(\underline{r}_1,t;\underline{r})$ and $h_t(\underline{r}_1,t;\underline{r})$ are the spatial impulse responses of the synthetic transmit and receive beams for a linear material. Out of the total array width, $D_{arr}$, one can hence operate with a synthetic receive aperture $D_r$ determined by how many elements one sums over, and a synthetic transmit aperture determined by how many transmit beam components one sums over. With a non-zero LF pulse we get the synthetic linearly and nonlinearly scattered signals as in Eq.(23), with the synthetic transmit and receive beams of Eq.(34). We should note that the LF pressure that produces the nonlinear propagation delay and the pulse form distortion is the actual LF pressure for each transmitted component $H_{tj}(\underline{r},w)$.

For dual frequency pulse complexes in a nonlinear material, the HF receive signal from component transmit pulse #j at HF receive array element #k is $$dy_{jk}(t; \underline{r}_1) = c^{-2} h_{rk}(\underline{r}_1, t) \tilde{*}_t h_{tj}(\underline{r}_1, t) \tilde{*}_t \ddot{u}_{pj}(\underline{r}_1, t) u(\underline{r}_1) d^3 r_1 \quad (35)$$

$$u_{pj}(\underline{r}_1, t) = v_{pj}(\underline{r}_1, t) \tilde{*}_t u(t) \tilde{*}_t h_{tj}(\underline{r}_1, t)$$

$$v_{pj}(\underline{r}_1, t) = \tilde{v}_p(\underline{r}_1, t - pt(\underline{r}_1))$$

$u_{pj}(\underline{r}_1,t)$ is the forward propagating HF pressure pulse #j convolved with the receive element impulse response, similar to Eq.(23). $u_{pj}(\underline{r}_1,t)$ has undergone a nonlinear propagation delay and pulse form distortion by the co-propagating LF pulse, and also the nonlinear self distortion.

Applying the synthetic image reconstruction as in Eq. (33, 34) we get $$dy_l(2r/c; \underline{r}_1) = c^{-2} h_r(\underline{r}_1, 2r/c; \underline{r}) \tilde{*}_t \ddot{u}_{pt}(\underline{r}_1, 2r/c; \underline{r}) u(\underline{r}_1) d^3 r_1 \quad (36)$$

$$dy_n(2r/c; \underline{r}_1) =$$

$$c^{-2} h_r(\underline{r}_1, 2r/c; \underline{r}) \tilde{*}_t \ddot{u}_{pt}(\underline{r}_1, 2r/c; \underline{r}) 2 s_n(\underline{r}_1) p_L(\underline{r}_1) d^3 r_1$$

$$u_{pt}(\underline{r}_1, 2r/c; \underline{r}_1) = \sum_j u_{p,j}(\underline{r}_1, t - t_{tj}(\underline{r}))$$

This expression has the same form as for the focused transmit and receive beams in Eq.(22), and We hence also get the same form for the total $1^{st}$ order HF receive signal with transmitted dual frequency pulse complexes in a nonlinear material as in Eq.(23). Signal processing for the multi component transmit beam imaging hence takes the same form as for focused transmit and receive beams.

B. $3^{rd}$ Order Scattering with Multi-Component

The image reconstruction is hence based on the assumption of $1^{st}$ order scattering. However, each HF receive element signal will contain multiple scattering noise, where the $3^{rd}$ order scattering noise given by the formula in Eq.(26) is the most dominating component. The HF receive element signal for element #k and component transmit beam #j for the $3^{rd}$ order scattered pulse reverberations of Class I and II with nonlinear propagation of the transmit pulse up to the $1^{st}$ scatterer, is hence $$dy_{lp,jk}(t; \underline{r}_1, \underline{r}_3) = \quad (37)$$

$$c^{-4} h_{rk}(\underline{r}_3, t) u(\underline{r}_3) d^3 r_3 \tilde{*}_t h_{rev}(\underline{r}_3, \underline{r}_1; t) \tilde{*}_t u^{(4)}_{p,j}(\underline{r}_1, t) u(\underline{r}_1) d^3 r_1$$

$$dy_{llp,jk}(t; \underline{r}_1, \underline{r}_3) = c^{-4} h_{rk}(\underline{r}_1, t) u(\underline{r}_1)$$

$$d^3 r_1 \tilde{*}_t h_{rev}(\underline{r}_3, \underline{r}_1; t) \tilde{*}_t u^{(4)}_{p,j}(\underline{r}_1, t) u(\underline{r}_3) d^3 r_3$$

$$dy_{3p,jk}(t; \underline{r}_1, \underline{r}_3) = dy_{lp,jk}(t; \underline{r}_1, \underline{r}_3) + dy_{llp,jk}(t; \underline{r}_1, \underline{r}_3)$$

where $u_{pj}^{(4)}$ is the transmitted nonlinear HF pulse component #j at $\underline{r}_1$, scattered twice from a point scatterer and received through the transducer element. Reconstructing an image signal at $\underline{r}$ according to the lines of Eqs.(33,34), the reconstructed signal will contain a $3^{rd}$ order pulse reverberation component according to $$dy_{lp}(2r/c; \underline{r}_1, \underline{r}_3) = \sum_{j,k} dy_{p,jk}(2r/c - \tau_{rk}(\underline{r}) - \tau_{tj}(\underline{r}); \underline{r}_1, \underline{r}_3) \quad (38)$$

$$= dy_{lp}(2r/c; \underline{r}_1, \underline{r}_3) + dy_{llp}(2r/c; \underline{r}_1, \underline{r}_3)$$

where the Class I and Class II components are $$dy_{lp}(t; \underline{r}_1, \underline{r}_3) = \quad (39)$$

$$c^{-4} h_r(\underline{r}_3, t; \underline{r}_t) u(\underline{r}_3) d^3 r_3 \tilde{*}_t h_{rev}(\underline{r}_3, \underline{r}_1; t) \tilde{*}_t u^{(4)}_p(\underline{r}_1, t; \underline{r}_t) u(\underline{r}_1) d^3 r_1$$

$$dy_{llp}(t; \underline{r}_1, \underline{r}_3) = c^{-4} h_r(\underline{r}_1, t; \underline{r}_r) u(\underline{r}_1)$$

$$d^3 r_1 \tilde{*}_t h_{rev}(\underline{r}_3, \underline{r}_1; t) \tilde{*}_t u^{(4)}_p(\underline{r}_3, t; \underline{r}_t) u(\underline{r}_3) d^3 r_3$$

$$u_p(\underline{r}_1, t; \underline{r}) = \sum_j b_k u_{pj}(\underline{r}_1, t - t_{tj}(\underline{r}))$$

The pulse reverberation noise of the reconstructed HF receive signals hence has the same form as for the focused transmit and receive beams as in Eq.(26). By matching the number of transmit beam components and apodization weights that participates to the synthetic transmit beam to the aperture and apodization weights of the synthetic receive beam we can obtain $$H_r(\underline{r}_i, w; \underline{r}) = H_t(\underline{r}_i, w; \underline{r}) i = 1,3 \quad \hat{Q}(w; \underline{r}) = 1 \quad Q(w; \underline{r}_1, \underline{r}_3) = 1 \quad (40)$$

in Eq.(29), and the difference between the Class I and II pulse reverberation noise is found in the nonlinear pulse form distortion produced by the LF pulse and the nonlinear self distortion attenuation of the fundamental HF band, produced by the HF pulse itself, both given by $\hat{V}_p(\underline{r}_1,w)$ and $\hat{V}_p(\underline{r}_3,w)$. The estimation schemes of Sections 5.7 to suppress pulse reverberation noise and estimate nonlinear scattering, are hence fully applicable to the reconstructed synthetic signals above.

C. Synthetic Dynamic Focusing with Transversal Filter

We choose the z-axis along the beam axis with z=0 at the center of the array aperture. This gives a coordinate representation $\underline{r}=z\underline{e}_z+\underline{r}_\perp=\underline{z}+\underline{r}_\perp$ where $\underline{e}_z$ is the unit vector along the beam axis and $\underline{r}_\perp$ is the coordinate in the plane orthogonal to the z-axis, i.e. $\underline{z}\underline{r}_\perp=0$. The image is obtained by lateral scanning of the beam, where the $1^{st}$ order scattered image signal can from Eq.(23) be modeled as a convolution in the transversal plane $$dY_{l1}(z_i, \underline{r}_\wedge, w) = \qquad (41)$$

$$-dz k^2 V_p(z_i, w) U(w) \int_{Z_i} d^2 r_{\wedge 1} H_b(z, \underline{r}_\wedge - \underline{r}_{\wedge 1}, w) u(z, \underline{r}_{\wedge 1})$$

where $Z_i$ is an interval around $z_i$ of scatterers that all interfere at $z_i$, and $$H_b(z,\underline{r}_{\cdot},w) = H_r(z,\underline{r}_{\cdot},w) \qquad (42)$$

is the composite beam spatial frequency response as defined in detail in Appendix B. We seek a whitening filter in the transversal coordinates with an impulse response w that minimizes the lateral point spread function for each depth z as $$d\hat{Y}_{l1}(z_i, \underline{r}_\wedge, w) = \int d^2 r_{\wedge 2} w(\underline{r}_\wedge - \underline{r}_{\wedge 2}, w; z_i) dY_{l1}(z_i, \underline{r}_{\wedge 2}, w) \qquad (43)$$

$$= -dz k^2 V_p(z_i, w) U(w) \int_{Z_i} d^2 r_{\wedge 1} H_w$$

$$(z, \underline{r}_\wedge - \underline{r}_{\wedge 1}, w; z_i) u(z, \underline{r}_{\wedge 1})$$

where we have defined $$H_w(z,\underline{r}_{\cdot},w;z_i) = \int d^2 r_{\cdot 2} w(\underline{r}_{\cdot} - \underline{r}_{\cdot 2}, w; z_i) H_b(z,\underline{r}_{\cdot 2}, w)$$

$$\tilde{H}_w(z,\underline{k}_{\cdot},w;z_i) = W(\underline{k}_{\cdot},w;z_i) \tilde{H}_b(z,\underline{k}_{\cdot},w) \qquad (44)$$

where the tilde indicates Fourier transform in the transversal coordinate. We can now determine W as a whitening, inverse filter as $$W(\underline{k}_\wedge, w; z_i) = \frac{1}{\tilde{H}_b(z_i, \underline{k}_\wedge, w)} \frac{1}{1 + m_N / |\tilde{H}_b(z_i, \underline{k}_\wedge, w)|^2} \qquad (45)$$

where $m_N$: $10^{-1}$–$10^{-3}$ is a noise parameter that avoids large amplitude gains in W when the amplitude of $|\tilde{H}_b|$ gets low. We note in particular that the following phase relation $$-W(\underline{k}_{\cdot},w;z_i) = -\tilde{H}_b(z_i,\underline{k}_{\cdot},w) \qquad (46)$$

which implies that the whitening filter renders a zero phase $H_w(z_i,\underline{r}_{\cdot},w;z_i)$, that gives the narrowest point spread function at $z_i$ for a given amplitude spectrum, as analyzed in detail in Appendix B. The increased gain of W when $|\tilde{H}_b|$ gets low, reduces the width of the beam main lobe, but increases the side lobes, so there is a point in not making $m_N$ to low. In many situations it can be advantageous to just use the phase filtering as $$W(\underline{k}_{\cdot},w;z_i) = e^{-i-\tilde{H}_b(z_i,\underline{k}_{\cdot},w)} \qquad (47)$$

to avoid raising the side lobes in the filtering process. We hence see that with this method it is possible to obtain a synthetic depth variable focus for the 1st order scattering as in Appendix B. Comparing with Eqs.(26-29) for $3^{rd}$ order scattering we see that when $H_r = H_t$, this statement also holds for the $3^{rd}$ order scattering. To obtain Q=1 it is important that the aperture and apodization are the same for the transmit and receive beams. In the imaging process one can however operate with a dynamic focusing of the receive beam, and use filtered focusing of the transmit beam as described in Appendix B. The transversal filtering in Eqs.(43-47) is two-dimensional, i.e. both in the azimuth and the elevation direction. This requires that we have a 3D data set. However, the methods are directly applicable to transversal filtering only in the azimuth direction of a 2D image. The object must be stationary for the time it requires to cover a scatterer with the whole transmit beam cross section, and there are some practical limitations on the synthetic F-numbers that is possible to achieve, due to lateral sampling density in the image. It can be advantageous to use a couple of depth zones with actual beam foci within each zone, and obtain synthetic depth variable focusing within each zone through transversal filtering as described here.

5.6 Signal Models for Plane Reflectors

A. Structure of Beams and Reflecting Planes

Strong pulse reverberations are generally caused by reflecting layers in front of the object, such as fatty layers in the body wall. Plane layers normal to the array axis can be modeled as $u(\underline{r}) = R(z)$ where z is the coordinate along the beam axis, normal to the fat layers. We continue with reference to FIG. 5 where 500 shows the radiating surface of an ultrasound transducer array. 501 stylistically (i.e. diffraction neglected) shows the geometric boundaries of a transmit beam with transmit aperture $D_t$ (502) and focus at $z_t$. 503 stylistically shows the geometric boundaries of a receive beam with receive aperture $D_r$ (504), and focus at $z_r$. We assume that the receive beam is dynamically focused at the image depth $z_r = ct/2$, where t is the echo arrival time, referred to as the fast time. Slow time is the time-scale on which the object changes, where such changes are observed by repeated transmission of pulse complexes. Due to the dynamic focusing, the receive beam can have a lower F-number $FN_r = z_r/D_r$, than the transmit beam which in this example has a fixed focus and a transmit F-number $FN_t = z_t/D_t$. The Figure shows 4 reflecting planes 505, 506, 507, and 508, at the positions $z_1$, $z_2$, $z_3$, and z with reflection coefficients $R(z_1)$, $R(z_2;w)$, $R(z_3)$, and $R(z)$. As the $2^{nd}$ plane 506 also can be the transducer surface, we have allowed $R(z_2;w)$ to be frequency dependent. We split the coordinates as $\underline{r} = z\underline{e}_z + \underline{r}_{\cdot}$, where $\underline{r}_{\cdot}$ is the transversal coordinate in the planes and z is the coordinate along the beam axis. At each reflection, we integrate the signals $\underline{r}_{\cdot}$ for each plane, where the scattering densities $u(\underline{r}) = R(z)$ and $s_n(\underline{r}) = R_n(z)$ are independent of $\underline{r}_{\cdot}$.

B. Signal Models for $1^{st}$ Order Scattering

With dynamic focusing of the receive beam, the $1^{st}$ order scattering occurs from the plane 508 in the focus of the receive beam. We modify Eq.(23) for the linearly and nonlinearly scattered signals as $$dY_{lp}(w;z,\underline{r}_{\cdot}) = dz\, R(z) U(w) V_p(z,\underline{r}_{\cdot},w;\underline{r}_{t}) ikH_r(z,\underline{r}_{\cdot},w;\underline{r}_{r}) ikH_t(z,\underline{r}_{\cdot},w;\underline{r}_{t}) a)$$

$$dY_{np}(w;z,\underline{r}_{\cdot}) = dz\, 2p_L(z,\underline{r}_{\cdot}) R_n(z) U(w) \cdot V_p(z,\underline{r}_{\cdot},w;\underline{r}_{t}) ikH_r(z,\underline{r}_{\cdot},w;\underline{r}_{r}) ikH_t(z,\underline{r}_{\cdot},w;\underline{r}_{t}) b) \qquad (48)$$

To obtain the signal model for the $1^{st}$ order scattered signal from the plane 508 at $z_r$, we integrate across the transversal coordinate $\underline{r}_{\cdot}$ of the plane. With reference to Eq.(B3) of Appendix B, it is natural to define the following expressions by the transversal integration $$H_{tr}(z, w; \underline{r}_t, \underline{r}_r) = \int_{R^2} d^2 r_\wedge ikH_r(z, \underline{r}_\wedge, w; \underline{r}_r) ikH_t(z, \underline{r}_\wedge, w; \underline{r}_t) \qquad (49)$$

$$= \int_{S_r} d^2 r_4 w_r(\underline{r}_4) H_{abc}(\underline{r}_4, w; \underline{r}_r)$$

$$e^{-iw\tau_r(\underline{r}_4,\underline{r}_r)} ikH_t(2z + \underline{r}_4, w; \underline{r}_t)$$

This expression allows us to write the received $1^{st}$ order scattered signal from a layer at depth z as $$dY_{lp}(w;z)dz = dz\, R(z)U(w)\overline{V}_p(z,w;\underline{r}_t)H_{tr}(z,w;\underline{r}_t,\underline{r}_r)a)$$

$$dY_{np}(w;z)dz = dz\, 2\overline{p}_L(z)R_n(z)U(w)\overline{V}_p(z,w;\underline{r}_t)H_{tr}(z,w;\underline{r}_t,\underline{r}_r)b) \quad (50)$$

where we have defined a) $\overline{V}_p(z,w;\underline{r}_t) = \hat{V}_p(z,w)e^{-iwpt(z)}$ (51)

$$= \frac{\int_{R^2} d^2 r_\wedge V_p(z,r_\wedge,w;\underline{r}_t) \, ikH_r(z,r_\wedge,w;\underline{r}_r)}{H_{tr}(z;\underline{r}_t,\underline{r}_r)} \cdot ikH_t(z_1,r_\wedge,w;\underline{r}_t)$$

b) $\overline{p}_L(z) = \dfrac{\int_{R^2} d^2 r_\wedge p_L(z,r_\wedge)V_p(z,r_\wedge,w;\underline{r}_t)\, ikH_r(z,r_\wedge,w;\underline{r}_r)\, ikH_t(z_1,r_\wedge,w;\underline{r}_t)}{\int_{R^2} d^2 r_\wedge V_p(z,r_\wedge,w;\underline{r}_t)\, ikH_r(z,r_\wedge,w;\underline{r}_r)\, ikH_t(z_1,r_\wedge,w;\underline{r}_t)}$ We note that in the linear material we $V_p=1$ and $R_n=0$. With zero LF pulse in the nonlinear material ($p_L=0$), we will still have an accumulative nonlinear self-distortion of the LF pulse which pumps power from the fundamental HF band into harmonic components of the fundamental HF band. This is seen as a nonlinear attenuation of the fundamental HF-band, that can be included in $V_p$. However, the nonlinear self-scattering is low and found as components in the harmonic bands.

We should note that if the local nonlinear propagation delay $pt(\underline{r})$ varies across the reflector within the receive beam, this variation will produce a LF pressure dependent modification of the pulse form received from the plane, and is in this model included in $\overline{V}_p(z,w)$, while the average of $pt(\underline{r})$ across the receive beam is included in $pt(z)$. This pulse form modification is similar to the LF pressure dependent speckle discussed in Section 5.7A below, with a difference that the plane reflector is not random across the plane. The phenomenon comes in addition to the local pulse form distortion of the transmitted pulses, given by the variation of the LF pulse along the co-propagating HF pulse, accumulated along the pulse propagation path up to $\underline{r}$ and included in $\hat{V}_p(\underline{r},w)$ of Eq.(19). To minimize this pulse form modification from the integrated nonlinear propagation delay, one must design HF and LF beams where the nonlinear propagation delay is close to constant across the HF receive beam focus cross section for each depth z. We should note that it is the magnitude variation of $pt(\underline{r})$ that produces this pulse form modification, not the relative variation. This implies that this pulse form modification increases with depth together with $pt(z)$. Synthetic transmit beam with for example plane wave imaging do here have an advantage, as the variation of the LF pulse transversal to the wave front of the component HF transmit pulse can be made low, and so also the LF beam diffraction with low sliding between the LF phase and HF pulse position with propagation depth.

The fast time representation of the received 1$^{st}$ order scattered signal is found as the inverse Fourier transform of Eq. (50)

$$d y_{lp}(t;z) = dz\, R(z)u(t) \underset{t}{\sim} \hat{v}_p(z, t-p_k t(z)) \underset{t}{\sim} h_{tr}(z, t; z_t, z_r) \quad (52)$$

where each term is the inverse Fourier transform of the corresponding terms in capital letters. In the practical situation there will be strong reflecting planes in the neighborhood of $z_r$. Due to the received pulse length from these planes, a certain thickness $Dz = cT_{pH}/2$ of reflecting planes around $z_r$, will interfere and give a LF pressure dependent speckle in the received signal. $T_{pH}$ is the HF temporal pulse length. The received pulse length is given by the convolved temporal lengths of the u(t), the transmit and receive beam impulse responses $h_{tr}(z,t;\underline{r}_t,\underline{r}_r)$, and the pulse form distortion filter $\hat{v}_p(z,t)$. As we only observe the location of strong reflecting planes, it is convenient to define their positions from the fast time arrival of the signal as $z=ct_1/2$, that gives a) $d y_{l1}(t;t_1) = dt_1 R(t_1)u(t) \underset{t}{\sim} \hat{v}_p(t_1, t-p_k t(t_1)) \underset{t}{\sim} h_{tr}(t_1, t; t_t, t_r)$ (53)

b) $d y_{n1}(t;t_1) =$ $$dt_1 2\overline{p}_L(t_1)R_n(t_1)u(t) \underset{t}{\sim} \hat{v}_p(t_1, t-p_k t(t_1)) \underset{t}{\sim} h_{tr}(t_1, t; t_t, t_r)$$

C. Signal Models for 3$^{rd}$ Order Scattering

For the Class I type pulse reverberation noise, the transmitted pulse is first reflected from the 1$^{st}$ plane 505 at $z_1$, then re-reflected from the 2$^{nd}$ plane 506 at $z_2$ and finally reflected at the 3$^{rd}$ plane 507 at $z_3$ back to the transducer for reception. As we integrate across the planes, $H_{rev}$ will interact with one of the transmit and receive beams, $H_t$ or $H_r$, to provide extended transmit and receive beams mirrored around the plane 2$^{nd}$ reflector. As the effect of the LF pulse on the HF pulse is negligible after the first reflection, it is convenient to extend the receive beam from the 1$^{st}$ reflection and through two more reflections back to the receiver transducers. We then note the following:

For Class I pulse reverberation noise, the receive beam propagates from plane 505 at $z_1$, back to 506 at $z_2$, forward to 507 at $z_3$, and back to the transducer, a total propagation distance of $z_{rec} = z_1 - z_2 + z_3 - z_2 + z_3 = z_1 + 2(z_3 - z_2)$. From FIG. 5 we have $z - z_1 = z_3 - z_2$, where $z = ct/2$, where t is the fast time arrival of the center of the 3$^{rd}$ order scattered pulse. Combed we get $z_{rec} = 2z - z_1$. The total propagation distance for both transmit and receive is $z_1 + z_{rec} = 2z$, i.e. independent of the position of the planes at $z_1$ and $z_2$ because $z_3 = z - (z_1 - z_2)$. The receiver observes the signal reflected from the plane 505 at $z_1 = z - (z_3 - z_2)$ as if it occurs at a plane 509 symmetrically around the dynamic receive focus at position $z_4 = z + (z_3 - z_2) = 2z - z_1$.

For Class II pulse reverberation noise, the receive beam propagates from plane 507 at $z_3$, back to 506 at $z_2$, forward to 505 at $z_1$ and back to the transducer, a total propagation distance of $z_{rec} = z_3 - z_2 + z_1 - z_2 + z_1 = z_3 + 2(z_1 - z_2)$. From above we have $z_1 - z_2 = z - z_3$ which gives $z_{rec} = 2z - z_3$, i.e. the receiver observes the signal reflected from the plane 505 at $z_3 = z - (z_1 - z_2)$ as if it occurs at a plane 510 symmetrically around the dynamic receive focus at position $z_5 = z + (z_1 - z_2)$.

From Eq. (26) we get the following expressions for the Class I and II pulse reverberation noise $$dY_{Ip}(w;z,\underline{r}_1,z_2) = dz_1 dz_2 R(z_1)R(z-(z_1-z_2))U(w)\cdot V_p(z_1,\underline{r}_1,w;\underline{r}_t)ikH_r(2z-z_1,\underline{r}_1,w;\underline{r}_r)ikH_t(z_1,\underline{r}_1,w;\underline{r}_t)a)$$

$$dY_{IIp}(w;z,z_2,\underline{r}_3) = dz_2 dz_3 R(z-(z_3-z_2))R(z_2;w)R(z_3)U(w)\cdot V_p(z_3,\underline{r}_3,w;\underline{r}_t)ikH_r(2z-z_3,\underline{r}_3,w;\underline{r}_r)ikH_t(z_3,\underline{r}_3,w;\underline{r}_t)b) \quad (54)$$

R($z_2$;w) is allowed to be a function of frequency that would occur when the transducer array is the $2^{nd}$ reflector for $z_2$=0. For the transversal integration across the first reflecting plane, the receiver beam is not by far so limiting to max contributing $r_{\wedge j}$, j=1,3, as for the $1^{st}$ order scattering, because $z_1+2(z_3-z_2)=2-z_1$ and $z_3+2(z_1-z_2)=2z-z_3$ is generally far outside the focus of the receive beam as seen in FIG. 5. For the pulse reverberation noise it is therefore not as useful to separate out of the nonlinear manipulation of the HF pulse propagation by the co-propagating LF pulse, as for the $1^{st}$ order scattering in Eqs.(49,50), and we get a different type of averaging for $V_p$. Integration across the transversal coordinate of Eq.(54a,b) then gives the total $3^{rd}$ order pulse reverberation noise as from Appendix B $$dY_{Ip}(w; z, z_1, z_2) = dz_1 dz_2 R(z_1) R(z_2; w) \quad (55)$$
$$R(z - (z_1 - z_2)) U(w) \cdot \overline{V}_p(z, z_1, w; \underline{r}_t) H_{tr}(z, w; \underline{r}_t, \underline{r}_r)$$
$$dY_{IIp}(w; z, z_1, z_2) = dz_1 dz_2 R(z_1) R(z_2; w) R(z - (z_1 - z_2))$$
$$U(w) \cdot \overline{V}_p(z, z - (z_1 - z_2), w; \underline{r}_t) H_{tr}(z, w; \underline{r}_t, \underline{r}_r)$$

$$H_{tr}(z, w; \underline{r}_t, \underline{r}_r) = \int_{R^2} d^2 r_{\wedge j} ikH_r(2z - z_j, \underline{r}_{\wedge j}, w; \underline{r}_r)$$
$$ikH_t(z_j, \underline{r}_{\wedge j}, w; \underline{r}_t)$$

$$j = 1, 3$$

$$\overline{V}_p(z, z_j, w; \underline{r}_t) = \frac{\int_{R^2} d^2 r_{\wedge j} V_p(z_j, \underline{r}_{\wedge j}, w; \underline{r}_t) ikH_r(2z - z_j, \underline{r}_{\wedge j}, w; \underline{r}_r) ikH_t(z_j, \underline{r}_{\wedge j}, w; \underline{r}_t)}{H_{tr}(z; \underline{r}_t, \underline{r}_r)}$$

We note that for a fully linear material, $V_p$=1, and in this case Class I and Class II reverberations are equal for the plane reflectors, even if the transmit and receive beams are different which would make Class I and Class II reverberations different for non-planar reflectors as discussed in relation to Eq. (29). For the nonlinear material, we note as discussed in relation to Eq.(55) that even for zero LF will nonlinear self distortion of the HF pulse produce a nonlinear attenuation of the HF fundamental frequency band, as power is pumped up into harmonic components of the HF band where the absorption is higher. This nonlinear attenuation can be included into a $V_p \neq 1$, also for zero LF.

Summing over the planes along the whole depth down to $z_1$=z, we can include Class I-III reverberations into the following integral $$N(w, z; p) = N_I(w, z; p) + N_{II}(w, z; p) = \tilde{N}(w, z; p) e^{-iwpt_n(z)} = \quad (56)$$
$$U(w) H_{tr}(z, w; \underline{r}_t, \underline{r}_r) \int_0^z dz_1 R(z, z_1; w) \overline{V}_p(z, z_1, w; \underline{r}_t)$$
$$R(z, z_1; w) = \int_0^{z_1} dz_2 \int_{z-(z_1-z_2)-Z_{pH}/2}^{z-(z_1-z_2)+Z_{pH}/2} dz_3 R(z_1) R(z_2; w) R(z_3)$$

where $Z_{pH}(z)$ is the spatial pulse length of the received HF pulse from depth z. Class III noise is obtained when $z_3=z_1$ in the integral. We shall use these expressions as a basis for model based estimation of correction delays and speckle corrections in Section 5.8C.

From Eqs. (49,53,55,56) we get the total HF receive signal in and interval $T_i \sim T_{pH}(t_i)$ around the fast time $t_i=2z_i/c$, where $T_{pH}(t_i)$ is the temporal pulse length of the received HF pulse at $t_i$, as $$Y_i(w;p) = e^{-iwpt(t_i)} \hat{V}_{pi}(w;t_i) X_{li}(w) + e^{-iwpt(t_i)} \hat{V}_{ni}(w;t_i) X_{ni}(w;p) + e^{-iwpt_{ni}} \hat{N}_i(w;p) \quad (57)$$

where $\hat{N}_i(w;p) = \tilde{N}(w, ct_i/2;p)$, $pt_{ni} = pt_n(ct_i/2)$, $X_{li}$ is the linearly scattered signal and $X_{ni}$ is the nonlinearly scattered signal that is given with the general nonlinear dependency on p that includes nonlinear scattering from resonant scatterers like acoustic micro bubbles. For parametric nonlinear scattering, as ultrasound scattering from fluids and tissue, we can approximate $X_{ni}(w;p) \gg pX_{ni}(w)$. $\hat{V}_{pi}$ and $\hat{V}_{ni}$ are the average pulse form distortion across the HF receive beam defined in Eq.(51). For non-resonant scatterers we have $\hat{V}_{ni} \gg \hat{V}_{pi}$.

5.7 Challenges and Methods for Suppression of Multiple or Linear Scattering

A. Delay and Speckle for $1^{st}$ Order Scattering

Eqs.(23, 36,43) gives signal models for $1^{st}$ order scattering from a point scatterer $u(\underline{r}_1)d^3 r_1$, freely positioned in 3D space at $\underline{r}_1$. In this situation Eq.(25) shows how the linear scattering components can be suppressed to enhance the signal from the nonlinear scattering at $\underline{r}_1$, assuming the nonlinear pulse distortion filter $V_p$ is known. However, we do generally have a distribution of scatterers which complicates the suppression of the linear scattering. The HF receive signal is picked up versus fast time t, where the depth coordinate in the image along the receive beam axis is calculated as z=ct/2.

The $1^{st}$ order HF receive signal at each fast time point t=2z/c is generally composed of several overlapping radio frequency (RF) HF pulses from different scatterers that interfere with each other. We define $R_1(t)$ as the region of scatterers $\underline{r}_1$. $R_1(t)$ that produces $1^{st}$ order scattered HF receive pulses that overlap at the fast time t. These HF receive pulses interfere both constructively and destructively, depending on the relative arrival time of the individual HF pulses, which results in a fairly random variation of the HF signal envelope, which we refer to as speckle.

The variation of the HF receive signal with the LF pulse, can hence be separated into two components:

i) An average nonlinear propagation delay pt(t) for the HF receive signal at fast time t that is a weighted average of the nonlinear propagation delays $pt(\underline{r}_1)$ for all HF receive pulses from scatterers at $\underline{r}_1$. $R_1(t)$ that overlap and interfere at fast time t. This average, local nonlinear propagation delay can for example be estimated through correlation techniques between the $1^{st}$ order HF receive signal for a transmitted pulse complex with zero LF pulse and the $1^{st}$ order HF receive signal for a transmitted pulse complex with the actual transmitted LF pulse.

ii) A variation in the speckle of the $1^{st}$ order HF receive signal due to variations in the LF pulse. This $1^{st}$ order speckle varies due to the LF pulse through two physical effects:

iia) The nonlinear pulse form distortion produced by variations in the LF pulse along the co-propagating HF pulse changes the HF pulses with the LF pulse, and hence also the interference between the HF pulses that overlap in time. This effect makes the HF receive signal speckle vary with the LF pulse, and the effect is contained in $\hat{V}_p$.

iib) Spatial variations in the local nonlinear propagation delay $pt(\underline{r}_1)$ over $\underline{r}_1$. $R_1(t)$, will result in a variation in the interference between the different overlapping pulses that will depend on the LF pulse. This interference has a random nature because of the random nature of the scattering cross section and the position of the scatterers at $\underline{r}_1$. We can however operate with an average dependency that can be included in $\hat{V}_p$, but the random variation around this average value is difficult to correct for in the image reconstruction. We should note that it is the magnitude of the variation in $pt(\underline{r}_1)$ that produces the effect, not the relative variation, and as $pt(\underline{r}_1)$ accumulates with depth according to Eq.(18), the effect generally increases with depth. The dependency of $pt(\underline{r}_1)$ on the LF pulse, is conveniently further broken down into two components:

iiba) Variation of $pt(\underline{r}_1)$ along the HF receive beam direction, which we call an axial variation. This variation is inherent in the method where $pt(\underline{r}_1)$ from Eq.(18) is obtained by accumulation along the paths of energy flow (orthogonal trajectories) of the transmit beam. To reduce the LF dependency of the interference due to the axial variation of $pt(\underline{r}_1)$, we should use as short HF transmit pulses as possible, i.e. wide HF bandwidth.

iibd) Variation of $pt(\underline{r}_1)$ transverse to the HF receive beam at the depth $z=ct/2$ we call a transverse variation. The transverse variation depends on the detailed design (aperture and focus) of the combined LF and HF transmit beams, and can be minimized by good beam designs. The sensitivity to this variation can further be reduced by a narrow HF receive beam, which is achieved by a wide HF receive aperture, i.e. low HF receive F-number, and dynamic focus of the HF receive beam. This can make the HF receive beam different from the HF transmit beam, for which we often want a long focus which requires a smaller HF transmit aperture with higher F-number. The combination of low F-number HF receive beam and higher F-number HF transmit beam makes $Q>1$ in Eqs.(29,30), which we shall see gives challenges for good suppression of pulse reverberation noise and/or linear scattering as we return to in Section 5.7C below.

For the plane wave reflections presented in Section 5.6, the variation of the scatterers transverse to the receive beam axis is not random but well defined in the definition of the planes. The transverse variation of both $pt(\underline{r}_1)$ and $\hat{V}_p(\underline{r}_1,w)$ across the receive beam is then included in the deterministic versions of $pt(z)$ and $\hat{V}_p(z,w)$. Axial variations of $pt(z)$ and $\hat{V}_p(z,w)$ along the HF receive pulses that overlaps at fast time $t=2z/c$, can still contribute to an LF pulse variation of the HF receive signal speckle as discussed under point iiba) above.

B. Delay and Speckle for $3^{rd}$ Order Scattering

The $3^{rd}$ order scattering noise at fast time t, occurs through a sequence of scatterings at the three locations $\underline{r}_1,\underline{r}_2,\underline{r}_3$. $R_3(t)$, defined so that the HF receive pulses from this sequence of scatterings overlap at the fast time t. This implies that the total propagation lag from the HF transmit transducer to $\underline{r}_1$, from $\underline{r}_1$ to $\underline{r}_2$, from $\underline{r}_2$ to $\underline{r}_3$, and from $\underline{r}_3$ back to the HF receive transducer, is so close to t that the HF receive pulses for $\underline{r}_1,\underline{r}_2,\underline{r}_3$. $R_3(t)$ overlap. The relationship between the fast time reception and the scatterer positions is hence more complex for $3^{rd}$ order scattering noise compared to the $1^{st}$ order scattering signal. We note that the HF receive noise pulse lengths are given by a convolution between the transmitted HF pulse length, the length of the HF transmit and receive beam impulse responses, and the length of the HF transducer receive impulse response.

The width of the HF receive beam is for $3^{rd}$ order scattering much less limiting to the region of interfering scatterers than for $1^{st}$ order scattering, where the example in FIG. 5 can be used for understanding this statement. The receive beam focus is generally deeper than the last scatterer in the $3^{rd}$ order chain, because $|\underline{r}_3|<ct/2=z_r(t)$, where $z_r(t)$ is the dynamic receive beam focus located at the depth of the $1^{st}$ order scatterers from which the pulses are received at fast time t. For Class I noise where the $1^{st}$ scatterer is at the position $\underline{r}_1$ where $|\underline{r}_1|<z_r(t)/2=ct/4$, the receive beam has generally so weak limitation to the region of $1^{st}$ scatterers that participates to the Class I noise, that scatterers at $\underline{r}_1$ across the whole transmit beam generally participates in the $3^{rd}$ order chain of scatterers $\underline{r}_1,\underline{r}_2,\underline{r}_3$, $R_3(t)$. For Class II noise where $z_r(t)/2<|\underline{r}_3|<z_r(t)$, the receive beam also generally has a weak limitation to the positions of $1^{st}$ scatterers within the transmit beam at $\underline{r}_3$, albeit the limitation can be stronger than for Class I scatterers, as seen from FIG. 5.

To dwell further into these complex relations, we start by analysis of the situation for $Q=\tilde{V}_p=1$. From Eq. (30) we get $$K_p(w;\underline{r}_1,\underline{r}_3)=e^{-iwp(t(\underline{r}_1)+t(\underline{r}_3))/2}\tilde{K}_p(w;\underline{r}_1,\underline{r}_3)$$

$$\tilde{K}_p(w;\underline{r}_1,\underline{r}_3)=2\cos wp(t(\underline{r}_3)-t(\underline{r}_1))/2 \quad (58)$$

i.e. the filter $K_p(w;\underline{r}_1,\underline{r}_3)$ represents a nonlinear propagation delay of $p(t(\underline{r}_1)+t(\underline{r}_3))/2$ for Class I and II noise combined, with a filtering of the noise amplitude by $\tilde{K}_p$. This amplitude filtering represents the speckle dependency of the $3^{rd}$ order Class I and II noise on the amplitude of the LF pulse. We note that in this special situation of $Q=\tilde{V}_p=1$ and only two point scatterers at $\underline{r}_1$ and $\underline{r}_3$, the combined Class I and II noise speckle is independent of a change in polarity of the LF pulse, as $\tilde{K}_p$ is unchanged by a change in polarity of p. This phenomenon can be utilized for combined suppression of Class I and II noise as discussed in relation to Eq. (62) below.

The reason for the reverberation noise speckle dependency on the LF pulse, is that the noise is composed of two components from $\underline{r}_1$ and $\underline{r}_3$ with different nonlinear propagation delays $pt(\underline{r}_1)$ and $pt(\underline{r}_3)$ that depend on both the amplitude and polarity of the LF pulse. This represents a spatial variation of the nonlinear propagation delay similar to that discussed for 1st order scattering under point iib) of Section 5.7A above. However, for the $3^{rd}$ order scattering we are not only considering a variation of $pt(\underline{r}_1)$ along the HF receive pulse length and the width of the highly focused HF receive beam, but for a larger region of allowable $\underline{r}_1$ and $\underline{r}_3$ that satisfies $\underline{r}_1,\underline{r}_2,\underline{r}_3$, $R_3(t)$.

When $Q(\underline{r}_1,\underline{r}_3)\tilde{V}_p(\underline{r}_1)_n\tilde{V}_p(\underline{r}_3)$, where in the practical situation we find $|Q(\underline{r}_1,\underline{r}_3)\tilde{V}_p(\underline{r}_1)|>|\tilde{V}_p(\underline{r}_3)|$, $\tilde{K}_p$ from Eq.(30) has a nonzero phase as shown in FIG. 7a. This phase can be separated into a component that is linear in frequency, producing an added nonlinear propagation delay to $p(t(\underline{r}_1)+t(\underline{r}_3)/2$, and a component that is nonlinear in frequency that together with the amplitude variation of $|\tilde{K}_p|$ with frequency produces a LF pulse dependency of the combined Class I and II noise speckle. The reason for the delay component of $\tilde{K}_p$ is that the Class I noise is now stronger than the Class II noise, making the average nonlinear propagation delay closer to $pt(\underline{r}_1)$ than to $pt(\underline{r}_3)$, reducing the average delay/advancement because $|pt(\underline{r}_1)|<|pt(\underline{r}_3)|$. FIG. 7b shows in the temporal domain how a change in polarity of the LF pulse changes the relative location between the Class I and II reverberation pulses, changing the speckle as the interference between the two pulses when the Class II noise pulse is lower in amplitude than the Class I pulse, i.e. $|Q|>1$. The average nonlinear propagation delay is closer to that for Class I pulse due to its larger amplitude. We note that if the Class I and II components were equal, the noise speckle would be independent of the polarity of the LF pulse, and the average nonlinear propagation delay would be $pt(\underline{r}_1)+t(\underline{r}_3))/2$. This implies that when $\underline{r}_1$ and $\underline{r}_3$ move close to the mid distance $r/2=ct/4$ of the image point, we get $QV_{p1}>>V_{p3}$, i.e. $dY_{Ip}>>dY_{IIp}$, and the speckle dependency on the LF pulse polarity is low for scatterers in this mid region.

The Fourier transform of the total pulse reverberation noise in an interval of length $T_i$ around $t_i$, can be expressed as $$Y_{3i}(w, p) = \sum_{m,M_{3i}} dY_{ill,m} e^{-iwp(t_{1m}+t_{3m})/2} 2\cos wp(t_{3m}-t_{1m})/2 \quad (59)$$

where $M_{3i}$ labels the group of combinations of scatterers at $\underline{r}_{1m},\underline{r}_{2m},\underline{r}_{3m}, R_3(t_i)$ that contributes to the Class I+II noise in $T_i$. This expression is no longer in general independent of a change in polarity of the LF pulse. Introducing the fast time arrival of the signals, we can rewrite Eq.(59) as $$N_i(w, p) = \sum_{m,M_{3i}} dN_{ill,m} e^{-iwp(t(t_{1m})+t(t_{3m}))/2} 2\cos wp(t(t_{3m})-t(t_{1m}))/2 \quad (60)$$

For the transducer as the main $2^{nd}$ reflector, we have $t_2=0$ and $t_3=t-t_1$. With a nonlinear propagation delay that is linear in the fast time as $t(t)=at$, we get $$(t(t_3)+t(t_1))/2 = a(t-t_1+t_1)/2 = at/2 = t(t)/2 \; a$$

$$(t(t_3)-t(t_1))/2 = a(t-t_1-t_1)/2 = a(t-2t_1)/2 = t(t)/2 - t(t_1) \; b \quad (61)$$

i.e. the delay of the combined Class I and II pulse reverberation noise is independent of the location of plane 505 at $t_1$ and plane 507 at $t_3=t-t_1$. Eq.(60) now changes to $$N_i(w, p) = e^{-iwpt(t_i)/2} \sum_{m,M_i} dN_{ill,m}(w) 2\cos wp(t(t_i)-2t(t_{1m}))/2 \quad (62)$$

The basis for this equation is that $Q=\tilde{V}_p=1$, $t_2=0$, and a linear variation of $t(t)$ with fast time $t$. $Q\approx 1$ is obtained with plane reflectors as discussed in Section 5.6, and can be achieved for more irregular scatterers with equal transmit and receive beams. To obtain image sharpness in a depth range with equal transmit and receive beams requires multi-focus transmissions which reduces frame rate, or one can use transversal filtering as described in Section 5.5C, or a combination of both, or multi-component transmissions with synthetic transmit and receive beams reconstruction as described in Section 5.5A, B. In this last case it is easier to avoid pulse form distortion, i.e. we get $\tilde{V}_p\gg 1$, as the diffraction sliding of the unfocused LF pulse component is low, and we can place the HF pulse close to the crest or trough of the LF pulse for the whole image range.

It can also in some situation be advantageous to select a region of the LF aperture to be non-transmitting, so that manipulation of the object material parameters by the LF pulse observed by the co-propagating HF pulse is very low in a near field region of the HF array aperture, for example as described in U.S. Patent application 12/500,518. Delay corrections or speckle corrections are then not necessary for suppression of the multiple scattering noise components where the scatterers are in this near-field range. One can then concentrate on estimation of delay corrections or speckle corrections for scatterers that are outside this near field range.

For the $3^{rd}$ order Class I and II scattering we then conclude:

i) The average nonlinear propagation delay for combined Class I and II noise is more dependent on spatial variations in the nonlinear propagation delay $pt(\underline{r})$ compared to $1^{st}$ order scattering, as we at fast time t get overlapping contributions of scattered signal for a wider range of scatterer locations $\underline{r}_1$ and $\underline{r}_3$ that satisfies $\underline{r}_1,\underline{r}_2,\underline{r}_3, R_3(t)$. However, for a linear variation of the nonlinear propagation delay with fast time, $t_2=0$, and $Q=\tilde{V}_p=1$, the combined Class I and II noise gets an average nonlinear propagation delay equal to $pt_n(t)=pt(t)/2$, and the noise speckle is independent of a change in polarity of the LF pulse. This can through Eq. (62) be used to suppress combined Class I and II noise as in Eq.(67,68) below.

When the variation of the nonlinear propagation delay with the fast time deviates from linear variation in t, we get $pt_n(t) \neq pt(t)/2$. For a variation with fast time that is upwards convex, which is often found, the average nonlinear propagation delay for the combined Class I and II noise is $pt_n(t)<pt(t)/2$ as illustrated in FIG. 8. The speckle is in this case no longer independent of the polarity of the LF pulse, even for $\overline{Q}=\tilde{V}_p=1$.

When $|Q(\underline{r}_1,\underline{r}_3)\tilde{V}_p(\underline{r}_1)|>|\tilde{V}_p(\underline{r}_3)|$ we get a non-zero phase of $\tilde{K}_p$ as illustrated in FIG. 7a. The component of this phase that is linear in frequency produces a nonlinear propagation delay added to $p(t(\underline{r}_1)+t(\underline{r}_3))/2$, that depends both on the amplitude and the polarity of the LF pulse. The combined Class I and II noise delay is an average of $pt(\underline{r}_1)$ and $pt(\underline{r}_3)$, weighted with the amplitude of the Class I and Class II noise components at the different scatterer locations $\underline{r}_1$ and $\underline{r}_3$ that contribute to the composite noise in an interval, i.e. $\underline{r}_1,\underline{r}_2,\underline{r}_3, R_3(t)$. When $|Q(\underline{r}_1,\underline{r}_3)\tilde{V}_p(\underline{r}_1)|>|\tilde{V}_p(\underline{r}_3)|$ we get stronger weight on $pt(\underline{r}_1)$ than $pt(\underline{r}_3)$, reducing the average nonlinear propagation delay below $p(t(\underline{r}_1)+t(\underline{r}_3))/2$, i.e. $pt_n(t)<pt(t)/2$.

ii) The combined Class I and II noise speckle has a larger sensitivity to variation in the LF pulse than the $1^{st}$ order scattering signal. This variation can be related to two different physical effects:

iia) At fast time t we get overlapping contributions of scattered signal for a wide range of scatterer locations $\underline{r}_1$ and $\underline{r}_3$ that satisfies $\underline{r}_1,\underline{r}_2,\underline{r}_3, R_3(t)$. These different scatterer locations have different nonlinear propagation delays $pt(\underline{r}_1)$ and $pt(\underline{r}_3)$ that depends on the amplitude and polarity of the LF pulse and hence produces a larger sensitivity to LF pulse changes for the combined Class I and II noise speckle compared to the $1^{st}$ order scattering speckle. When $\overline{Q}=\hat{V}_p=1$, $t_2=0$, and a linear variation in the nonlinear propagation delay with fast time, the combined Class I and II noise speckle do not change with the polarity of the LF pulse, albeit it depends on the amplitude of the LF pulse.

iib) The nonlinear pulse form distortion of the transmitted HF pulse, produced by variations of the LF pressure along the co-propagating HF pulse and given by $\tilde{V}_p$ in Eqs.(19, 29, 30), changes the HF pulses that interfere at a fast time t, and hence also the interference speckle. The pulse form distortion is given by the nonlinear phase component of $\tilde{V}_p$ in and also the spectral amplitude modification by $|\tilde{V}_p|$, and depends on both the amplitude and the polarity of the LF pulse.

C. Estimation of Linear and Nonlinear Scattering Components with Noise Suppression Based on the HF receive signal model in Eq.(57), we study the following set of equations obtained as the HF receive signal from transmission of three pulse complexes with amplitude +p, 0, −p of the LF pulse $$Y_i(w;p) = e^{-iwpt_i}\{\hat{V}_{pl}(w;t_i)X_{li}(w)+p\hat{V}_{pn}(w;t_i)X_{ni}(w)\} + e^{-iwpt_{ni}}\hat{N}_i(w;p) \; a)$$

$$Y_i(w;0) = X_{li}(w)+N_i(w;0) \; b)$$

$$Y_i(w;-p) = e^{iwpt_i}\{\hat{V}_{-pl}(w;t_i)X_{li}(w)- p\hat{V}_{-pn}(w;t_i)X_{ni}(w)\}+e^{iwpt_{ni}}\hat{N}_i(w;-p) \; c) \quad (63)$$

where we have made the approximation $X_{ni}(w;p) \gg pX_{ni}(w)$ for the nonlinear scattering. In the same token we generally have $\hat{V}_{pn}(w;t_i)=\hat{V}_{pl}(w;t_i)$ except in situations of strong, resonant nonlinear scattering. We have here three linear equations with the five unknowns $X_{li}(w)$, $X_{ni}(w)$, $\hat{N}_i(w;p)$, $N_i(w;0)$ and $\hat{N}_i(w;-p)$. We can relate $\hat{N}_i(w;p)$ to $N_i(w;0)$ by the following filter $$N_i(w; 0) = M_i(w; p)\hat{N}_i(w; p) \quad (64)$$

$$M_i(w; p) = \frac{N_i(w; 0)}{\hat{N}_i(w; p)} \frac{1}{1 + m_N |N_i(w; 0)/\hat{N}_i(w; p)|^2} = \hat{M}_i(w; p)e^{iwpt_{ni}}$$

where $m_N : 10^{-3} - 10^{-2}$ is a noise parameter. Delay correction and filtering according to Eq.(63) and combination of Eqs.(63a,b) and Eqs.(63b,c) gives us two equations with noise highly suppressed $$a_{11}X_{li}(w) + a_{12}X_{ni}(w) = b_1$$

$$a_{21}X_{li}(w) + a_{22}X_{ni}(w) = b_2$$

$$a_{11} = e^{iwp(t_{ni} - t_i)}\hat{M}_i(w; p)\hat{V}_{pl}(w; t_i) - 1$$

$$a_{21} = e^{-iwp(t_{ni} - t_i)}\hat{M}_i(w; -p)\hat{V}_{pl}(w; t_i) - 1$$

$$a_{12} = pe^{iwp(t_{ni} - t_i)}\hat{M}_i(w; p)\hat{V}_{pn}(w; t_i)$$

$$a_{22} = -pe^{-iwp(t_{ni} - t_i)}\hat{M}_i(w; -p)\hat{V}_{-pn}(w; t_i)$$

$$b_1 = \hat{M}_i(w; p)e^{iwp(t_{ni} - t_i)}Y_i(w; p) - Y_i(w; 0)$$

$$b_2 = \hat{M}_i(w; -p)e^{-iwp(t_{ni} - t_i)}Y_i(w; -p) - Y_i(w; 0) \quad (65)$$

with the solution for the linear and nonlinear scattering $$\text{a)} \quad X_{li}(w) = \frac{a_{22}b_1 - a_{12}b_2}{a_{11}a_{22} - a_{12}a_{21}} \quad (66)$$

$$\text{b)} \quad X_{ni}(w) = \frac{-a_{21}b_1 - a_{11}b_2}{a_{11}a_{22} - a_{12}a_{21}}$$

Even if we can not make the approximation $X_{ni}(w; p) \gg pX_{ni}(w)$, Eq. (66b) gives a signal where both the noise and the linear scattering is highly suppressed, and hence represents a nonlinear scattering estimate. As the linear scattering is generally much stronger than the nonlinear scattering, Eq. (66a) is an estimate for the linear scattering with noise suppressed, or we could alternatively use the approximate estimate in Eq.(68) below for the linear scattering.

The nonlinear scattering term is generally low relative to the linear scattering term in Eq.(63) and can be neglected to estimate the linear scattering term with strong suppression of Class I and II pulse reverberation noise. We then get the starting equations as $$Y_i(w; p) = e^{-iwpt_i}\hat{V}_{pl}(w; t_i)X_{li}(w) + e^{iwpt_{ni}}\hat{N}_i(w; p)a)$$

$$Y_i(w; -p) = e^{iwpt_i}\hat{V}_{-pl}(w; t_i)X_{li}(w) + e^{iwpt_{ni}}\hat{N}_i(w; -p)b) \quad (67)$$

Delay correcting and filtering as in Eqs. (62-65) we get $$X_{li}(w) = \frac{e^{iwpt_{ni}}\hat{M}_i(w; p)Y_i(w; p) - e^{-iwpt_{ni}}\hat{M}_i(w; -p)Y_i(w; -p)}{e^{iwp(t_{ni} - t_i)}\hat{M}_i(w; p)\hat{V}_{pl}(w; t_i) - e^{-iwp(t_{ni} - t_i)}\hat{M}_i(w; -p)\hat{V}_{-pl}(w; t_i)} \quad (68)$$

When the noise speckle is independent of the polarity of the LF pulse, we can obtain a linear scattering signal with strong suppression of the $3^{rd}$ order scattering noise through only delay correction of Eqs. (67a,b) (i.e. no speckle corrections) and subtracting as $$Z_i(w) = e^{iwp\hat{t}_{ni}}Y_i(w; p) - e^{-iwp\hat{t}_{ni}}Y_i(w; -p) = \quad (69)$$

$$\left[ e^{-iwp(t_i - \hat{t}_{ni})}\hat{V}_{pl}(w; t_i) - e^{iwp(t_i - \hat{t}_{ni})}\hat{V}_{-pl}(w; t_i) \right]$$

$$X_{li}(w) + \left[ e^{-iwp_1(t_{ni} - \hat{t}_{ni})}\hat{N}_i(w; p) - e^{iwp(t_{ni} - \hat{t}_{ni})}\hat{N}_i(w; -p) \right]$$

We see from Eq. (62) above that for $\overline{Q} = \hat{V}_p = 1$ and a linear depth dependency of the non-linear propagation delay, the speckle of combined Class I and II pulse reverberation noise is independent on the polarity of the LF pulse, i.e. $\hat{N}_i(w; -p) = \hat{N}_i(w; p)m$, and $t_{ni} = t(t_i)/2$. Limited suppression of the noise in the last term in Eq.(69) is caused by improper estimation of $t_{ni}$, i.e. $\hat{t}_{ni} \cdot t_{ni}$, and variations in the speckle of combined Class I and II pulse reverberation noise with the polarity of the LF pulse, i.e. $\hat{N}_i(w; -p) \cdot \hat{N}_i(w; p)$. If the nonlinear propagation delay deviates from being linear in the fast time t, we can not take the delay term outside the sum in Eq. (62), and the signal speckle is no longer independent of the polarity of the LF pulse. In addition, if any of Q or $V^\%_p \cdot 1$, the signal speckle will be highly dependent on both the amplitude and the polarity of the LF pulse, which further reduces the suppression of the noise term in Eq.(69).

The limitation of noise suppression produced by variations in the noise speckle with the polarity of the LF pulse can be reduced in a low echogene region, for example a cyst or a blood vessel, using the following algorithm $$Z_i(w) = e^{iwp\hat{t}_i}Y_i(w; p) - e^{iwp\hat{t}_{ni}}Y_i(w; p) = \Big[ \quad (70)$$

$$e^{-iwp(t_i - \hat{t}_i)}\hat{V}_{pl}(w; t_i) - e^{-iwp(t_i - \hat{t}_{ni})}\hat{V}_{pl}(w; t_i) \Big]X_{li}(w) + \Big[$$

$$e^{-iwp(t_{ni} - \hat{t}_i)}\hat{N}_i(w; p) - e^{-iwp(t_{ni} - \hat{t}_{ni})}\hat{N}_i(w; p) \Big]$$

Inside the cyst we have $X_{li}(w) = 0$ and $\hat{t}_{ni} \gg t_{ni} \gg t_i \gg \hat{t}_i$ so that the last term, i.e. the noise term, disappears because the speckle, $\hat{N}_i(w; p_1)$, is the same for both components of the noise term. Outside the cyst we have $X_{li}(w) \cdot 0$ and $\hat{t}_{ni} \gg t_i/2$ so that the $1^{st}$ term is non-zero.

By the comments following Eq.(86) below we note that we can obtain some correction for the pulse form distortion by reduction of the bandwidth of the received HF signal through band pass filtering. This band pass filtering provides corrections of the effects of pulse form distortion both on the $1^{st}$ order and multiple order scattering signals.

The signals with strong suppression of multiple scattering noise are also very useful for estimations of corrections for wave front aberrations due to heterogeneous spatial variation of propagation velocity in the material, for example according to the methods described in U.S. Pat. Nos. 6,485,423 and 6,905,465.

D. Limitations in Suppression Due to Delay and Speckle Uncertainty

In Eqs.(66,68) we have compensated for both the nonlinear propagation delay, pulse form distortion, and the LF pulse dependency of the combined Class I and II noise speckle. The success of the suppression of the combined Class I and Class II noise and the linear scattering depends on how accurately we can estimate $t(t_i)$ $\hat{V}_{pl}(w; t_i)$, $t_{ni}$, and $\hat{M}_i(w; p)$. If nonlinear pulse form distortion is negligible we can avoid estimating the full $\nabla_{pi}(w; t_i)$ and only its linear phase components that gives the nonlinear propagation delay $t(t_i)$.

In Eq.(69) we do not compensate for potential variations in the combined Class I and II noise speckle with a change in polarity of the LF pulse. As shown in Section 5.7B, this is achieved for a linear variation of the nonlinear propagation delay with fast time, $t_2=0$, and $\bar{Q}=\hat{V}_p=1$. Deviations from these requirements will reduce the suppression of the $3^{rd}$ order scattering noise in Eq.(69).

In Eq.(70) there is a single noise term where the nonlinear propagation delay and noise speckle is unchanged for the two signals which are combined. The degree of suppression of the pulse reverberation noise does in this expression only depend on the accuracy of the estimate of $\hat{t}_{ni}$. However, if we have $1^{st}$ order scattering signals together with the combined Class I and II pulse reverberation noise, where the $1^{st}$ order signals are much weaker than the noise, the $1^{st}$ order signal will be suppressed together with the noise.

Limited suppression of combined Class I and II noise and also linear scattering components to obtain nonlinear scattering components, including remedies to enhance the suppression, is hence in more detail:

i) Improper estimation of $t_{ni}$ for example through using $\hat{t}_{ni}=t_i/2$ from Eq.(61a). Reasons for fallacy of this estimate can be that ia) $-\tilde{K}_{pi}$ of Eq.(30) depends on the magnitude/polarity of p, for example because Q>1 or $V_1>V_3$. Q>1 implies that Class II reverberations has lower amplitude than Class I reverberations, as illustrated in FIG. 7 where FIG. 7a shows an example in the frequency domain that this situation provides $-\tilde{K}_{pi}=-(Q_i\tilde{V}_{pi1}e^{iwp(t_3-t_1)}+\tilde{V}_{pi3}e^{-iwp(t_3-t_1)}),0$ even with $\tilde{V}_{pi1,3}=1$. The same situation is illustrated in the time domain in FIG. 7b, showing that the Class I and II reverberations have different relation to each other for p>0 (mid panel) and p<0 (lower panel). The nonlinear attenuation of the HF pulse due to self-distortion increases this phenomenon because it gives $|\tilde{V}_{pi3}|<|\tilde{V}_{pi1}|$.

A $1^{st}$ remedy to solve this situation is to design the transmit and receive beams of close to the same form so that $-\tilde{K}_{pi}>>0$. Sharpness through a depth region of the image can be obtained for each image line by multiple transmits with different transmit/receive foci, which reduces the frame rate, or transversal filtering as described in Section 5.5C. Another solution is to use multiple, wide transmit beam components with synthetic transmit and receive beams as described in Section 5.5A,B. A $2^{nd}$ remedy is to use a model based estimation of $\hat{t}_{ni}$, for example as given in Section 5.8 below.

We note that when $t_1$ approaches $t_3$ because $t_1$ approaches $(t_i+t_2/2$, we generally get $Q\approx 1$ and $\tilde{V}_{pi1}>>\tilde{V}_{pi3}$. This implies good suppression of the noise term in Eq. (68) as $t_1$ approaches $t_3$ with delay correction with $\hat{t}_{ni}=t_i/2$ for $t(t)>>at$, i.e. the nonlinear propagation delay is linear in t.

ib) Nonlinear depth variation of t(t) as illustrated in FIG. 8 implies that $\hat{t}_{ni}\neq t_i/2$. A $1^{st}$ remedy to solve this situation is to design the HF and LF beams so that adequate linearity of t(t) is obtained. A $2^{nd}$ remedy is to use a model based estimation of $\hat{t}_{ni}$, for example as given in Section 5.8 below, which is also useful for the situation in ia) above. To only use delay correction $\hat{t}_{ni}=t_i/2$ requires both that $-\tilde{K}_{pi}>>0$ as discussed above, and model based estimation of $t_{ni}$ hence solves both these situations.

ii) Variation in noise speckle with the LF pulse. This variation has three reasons:

iia) Spatial variation of the nonlinear propagation delay of the HF pulse over the cross section of the HF transmit beam at $t_1$ and $t_3$. A remedy to improve this situation is to design HF and LF beams so that one gets minimal variation of the nonlinear propagation delay of the HF pulse over the cross section of the HF transmit beam at $t_1$ and $t_3$.

iib) Class I and II pulse reverberation noise is different which implies Q and |V|..1, similar to the illustration in FIG.

7. A remedy to solve this situation is to use the same transmit and receive beam with multiple transmits at different focus depths for each image line or transversal filtering as described in Section 5.5C, or a combination of both, or use synthetic transmit and receive beams as discussed in Section 5.5A, B above.

iic) Nonlinear pulse form distortion as given by a frequency dependency of the module and phase of $\tilde{V}_{pi}$. With synthetic transmit beams one have less sliding of the LF pulse phase because the full image depth is within the near field of the transmit beam components. One can then keep the HF pulse at the crest or trough of the LF pulse for the full image depth.

Remedies for best suppression of the combined Class I and II pulse reverberation noise and also $1^{st}$ order linear scattering components are hence:

A) Design HF and LF transmit apertures and foci so that one gets as linear variation with fast time t as possible of the nonlinear propagation delay, and B) Use equal HF transmit and receive apertures and foci, either through using multi-focus transmits for each image line, or synthetic focusing in a large group of image points as described in Section 5.5, and C) Use model based estimation of $t(t_i)\hat{V}_{pi}(w;t_i)$, $t_{ni}$, and $\hat{M}_i(w;p)$, for example as presented in the next section.

5.8 Model Based Estimation of Delay and Speckle Corrections

A. Simulation Model for Wave Propagation

When the nonlinear propagation delay is not linear in the fast time, and/or $t_2>0$, and/or Q>1, and/or one have disturbing nonlinear pulse form distortion $V_{pi}(w;\underline{r}),0$, improved methods of estimating $t_i$, $t_{ni}$, $V_{pi}(w;\underline{r})$, and $W_i(w;p)$ are needed. For given material parameters we simulate the 3D expressions for $H_i(\underline{r}_1,w;\underline{r}_t)$ in Eq.(1), $H_r(\underline{r}_3,w;\underline{r}_r)$ in Eq.(4), $U_p(\underline{r}_1,w;\underline{r}_t)$ in Eq.(22), $V_p(w;\underline{r})$ and $pt(\underline{r})$ in Eqs.(18,19). Integrating these 3D expressions across a transversal plane in (x,y) at z, we get $\bar{H}_t(z,w;z_t)$, $\bar{H}_r(z,w;z)$, $\bar{V}_p(z,w)$, $\hat{V}_p(z,w)$, and pt(z) in Eqs.(49, 50).

For simulation of the nonlinear (and also linear) wave propagation we neglect the left side scattering terms in Eq. (14) that gives $$\nabla^2 p(\underline{r}, t) - \frac{1}{c_0^2(\underline{r})} \frac{\partial^2 p(\underline{r}, t)}{\partial t^2} + \frac{b_p(\underline{r})}{c_0^2(\underline{r})} \frac{\partial^2 p(\underline{r}, t)^2}{\partial t^2} - h_{ab}(\underline{r}, t) *_t \frac{1}{c_0^2} \frac{\partial^2 p(\underline{r}, t)}{\partial t^2} = 0 \quad (71)$$

For numerical simulations of the forward propagating pulse, we introduce retarded time t as $$t=t-z/c_0\ t=t+z/c_0\ p(z,\underline{r},t)fi\ \hat{p}(z,\underline{r},t) \quad (72)$$

The differentials of Eq.(71) take the following form in retarded time $$\frac{\partial p}{\partial t} = \frac{\partial \hat{p}}{\partial t} \frac{\partial t}{\partial t} = \frac{\partial \hat{p}}{\partial t} \quad (73)$$

$$\frac{\partial^2 p}{\partial t^2} = \frac{\partial^2 \hat{p}}{\partial t^2}$$

-continued $$\frac{\partial p}{\partial z} = \frac{\partial \hat{p}}{\partial z} - \frac{1}{c_0}\frac{\partial t}{\partial z}$$

$$\frac{\partial^2 p}{\partial z^2} = \frac{\partial^2 \hat{p}}{\partial z^2} - \frac{2}{c_0}\frac{\partial^2 \hat{p}}{\partial z \partial t} + \frac{1}{c_0^2}\frac{\partial^2 \hat{p}}{\partial t^2}$$

Changing to the retarded time variables then changes Eq. (71) to $$\frac{\partial^2 \hat{p}}{\partial z^2} - \frac{2}{c_0}\frac{\partial^2 \hat{p}}{\partial z \partial t} + \frac{2}{\wedge}\hat{p} + \frac{b_p(\underline{r})}{c_0^2(\underline{r})}\frac{\partial^2 \hat{p}^2}{\partial t^2} - \frac{1}{c_0^2}h_{ab}\tilde{*}_t \frac{\partial^2 \hat{p}}{\partial t^2} = 0 \quad (74)$$

For collimated beams we can neglect $\partial^2\hat{p}/\partial z^2$ referred to as the paraxial approximation, and introducing $\hat{p}=\hat{p}_L+\hat{p}_H$ as in Eq.(15), we can separate Eq.(74) into separate equations for the LF and HF bands, as a) $\frac{\partial^2 \hat{p}_L}{\partial z \partial t} = \frac{c_0}{2}\overset{2}{\wedge}\hat{p}_L - h_{ab}\tilde{*}_t\frac{1}{2c_0}\frac{\partial^2 \hat{p}_L}{\partial t^2} + \frac{b_p}{2c_0}\frac{\partial^2 \hat{p}_L^2}{\partial t^2}$ (75)

b) $\frac{\partial^2 \hat{p}_H}{\partial z \partial t} = \frac{c_0}{2}\overset{2}{\wedge}\hat{p}_H - h_{ab}\tilde{*}_t\frac{1}{2c_0}\frac{\partial^2 \hat{p}_H}{\partial t^2} + \frac{b_p}{c_0}\frac{\partial^2 \hat{p}_L\hat{p}_H}{\partial t^2} + \frac{b_p}{2c_0}\frac{\partial^2 \hat{p}_H^2}{\partial t^2}$ As discussed after Eq.(15) the propagation distance of the LF wave is generally so short ($\sim 30\ 1_{LF}$) that one can neglect the right hand nonlinear propagation term in Eq.(75a) and simulate the LF wave propagation in the linear scheme, which allows us to obtain the LF pulse along the co-propagating HF pulse, independent of the HF pulse as $$\hat{p}_L(z,\underline{r},t) = \hat{p}_L(z,\underline{r},0)\cos w_L(t+t_L(z,\underline{r})) \quad (76)$$

where $t_L(z,\underline{r})$ is the location of the center of the co-propagating HF pulse within the LF pulse. We define $$a(z,\underline{r}) = b_p(z,\underline{r})\hat{p}_L(z,\underline{r},0) \quad (77)$$

This allows us to write a self contained equation for the HF pulse from Eq.(75b) that takes into account both the nonlinear interaction distortion from the LF pulse and the nonlinear self distortion, as defined in Eq.(15), as $$\frac{\partial^2 \hat{p}_H}{\partial z \partial t} = \frac{c_0}{2}\overset{2}{\wedge}\hat{p}_H - h_{ab}\tilde{*}_t\frac{1}{2c_0}\frac{\partial^2 \hat{p}_H}{\partial t^2} + \frac{a}{c_0}\frac{\partial^2 \cos w_L(t+t_L(z,\underline{r}_\wedge))\hat{p}_H}{\partial t^2} + \frac{b_p}{2c_0}\frac{\partial^2 \hat{p}_H^2}{\partial t^2} \quad (78)$$

The first term on the right side represents diffraction, the $2^{nd}$ term absorption, the $3^{rd}$ term the nonlinear interaction distortion of the HF pulse by the LF pulse, and the last term the nonlinear self distortion of the HF pulse, Temporal Fourier transform of the LF-HF interaction term in Eq.(78) gives $$F_t\left\{\frac{a}{c_0}\frac{\partial^2 \cos w_L(t+t_L(z,\underline{r}_\wedge))\hat{p}_H}{\partial t^2}\right\} = \quad (79)$$

$$-\frac{aw^2}{2c_0}\left\{e^{iw_Lt_L(z,\underline{r}_\wedge)}\hat{p}_H(z,\underline{r}_\wedge,w-w_L) + e^{-iw_Lt_L(z,\underline{r}_\wedge)}\hat{p}_H(z,\underline{r}_\wedge,w+w_L)\right\}$$

Full temporal Fourier transform of Eq.(78) then takes the form $$\frac{d\hat{p}_H(z,\underline{r}_\wedge,w)}{dz} = -i\frac{c_0}{2w}\overset{2}{\wedge}\hat{p}_H(z,\underline{r}_\wedge,w) - \quad (80)$$

$$i\frac{w}{2c_0}H_{ab}(z,\underline{r}_\wedge,w)\hat{p}_H(z,\underline{r}_\wedge,w) + \frac{i}{2}\frac{w}{c_0}a(z,\underline{r}_\wedge)$$

$$\left\{e^{iw_Lt_L(z,\underline{r}_\wedge)}\hat{p}_H(z,\underline{r}_\wedge,w-w_L) + e^{-iw_Lt_L(z,\underline{r}_\wedge)}\hat{p}_H(z,\underline{r}_\wedge,w+w_L)\right\} + $$

$$\frac{i}{2}\frac{w}{c_0}\frac{a(z,\underline{r}_\wedge)}{\hat{p}_L(z,\underline{r}_\wedge,0)}\hat{p}_H(z,\underline{r}_\wedge,w)\tilde{*}_w\hat{p}_H(z,\underline{r}_\wedge,w)$$

where the last term represents convolution in the Fourier domain, introducing harmonic components of the fundamental HF band as $$\hat{p}_H(z,\underline{r}_\wedge,w)\tilde{*}_w\hat{p}_H(z,\underline{r}_\wedge,w) = \frac{1}{2p}\int dw\hat{p}_H(w-w)\hat{p}_H(w) \quad (81)$$

In the receiver one would typically band pass filter the received signal around the fundamental frequency. The last term hence represents a nonlinear absorption attenuation of the fundamental HF band by pumping energy into the harmonic and sub-harmonic components of the HF band.

Eq.(80) lends itself well for integration of the HF pressure pulse along the beam axis, z. We get overlap between the shifted spectra $\hat{p}_H(z,\underline{r},w-w_L)$ and $\hat{p}_H(z,\underline{r},w+w_L)$ when the bandwidth $B_H$ of the HF pulse and the angular frequency $w_L$ of the LF pulse have the following relation $$w_L < B/2 \quad T_{pH} = \frac{2p}{B} < \frac{2p}{2w_L} = T_L/2 \quad (82)$$

$T_{pH}$ is the pulse length of the HF pulse and $T_L$ is the period of the LF pulse,. In this case it makes sense to further modify Eq.(80) as $$\frac{d\hat{p}_H(z,\underline{r}_\wedge,w)}{dz} = \underbrace{-i\frac{c_0}{2w}\overset{2}{\wedge}\hat{p}_H(z,\underline{r}_\wedge,w)}_{\text{diffraction}} + \underbrace{\frac{w}{2c_0}H_{abi}(z,\underline{r}_\wedge,w)\hat{p}_H(z,\underline{r}_\wedge,w)}_{\text{absorption}} - \quad (83)$$

$$\underbrace{i\frac{w}{2c_0}H_{abr}(z,\underline{r}_\wedge,w)\hat{p}_H(z,\underline{r}_\wedge,w)}_{\text{dispersion}} + \underbrace{i\frac{w}{c_0}a(z,\underline{r}_\wedge)\cos w_Lt_L(z,\underline{r}_\wedge)\hat{p}_H(z,\underline{r}_\wedge,w)}_{\text{nonlinear propagation delay}} +$$

$$\underbrace{\frac{i}{2}\frac{w}{c_0}a(z,\underline{r}_\wedge)\cos w_Lt_L(z,\underline{r}_\wedge)\{\hat{p}_H(z,\underline{r}_\wedge,w-w_L) + \hat{p}_H(z,\underline{r}_\wedge,w+w_L) - 2\hat{p}_H(z,\underline{r}_\wedge,w)\}}_{\text{pulse form distirtion related to curvature of LF pressure oscialltion}} -$$

-continued $$\underbrace{\frac{1}{2}\frac{w}{c_0}a(z,\underline{r}_\wedge)\sin w_L t_L(z,\underline{r}_\wedge)\{\hat{p}_H(z,\underline{r}_\wedge,w-w_L) - \hat{p}_H(z,\underline{r}_\wedge,w+w_L)\}}_{\text{pulse form distirtion related to gradient of LF pressure oscialltion}} +$$

$$\underbrace{\frac{i}{2}\frac{w}{c_0}\frac{a(z,\underline{r}_\wedge)}{\hat{p}_L(z,\underline{r}_\wedge,0)}\hat{p}_H(z,\underline{r}_\wedge,w)\underset{w}{\sim}\hat{p}_H(z,\underline{r}_\wedge,w)}_{\text{HF pulse self distortion}}$$

where we have separated the absorption kernel $H_{ab}=H_{abr}+iH_{abi}$ into its imaginary component $H_{abi}$ that produces the absorption and its real component $H_{abr}$ that introduces a frequency dependent phase velocity, i.e. dispersion. $H_{abr}\neq 0$ because the absorption kernel $h_{ab}$ in Eq.(13) represents a causal physical process. When we measure the frequency dependent attenuation due to absorption, we measure only $H_{abi}(w)$ and $H_{abr}(w)$ can be obtained from the Hilbert transform as $$H_{abr}(w) = \frac{1}{p}Pr\int_{-\yen}^{\yen}dw\frac{H_{abi}(w)}{w-w} \tag{84}$$

The dispersion of the phase velocity given by $H_{abr}(w)$ produces a linear pulse form distortion that is independent of the LF pulse, but similar to the nonlinear pulse form distortion given by the last three terms in Eq.(83). We note that for $w_L t_L=0$ or p, the HF pulse is at the crest or trough of the LF oscillation. These are the HF pulses 103 and 106 in FIG. 1*a* where the LF pulse produces a nonlinear propagation delay given by the LF pressure at the peak of the HF pulse, and a pulse form distortion given by the curving of the LF oscillation along the HF pulse. In this situation we get $\cos w_L t_L=-1$ and $\sin w_L t_L=0$, which shows that the $3^{rd}$ term on the right side represents the nonlinear propagation delay of the center of the HF pulse due to the LF pulse as in Eq.(18), while the $4^{th}$ term represents pulse form distortion of the HF pulse due to the curvature of the LF pulse along the HF pulse which produces a nonlinear phase distortion.

Figure 1C:
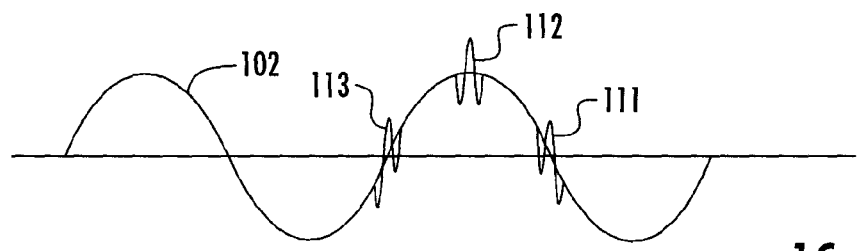

For $w_L t_L=-p/2$, the HF pulse is at the zero crossing of the LF pulse, shown as 111 and 113 in FIG. 1*c* where the LF pulse produces a nonlinear time compression/elongation of the HF pulse with no contribution to the nonlinear propagation delay. In this situation we have $\sin w_L t_L=-1$ and $\cos w_L t_L=0$, which shows that the $5^{th}$ term represents pulse form distortion of the HF pulse due to the gradient of the LF pulse around the center of the HF pulse which produces a spectral amplitude distortion. These effects are more clearly depicted if we divide Eq.(83) by $\hat{p}_H(z,\underline{r}_\text{-},w)$, neglecting the nonlinear self-distortion term $$\frac{d\hat{p}_H(z,\underline{r}_\wedge,w)}{\hat{p}_H(z,\underline{r}_\wedge,w)} = \left\{-i\frac{c_0}{2w}\frac{{}^2\hat{p}_H(z,\underline{r}_\wedge,w)}{\hat{p}_H(z,\underline{r}_\wedge,w)} + \frac{w}{2c_0}H_{abi}(z,\underline{r}_\wedge,w)\right\}dz - \tag{85}$$

$$i\frac{w}{2c_0}H_{abr}(z,\underline{r}_\wedge,w) + i\frac{w}{c_0}a(z,\underline{r}_\wedge)\cos w_L t_L(z,\underline{r}_\wedge)dz +$$

$$i\frac{w}{c_0}a(z,\underline{r}_\wedge)\cos w_L t_L(z,\underline{r}_\wedge)$$

$$\left\{\frac{\hat{p}_H(z,\underline{r}_\wedge,w-w_L) + \hat{p}_H(z,\underline{r}_\wedge,w+w_L)}{2\hat{p}_H(z,\underline{r}_\wedge,w)} - 1\right\}dz - i\frac{w}{c_0}a(z,\underline{r}_\wedge)$$

-continued $$\sin w_L t_L(z,\underline{r}_\wedge)\frac{\hat{p}_H(z,\underline{r}_\wedge,w-w_L) - \hat{p}_H(z,\underline{r}_\wedge,w+w_L)}{2\hat{p}_H(z,\underline{r}_\wedge,w)}dz$$

Integrating from depth point #(i-1) to #i, gives a recursive integral equation $$\hat{p}_H(z_i,\underline{r}_\wedge,w) = \hat{p}_H(z_{i-1},\underline{r}_\wedge,w)\exp \tag{86}$$

$$\left\{-i\frac{c_0}{2w}\int_{z_{i-1}}^{z_i}ds\frac{{}^2\hat{p}_H(s,\underline{r}_\wedge,w)}{\hat{p}_H(s,\underline{r}_\wedge,w)} + \frac{w}{2c_0}\int_{z_{i-1}}^{z_i}dsH_{abi}(s,\underline{r}_\wedge,w)\right\}\cdot\exp$$

$$\left\{-i\frac{w}{2c_0}\int_{z_{i-1}}^{z_i}dsH_{abr}(s,\underline{r}_\wedge,w) - iwd\ t(z_i,\underline{r}_\wedge)\right\}\cdot\exp$$

$$\left\{i\frac{w}{c_0}\int_{z_{i-1}}^{z_i}ds\ a(s,\underline{r}_\wedge)\cos w_L t_L(s,\underline{r}_\wedge)\right\}$$

$$\left(\frac{\hat{p}_H(s,\underline{r}_\wedge,w-w_L) + \hat{p}_H(s,\underline{r}_\wedge,w+w_L)}{2\hat{p}_H(s,\underline{r}_\wedge,w)} - 1\right)\right\}\cdot\exp$$

$$\left\{-\frac{w}{c_0}\int_{z_{i-1}}^{z_i}ds\ a(s,\underline{r}_\wedge)\sin w_L t_L(s,\underline{r}_\wedge)\right.$$

$$\left.\frac{\hat{p}_H(s,\underline{r}_\wedge,w-w_L) - \hat{p}_H(s,\underline{r}_\wedge,w+w_L)}{2\hat{p}_H(s,\underline{r}_\wedge,w)}\right\}$$

where the term with the nonlinear propagation delay is defined through $$d\ t(z_i,\underline{r}_\wedge) = -\frac{1}{c_0}\int_{z_{i-1}}^{z_i}ds\ a(s,\underline{r}_\wedge)\cos w_L t_L(s,\underline{r}_\wedge)$$

With this form of Eq.(83) we see that the $3^{rd}$ term clearly takes the form of a nonlinear propagation delay, while the $4^{th}$ and $5^{th}$ terms represent pulse form distortion.

We note that the inclusion of $\hat{p}_H(s,\underline{r}\text{-},wmw_L)$ in the two lowest terms is responsible for the pulse form distortion. $\hat{p}_H$ is fairly flat around the HF center frequency and as from Eq.(82) $w_L<B/2$, the major effect on the pulse form distortion is found at the edges of the HF pulse spectrum. One hence obtains some correction for the effect of pulse form distortion in the received HF signal by reducing the bandwidth of the received HF signal in a band pass filter.

B. Model Simulation Procedure

The strongest pulse reverberation noise is generated by reflections from fatty layers in muscular or parenchyma tissue. Typical acoustic parameters of such tissues are given in Table I. $b_n=1+B/2A$ is the bulk compressibility nonlinearity parameter, k is the bulk compressibility, $b_p=b_n*k$ is the non-linearity parameter used for simulations. r is the tissue mass density, $Z_0=rc$ is the characteristic acoustic impedance, and R is the reflection coefficient at planar interfaces between neighbor materials in the table.

TABLE I

Acoustic parameters for typical tissues.

| Tissue | $\beta_n$ | $\kappa\ 10^{-12}$ $Pa^{-1}$ | $\beta_p$ $10^{-9} Pa^{-1}$ | $\rho$ $kg/m^3$ | c m/s | $Z_0$ MRayl | R |
|---|---|---|---|---|---|---|---|
| Fat | 6 | 508 | 3.05 | 950 | 1440 | 1.37 | 0.1 |
| Muscle | 4.7 | 380 | 1.79 | 1070 | 1568 | 1.68 | −0.1 |
| Liver Parenchyma | 4.4 | 385 | 1.67 | 1050 | 1573 | 1.65 | 0.01 |

For the linear HF transmit beam and receive beams we carry through a simulation of Eq.(83) with a=0, where we use aperture boundary conditions as a) Transmit beam excitation: $\begin{cases} P_t(\underline{r}_0, w)e^{-iwt_t(\underline{r}_0,\underline{r}_t)} & \underline{r}_0, S_t \\ 0 & \text{else} \end{cases}$ (87)

b) Receive beam excitation: $\begin{cases} P_r(\underline{r}_0, w)e^{-iwt_r(\underline{r}_0,\underline{r}_r)} & \underline{r}_0, S_r \\ 0 & \text{else} \end{cases}$ where the variation of $P_t$ and $P_r$ with $\underline{r}_0$ opens for apodization of the HF transmit and receive apertures. These excitations at the transducer surface generates the pressure transmit fields $P_t(\underline{r}_1,w;\underline{r}_t)$ and $P_r(\underline{r}_1,w;\underline{r}_r)$ by Eq.(1) for the transmit and receive beams. The spatial frequency responses of the transmit and receive beams are then obtained from Eqs.(1,5) as a) Transmit beam: $ikH_t(\underline{r}_1, w; \underline{r}_t) = \dfrac{P_t(\underline{r}_1, w; \underline{r}_t)}{P_t(0, w)}$ (88)

b) Receive beam: $ikH_r(\underline{r}_1, w; \underline{r}_r) = \dfrac{P_r(\underline{r}_1, w; \underline{r}_r)}{P_r(0, w)}$ To simulate the effect of the nonlinear manipulation of the HF pulse by the LF pulse, we start by simulating the LF beam from Eq.(75a) in the linear regime, i.e. $b_p=0$, which for the temporal Fourier transform has the same structure as Eq.(83) with a=0. Since we only need the LF pressure within an LF period, we can carry through the simulation at the LF center frequency $w_L$ only. The simulation starts at z=0 with $P_L(\underline{r}_0,w_L)e^{-iw_L t_L(\underline{r}_0,\underline{r}_L)}$, where the variation of $P_L(\underline{r}_0,w_L)$ with $\underline{r}_0$ opens for apodization of the LF transmit aperture. The simulation gives $P_t(z,\underline{r}_\wedge,w_L;\underline{r}_L)$, from which one can derive $\hat{p}_L(z, \underline{r}_\wedge, 0) = |P_L(z, \underline{r}_\wedge, w_L; \underline{r}_L)|$ (89)

$t_L(z, \underline{r}_\wedge) = \dfrac{1}{w_L} - P_L(z, \underline{r}_\wedge, w_L; \underline{r}_L)$ This allows calculation of a(z,$\underline{r}$-) from Eq.(77) to simulate the HF transmit beam with nonlinear manipulation from Eq. (83) with a boundary condition at the transmit aperture of z=0 as in Eq.(87a). This gives $P_{tp}(\underline{r}_1,w;\underline{r}_t)$ of Eq.(19) and hence also $V_p(\underline{r},w;\underline{r}_t)$.

We are basing our estimation of the linear and nonlinear scattering on the total receive signal as a function of fast time. As we do not know the details of the 3D scatterer distribution, we assume that we have plane reflectors where the signal models are given in Section 5.6. We then calculate $\bar{H}_t(z,w;z_t), \bar{H}_r(z,w;z_r)$, and $\bar{V}_p(z,w)$ from Eq.(50). (90)

The linear phase of $\bar{V}_p$ gives the nonlinear propagation delay from the linear component of the phase as shown, while $\hat{V}_p$ represents nonlinear pulse form distortion, nonlinear self distortion attenuation, and spatial variation of the nonlinear propagation delay across the planes, as discussed in Section 5.7. For the plane reflectors we have $U(w)=H_{rt}(w)ikP_t(0,w)$, where $H_{rt}(w)$ is the receiver transducer transfer function as given after Eq.(3) [1].

We are now in position of estimation of the combined Class I and II pulse reverberation noise filters from the $1^{st}$ order HF receive signal with zero LF pulse. We first estimate the ultrasound reflection coefficient for strong plane reflectors. For zero LF pulse the $1^{st}$ order received signal is from Eq.(53)

$$y_{l1}(t) = \int_0^\Psi dt_1 R(t_1) u(t) \underset{t}{\sim} h_{tr}(t_1, t; t_t, t_r) \quad (91)$$

We apply a whitening filter so that $$u(t) \underset{t}{\sim} h_{tr}(t_1, t; t_t, t_r) \text{ fi approx } U_a(t) d(t - t_1) \quad (92)$$

This gives the estimate of the reflection coefficient $$\hat{R}(t) = \dfrac{y_w(t)}{U_a(t)} \quad (93)$$

where $y_w(t)$ is the whitened form of $y_{l1}(t)$. However, as the $y_{l1}(t)$ is a band-pass signal, the whitening will also give a band-pass signal, and we use the envelope of the estimate of the reflection coefficient $|\tilde{R}(t)|$ where $\tilde{R}(t)$ is the complex envelope of $\hat{R}(t)$. For the transducer as the $2^{nd}$ reflector we have $z_2=0$ and $R(z_2;w)=R_t(w)$. With a $1^{st}$ reflector at $z_1$ we will for a fast time t=2z/c get contributions from $3^{rd}$ reflectors within the interval ($z-z_1-Z_{pH}/2$, $z-z_1+Z_{pH}/2$) where $Z_{pH}$ is the HF pulse length. However, for our estimation of the noise correction delay and speckle correction it is adequate to take contribution from $z_3=z-z_1$ only. Writing z=ct/2, we get from Eq.(56) an estimate of the Class I and II noise in this case as $$N_a(w, z; p) = \hat{N}_a(w, z; p)e^{-iwpt_n(z)} \quad (94)$$

$N_a(w, z; p) =$ $$U(w)R_t(w)H_{tr}(z, w; \underline{r}_t, \underline{r}_r) \int_0^z dz_1 \tilde{R}_a(z_1, z) \bar{V}_p(z_1, w; \underline{r}_t)$$

$$\tilde{R}_a(z_1, z) = |R_a(z_1)| \int_{z-z_1-Z_{pH}/2}^{z-z_1+Z_{pH}/2} dz_3 |\tilde{R}(z_3)|$$

With zero LF pulse we have $V_p=V_0$ which is the attenuation due to self distortion of the HF pulse. We are from Eq.(94) now in position to estimate the noise delay correction and speckle correction filter for $3^{rd}$ order pulse reverberation noise where the transducer is the $2^{nd}$ reflector as $$M_a(w, z; p) = \dfrac{N_a(w, z; 0)}{N_a(w, z; p)} \dfrac{1}{1 + m_N |N_a(w, z; 0)/N_a(w, z; p)|^2} = \quad (95)$$

$$\hat{M}_a(w, z; p) e^{iwpt_n(z)}$$

-continued $$\frac{N_a(w, z; 0)}{N_a(w, z; p)} = \frac{\int_0^z dz_1 \tilde{R}_a(z_1, z)}{\int_0^z dz_1 \tilde{R}_a(z_1, z) \overline{V}_p(z_1, w; \underline{r}_t)}$$

where the correction delay $pt_n(z)$ is found from the linear phase component of $M_a(w,z;p)$. We note that $U(w)R_t(w)$ is shorted out in this expression, and can be neglected. With extra strong volume scatterers we should also include the pulse reverberation noise components with $z_2>0$ that takes the form $$N_b(w, z; p) = U(w)H_{tr}(z, w; \underline{r}_t, \underline{r}_r) \int_0^z dz_1 \tilde{R}_b(z_1, z) \overline{V}_p(z_1, w; \underline{r}_t) \quad (96)$$

$$\tilde{R}_b(z_1, z) = |\tilde{R}(z_1)| \int_0^{z_1} dz_2 |\tilde{R}(z_2)| \int_{z-(z_1-z_2)-Z_{pH}/2}^{z-(z_1-z_2)+Z_{pH}/2} dz_3 |\tilde{R}(z_3)|$$

The total $3^{rd}$ order scattered noise is then $$N(w, z; p) = AN_a(w, z; p) + N_b(w, z; p) = \overline{N}(w, z; p)e^{-iwpt_n(z)} \quad (97)$$

$$N(w, z; p) = U(w)H_{tr}(z, w; \underline{r}_t, \underline{r}_r)$$
$$\int_0^z dz_1 [AR_t(w)\tilde{R}_a(z_1, z) + \tilde{R}_b(z_1, z)] \overline{V}_p(z_1, w; \underline{r}_t)$$

The noise correction filter is then $$M(w, z; p) = \quad (98)$$
$$\frac{N(w, z; 0)}{N(w, z; p)} \frac{1}{1 + m_N |N(w, z; 0)/N(w, z; p)|^2} = \overline{M}(w, z; p)e^{iwpt_n(z)}$$

$$\frac{N(w, z; 0)}{N(w, z; p)} = \frac{\int_0^z dz_1 [AR_t(w)\tilde{R}_a(z_1, z) + \tilde{R}_b(z_1, z)]}{\int_0^z dz_1 [AR_t(w)\tilde{R}_a(z_1, z) + \tilde{R}_b(z_1, z)] \overline{V}_p(z_1, w; \underline{r}_t)}$$

where A is a parameter that we want to adjust to balance the $z_2=0$ reflection from the transducer surface with the $z_2>0$ reflection from fatty layers. We could use an a priori value of A when the magnitude of the reflection coefficient is well known, or we could adjust A for maximal suppression of the pulse reverberation noise. The expression for zero pressure $N_b(w,z;0)$ is found by setting $V_p=V_0$ in Eq.(96), and the noise filter takes the same form as in Eq.(97) substituting $N_a$ for N.

C. Estimation of Linear and Nonlinear Scattering with Noise Suppression

From the simulations in Sectiopn 5.8B, Eqs.(90) provides estimates of both the nonlinear propagation delay and the pulse form distortion, while Eqs.(95,98) provides estimates of the noise correction delay and noise speckle filter with the material parameters used in the simulation of the wave equations. These parameters can then be used in Eqs.(63-66) to provide estimates of the linear and nonlinear scattering signals with strong suppression of the combined Class I and II pulse reverberation noise, or in Eqs.(67,68) to provide estimates of only the linear scattering with suppression of the combined Class I and II pulse reverberation noise.

The simulations in Section 5.8B can be done with an a priori assessment of the acoustic material parameters as $c_0(z)$ and $b_p(z)$. An a priori assessment of $b_p(z)$ can be obtained from experience, but also from estimation of the nonlinear propagation delay t(z) as for example given in U.S. Pat. No. 8,038,616 or U.S. patent application Ser. No. 12/500,518. We then can estimate $b_p(z)$ by Eq.(18) as $$b_p(z) = -\frac{c_0}{\hat{p}_L(z, \underline{r}_\wedge, 0)\cos w_L t_L(z, \underline{r}_\wedge, 0)} \frac{\P t}{\P z} \quad (99)$$

Based on the signal estimates from this $1^{st}$ stage of estimation, one then obtains first estimates of the linear scattering signal $X_{li}(w)$ in Eqs.(66a) and (68) and nonlinear scattering signal $X_{ni}(w)$ in Eq.(66b).

For improved suppression one can then for example obtain an improved estimate of the nonlinear propagation delay t(z) by correlation techniques between two noise suppressed signals, for example $b_1$ and $b_2$ in Eq.(65). One can then by obtain an improved estimate of $b_p(z)$ using Eq.(99), and carry through the procedure again as described above.

The estimate of $b_p(z)$, and possibly also $c_0(z)$, can be further improved by adjustment in steps to minimize the total energy in for example the linear scattering signal $X_{li}(w)$ in Eqs.(66a) and (68) and nonlinear scattering signal $X_{ni}(w)$ in Eq.(66b) for maximal suppression of pulse reverberation noise, and also maximizing suppression of leak-through of the linear scattering component $X_{li}(w)$ in the estimate of the nonlinear scattering component $X_{ni}(w)$. The adjustment of the material parameters can be carried through manually, or automatically by optimizing a functional on the estimated linear and nonlinear scattering components, for example by minimizing the total energy in the linear scattering component $X_{li}(w)$ of Eq.(66a,68) or the nonlinear scattering component $X_{ni}(w)$ in Eq.(66b).

To improve the speed of the estimation, one can for example carry through the simulations of the wave pulses (Eq.(83)) for many values of the material parameters and transmitted amplitudes before measurements, and pre-store in an electronic memory the nonlinear propagation delay and pulse form distortion for these values, and in the estimation process simulations for defined parameters are retrieved from memory based on an address related to said defined parameters.

The storage requirements can be reduced by expressing the functional relationship of the nonlinear propagation delay and pulse form distortion to the material parameters and transmit amplitudes in series representations, and then pre-store in an electronic memory only the coefficients of said series representations. Said series representation can for example be of the Taylor series or Fourier series form in relation to the material parameters and transmitted amplitudes. Estimate values of the nonlinear propagation delay and pulse form distortion can then be obtained from such series representation for given values of the material parameters and transmit amplitudes.

By the comments following Eq.(86) we note that we can obtain some correction for the pulse form distortion by reduction of the bandwidth of the received HF signal through band pass filtering. This band pass filtering provides corrections of the effects of pulse form distortion both on the $1^{st}$ order and multiple order scattering signals.

5.9 Instrument

The methods according to the invention are conveniently implemented in an instrument where an example embodiment of such an instrument is shown in FIG. 9. The instrument sub-units are set up by a controller unit 901, that communicates with the sub-units via a controller bus 902. The controller takes input from a user via a user interface 903, that is composed of a keyboard, generally composed of control keys and alpha-numeric keys, a track-ball, a mouse, a touch-pad, or alike.

The pulse complexes are transmitted from a transmit radiation unit 904 that have different implementations for the different type of waves. For example, for EL waves the transmit unit typically comprises an EL transducer array, for EM waves the transmit unit typically comprises an EM antenna array in the sub-optical frequency range, while in the optical frequency range the transmit unit can comprise lenses and/or optical fibers, etc., all according to known methods. The transmit radiation unit is driven by a transmit drive unit 907 that generates the LF and HF pulses that composes the transmit pulse complex. For EL and EM waves at sub-optical frequencies, the transmit drive unit is typically implemented with transistors or electron tubes, while at optical frequencies the drive unit would typically comprises one or more lasers.

The transmit radiation unit 904 is often composed of different radiation components for the LF and HF pulses, due to bandwidth limitations in the LF and HF radiation components, where the Figure shows one radiation component 905 for transmission of the LF pulses, and one radiation component 906 for transmission of the HF pulses. The size of the LF and HF apertures are also generally different. However, if wide bandwidth radiation components are available, the same component can be used for transmission of both LF and HF pulses.

The scattered or transmitted HF pulses are picked by a similar HF radiation receive unit, where the Figure shows that the HF radiation receive unit is the same as the HF radiation transmit unit 906. However, the invention also covers the use of different radiation components for HF radiation transmit and receive. Different radiation components for HF transmit and receive can for example be found with an ultrasound ring array that encompasses the object, for example a female breast, to be imaged. With arrays one also generally selects a wider HF receive aperture than HF transmit aperture when the HF receive beam is dynamically focused.

The HF transmit beam necessarily has a fixed focus for each transmit, and in order to have adequate length of the transmit focus region, the HF transmit aperture is often chosen smaller than the HF receive aperture (higher F-number) that operates with dynamic focusing. However, to simplify combined suppression of Class I and II pulse reverberation noise, the invention devices to use close to similar HF transmit and receive beams. Multiple focal points for each image line can then for example be obtained through multiple transmit foci per image line, which allows for wider HF transmit apertures where the methods also have solutions with equal HF transmit and receive apertures and foci to simplify combined suppression of Class I and II pulse reverberation noise. With a given HF transmit and receive focus the instrument can provide synthetic HF receive and transmit focus for at least one more depth through transversal filtering of HF receive signals for many neighboring HF receive beams for said at least one more depth.

The instrument can also comprise means for transmission of pulse complexes with wide HF and LF beams in many directions towards the object, and storing HF receive element signals from each pulse complex transmit. The stored HF receive element signals for a set of transmitted pulse components are then processed to reconstruct HF receive signals in many image points where for each said image points the HF transmit and receive beams are selected close to equal, to simplify the combined suppression of Class I and II pulse reverberation noise.

When the same radiation component is used for HF transmit and receive, a transmit/receive switch 908 connects the HF radiation receive unit 906 to a receiver unit 909. The receiver unit amplifies and digitizes the individual array element signals that are used for further processing to generate measurement or image signals in image points. With synthetic HF transmit and receive beams, the individual HF receive element signals are stored in receiver unit 909 until the HF receive element signals for all transmit pulse complex components that are the basis for the image reconstruction, are received.

The HF receive element signals are then transferred to the HF receive beam former unit 910 that generates the HF receive signal for a focused HF receive beam for each image line. The receive beam former unit can for example generate a dynamically focused HF receive beam for each image line, or generate a HF receive beam with the same aperture and focus as the HF transmit beam, or present a synthetic reconstructed HF receive signal for image points with multi-component transmit pulse complexes.

The output of the beam former unit is then passed to a correction unit 911 that carries through one or both of a i) delay correction with correction delays and ii) a pulse speckle correction with speckle corrections, according to known methods or the methods described above, before a final processing in the processing unit 912, to form measurement or image signals with strong suppression of multiple scattering noise, for the linear and/or the nonlinear scattering components. The processing unit carries through further processing according to known methods to obtain measurement or image signals for display on the unit 913, for example related to the amplitude of the back scattered signal for imaging of structures, displacement or displacement strain or strain rate of the object for example obtained through Doppler phase comparison between RF signals, speckle tracking techniques, imaging of shear wave propagation, etc. according to known methods.

The output of the beam former unit is also taken into an estimation unit 914 that estimates at least one of said correction delays and pulse distortion corrections, according to known methods or the methods described above. The outputs of these estimations are transferred to the correction unit 911 to be applied in the pulse form and/or delay corrections of the HF receive signals in the correction unit.

Many of the components of the instrument are typically implemented as software components in the same computer, where typically after the signal digitization in unit 909 the digital signal would be transferred to a computer with multiple multi-core CPUs (Central Processing Units) and also GPUs (Graphic Processor Units). The simulation of the wave equation as part of the model based estimation scheme described above, would conveniently be implemented in one or more GPUs.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention.

It is also expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

Appendix A. Synthetic Dynamic Focus Through Transversal Filtering

The composite beam spatial frequency response is the product of the transmit and receive beam spatial frequency responses, i.e.

a) $H_b(z, \underline{r}_\wedge, w) = H_r(z, \underline{r}_\wedge, w) H_t(z, \underline{r}_\wedge, w)$ (A1)

b) $\tilde{H}_b(z, \underline{k}_\wedge, w) = \tilde{H}_r(z, \underline{k}_\wedge, w) \underset{\underline{k}_\wedge}{\tilde{*}} \tilde{H}_t(z, \underline{k}_\wedge, w)$ where the tilde indicates the Fourier transform that for the composite beam is obtained as a convolution of the transversal Fourier transforms for the transmit and receive beams. To develop an equation of propagation for the composite beam spatial frequency response, we calculate $$\nabla^2 H_b = \qquad (A2)$$
$$\nabla^2 (H_r H_t) = 2 \nabla H_r \nabla H_t + H_r \nabla^2 H_t + H_t \nabla^2 H_r = 2 \nabla H_r \nabla H_t - 2k_1^2 H_r H_t \Rightarrow$$
$$\nabla^2 H_b(\underline{r}, w) - 2k_1^2 H_b(\underline{r}, w) - 2 \nabla H_r(\underline{r}, w) \nabla H_t(\underline{r}, w) = 0$$

We note from Eq.(1) that in the homogeneous medium, i.e. $H_{abc}=1$, the spatial frequency responses of the transmit and receive beams take the form $$H_i(\underline{r}, w) = \int_{S_i} d^2 r_0 \frac{e^{-ik_1|\underline{r}-\underline{r}_0|-iwt(\underline{r}_0)}}{2p|\underline{r}-\underline{r}_0|} w(\underline{r}_0) \gg |H_i(\underline{r}, w)| e^{-ik_1 f(\underline{r})} \qquad (A3)$$
$$i = t, r$$

where $k_1 \underline{f}(\underline{r})$ is the phase front at $\underline{r}$. The phase represents the fastest spatial variation of $H_i(\underline{r},w)$ and the gradient can be approximated as [1]

$$\nabla H_i(\underline{r}, w) \gg -ik_1 \nabla f(\underline{r}) |H_i(\underline{r}, w)| e^{-ik_1 f(\underline{r})} \gg -ik_1 \underline{e}_{ni}(\underline{r}) H_i(\underline{r}, w) \qquad (A4)$$
$$i = t, r$$

where $\underline{e}_{ni}$ is the unit vector normal to the phase fronts. When the transmit and receive beams have close to the same phase fronts, i.e. $\underline{e}_{nt} = \underline{e}_{nr}$, Eq.(A2) gives a Helmholz propagation equation for the composite beam spatial frequency response as $$\nabla^2 H_b(\underline{r}, w) - 4k_1^2 H_b(\underline{r}, w) = 0 \qquad (A5)$$

We get $(2k_1)^2$ as the propagation factor for the composite beam due to the double propagation distance $2r$ from the transducer to the scatterer and back to the transducer again. The Fourier transform across the transversal plane gives $$\frac{\partial^2 \tilde{H}_b(z, \underline{k}_\wedge, w)}{\partial z^2} + (4k_1^2 - k_\wedge^2) \tilde{H}_b(z, \underline{k}_\wedge, w) = 0 \qquad (A6)$$

with the solution for forward propagating waves as $$\tilde{H}_b(z, \underline{k}_\wedge, w) = \qquad (A7)$$
$$\tilde{H}_b(0, \underline{k}_\wedge, w) e^{-i2k_1 z \sqrt{1-k_\wedge^2/4k_1^2}} = \tilde{H}_b(z_t, \underline{k}_\wedge, w) e^{-i2k_1(z-z_1)\sqrt{1-k_\wedge^2/4k_1^2}}$$

For a common focal depth $z_r = z_t$ for the transmit and the receive beam, the composite field in the focus is from Eq.(A1)

$$H_b(z_t, \underline{r}_\wedge, w) = \qquad (A8)$$
$$H_r(z_t, \underline{r}_\wedge, w) H_t(z_t, \underline{r}_\wedge, w) = \frac{e^{-i2k_1 z_t}}{(2pz_t)^2} \int_{S_r} dx_0 dy_0 w_r(x_0, y_0)$$
$$e^{ik_1(xx_0+yy_0)/z_t} \int_{S_t} dx_0 dy_0 w_t(x_0, y_0) e^{ik_1(xx_0+yy_0)/z_t}$$

The composite focal field is hence the product of two Fourier transforms for the transmit and receive apertures across the transversal plane. This implies that the focal field is the Fourier transform of the convolution of the transmit and receive apertures, and the transversal Fourier transform of the composite beam spatial frequency response is hence $$\tilde{H}_b(z_t, \underline{k}_\wedge, w) = e^{-i2k_1 z_t} \left(\frac{l^2 z_t}{2p}\right)^2 w_r(k_\wedge z_t/k_1) \underset{\underline{r}_\wedge}{\tilde{*}} w_t(k_\wedge z_t/k_1) \qquad (A9)$$

We hence see that this expression complies with the general theorem that the transversal width of the beam is lowest when the transversal phase is zero. To move the focus of the composite beam from a depth $z_t$ to $z_f$ can be achieved by the transversal filtering as $$\tilde{H}_b(z, \underline{k}_\wedge, w; z_f) = \tilde{H}_b(z, \underline{k}_\wedge, w; z_t) e^{i2k_1(z_f - z_t)\sqrt{1-k_\wedge^2/4k_1^2}} \qquad (A10)$$

Eqs.(A9,10) are based on a common focus for the transmit and receive beams. If there are different apertures of the transmit and receive beams, we can still have $\underline{e}_{nt} \approx \underline{e}_{nr}$ within the narrowest of the beams. Eqs.(A5-10) are still valid, but the achievable focus is determined by the narrowest aperture. We are however interested in the filtered synthetic focusing to obtain dynamic focusing with Q=1 as defined in Eqs.(29,40), i.e. $H_t = H_r$, which requires $w_t(\underline{r}) = w_r(\underline{r})$, i.e. also $S_r = S_t$.

Another interesting situation is that we have a fixed focus transmit beam and a dynamic focus receive beam. The transversal convolution in Eq.(A10b) will then give a phase filter that can be used to obtain a synthetic depth focusing of the transmit beam also.

Appendix B. Plane Reflectors

B1. 1$^{st}$ Order Scattering

We can now apply this result to the transversal integration across the plane at $\underline{z}$ in the expression for the 1$^{st}$ order scattered signal from the plane at $\underline{z}$ in Eq.(48). For a linear material we have $V_p = 1$ and the transversal integral takes the form $$\int_{R^2} d^2 r_\wedge ik H_r(z, r_\wedge, w; r_r) ik H_t(z, r_\wedge, w; r_t) = \int_{R^2} d^2 r_\wedge \quad (B1)$$
$$\int_{S_r} d^2 r_\wedge w_r(r_4) H_{abc}(r_4, w; r_r) e^{-iwt_r(r_4, r_r)} ik 2G(z + r_\wedge, r_4, w) \cdot$$
$$\int_{S_t} d^2 r_0 w_t(r_0) H_{abc}(r_0, w; r_t) e^{-iwt_t(r_0, r_t)} ik 2G(z + r_\wedge, r_0, w)$$

We note that $G(r_a, r_b, w) = G(r_b, r_a, w)$ (B2)

$$\int_{R^2} d^2 r_\wedge ik 2G(z + r_\wedge, r_4, w) ik 2G(z + r_\wedge, r_0, w) =$$
$$\int_{R^2} d^2 r_\wedge ik 2G(r_4, z + r_\wedge, w) ik 2G(r_\wedge + z, r_0, w) =$$
$$ik 2G(2z + r_4, r_0, w)$$

which inserted into (B3) gives = (B3)

$$\int_{S_r} d^2 r_4 w_r(r_4) H_{abc}(r_4, w; r_r) e^{-iwt_r(r_4, r_r)} \cdot \int_{S_t} d^2 r_0 w_t(r_0)$$
$$H_{abc}(r_0, w; r_t) e^{-iwt_t(r_0, r_t)} ik 2G(2z + r_4, r_0, w)$$

and finally $$\int_{R^2} d^2 r_\wedge ik H_r(z, r_\wedge, w; r_r) ik H_t(z, r_\wedge, w; r_t) = H_{tr}(z, w; r_t, r_r) = \quad (B4)$$
$$\int_{S_r} d^2 r_4 w_r(r_4) H_{abc}(r_4, w; r_r) e^{-iwt_r(r_4, r_r)} ik H_t(2z + r_4, w; r_t)$$

For linear materials the $1^{st}$ order reflected field is obtained through a combination of Eqs.(B1,4) as $$dY_{l0}(w;z) = dz R(z) U(w) H_{tr}(z, w; r_r, r_r) \quad (B5)$$

B2. $3^{rd}$ Order Scattering

For a fully linear material we have $V_p = 1$ and the transversal integral in Eq.(49) takes the form $$\int_{R^2} d^2 r_\wedge j ik H_r(2z - z_j, r_{\wedge j}, w; r_r) ik H_t(z_j, r_{\wedge j}, w; r_t) = \quad (B6)$$
$$\int_{R^2} d^2 r_\wedge \int_{S_r} d^2 r_4 w_r(r_4) H_{abc}(r_4, w; r_r) e^{-iwt_r(r_4, r_r)}$$
$$ik 2G(2z - z_j + r_{\wedge j}, r_4, w) \cdot \int_{S_t} d^2 r_0 w_t(r_0)$$
$$H_{abc}(r_0, w; r_t) e^{-iwt_t(r_0, r_t)} ik 2G(z_j + r_{\wedge j}, r_0, w)$$

We notice that integration over the transversal coordinate represents a mirroring of the point source for one of the Green's functions, which gives $$\int_{R^2} d^2 r_\wedge j ik 2G(2z - z_j + r_{\wedge j}, r_4, w) ik 2G(z_j + r_{\wedge j}, r_0, w) = \quad (B7)$$
$$\int_{R^2} d^2 r_\wedge ik 2G(r_4, 2z - z_j + r_{\wedge j}, w) ik 2G(z_j + r_{\wedge j}, r_0, w) =$$
$$ik 2G(2z + r_4, r_0, w)$$

and (B6) takes the form $= \int_{S_r} d^2 r_4 w_r(r_4) H_{abc}(r_4, w; r_r) e^{-iwt_r(r_4, r_r)} \cdot$
$$\int_{S_t} d^2 r_0 w_t(r_0) H_{abc}(r_0, w; r_t) e^{-iwt_t(r_0, r_t)} ik 2G(2z + r_4, r_0, w)$$

which is modified to $$\int_{R^2} d^2 r_{\wedge j} ik H_r(2z - z_j, r_{\wedge j}, w; r_r) ik H_t(z_j, r_{\wedge j}, w; r_t) = \quad (B8)$$
$$H_{tr}(z, w; r_t, r_r) =$$
$$\int_{S_r} d^2 r_4 w_r(r_4) H_{abc}(r_4, w; r_r) e^{-iwt_r(r_4, r_r)} ik H_t(2z + r_4, w; r_t)$$

For the linear material, Eq.(54) then takes the form $$dY_{Ip}(w;z,z_1,z_2) = dz_1 dz_2 R(z_1) R(z_2;w) R(z-(z_1-z_2)) U(w)$$
$$H_{tr}(z, w; r_r, r_r) a)$$

$$dY_{IIp}(w;z,z_2,z_3) = dz_2 dz_3 R(z-(z_3-z_2)) R(z_2;w) R(z_3) U(w)$$
$$H_{tr}(z, w; r_r, r_r) b) \quad (B9)$$

As $z_3 = z - (z_1 - z_2)$ and $z - (z_3 - z_2)$ we see that for the linear material the Class I and Class II pulse reverberation noise is equal.

REFERENCES

[1] Bjorn A. J. Angelsen, "Ultrasound Imaging—Waves, Signals, and Signal Processing", Emantec, Trondheim, December 2001. http://www.ultrasoundbook.com
[2] Bjorn A. J. Angelsen and Rune Hansen, "Surf Imaging—a New Method for Ultrasound Contrast Agent Imaging", IEEE Ultrasonics Symp 2007, New York N.Y.
[3] Bjorn A. J. Angelsen and Thor Andreas Tangen, "Method for imaging of nonlinear interaction scattering" United Kingdom Patent Application No. 1018933.0

We claim:

1. A method for measurement or imaging of a region of an object with waves where object material parameters for wave propagation and scattering are modified by the wave field strength, comprising:
   a) transmitting at least two pulse wave complexes towards said region, each of said pulse complexes comprising
      a low frequency (LF) pulse with frequencies in an LF band transmitted from an LF array aperture with LF array elements, and
      a high frequency (HF) pulse with frequencies in an HF band transmitted from an HF array aperture with HF array elements, where
      the pulse length of the transmitted HF pulse is less than half an oscillation period of the transmitted LF pulse, and where
      the transmitted HF pulse propagates spatially so close to the transmitted LF pulse that the HF pulse observes a manipulation of the object material parameters by the co-propagating LF pulse at least for a part of a propagation depth of the HF pulse, and where
      at least the transmitted LF pulse varies for each transmitted pulse complex to produce different manipulations of the object, where the transmitted LF pulse for at least one pulse complex can be zero, and the transmitted LF pulse for at least one pulse complex is non-zero, and
   b) picking up for each transmitted pulse complex HF receive element signals from one or both of scattered and transmitted HF components from the transmitted pulse complexes using HF receive array elements, where the HF receive element signals are combined into a HF receive signal with a HF receive aperture and HF receive focus, and c) correcting said HF receive signals at a fast time interval by
  i) delay corrections with average correction delays in a fast time where said average correction delays are obtained as a weighted average of an estimate of the nonlinear propagation delay at a $1^{st}$ reflection for the each multiple scattered HF pulses that are found in the composite multiple scattered HF receive noise signal in said fast time interval, where said weighting is obtained from the received HF signal as a function of depth, and selectably in addition also
  ii) speckle corrections in the fast time that compensates for the LF pressure variations of the speckle of the composite multiple scattered HF receive noise signal in said fast time interval,
  where one or both of said delay corrections and speckle corrections can be zero for at least one HF receive signal, to form corrected HF signals for said fast time interval, and
d) combining said corrected HF signals from at least two transmitted pulse complexes to form at least one noise suppressed HF signal with suppression of pulse reverberation noise.

2. A method according to claim 1, wherein
steps a) and b) includes transmitting at least 3 pulse complexes with different LF pulses towards the object producing at least 3 HF receive signals, and wherein steps c) and d) includes,
correcting and combining the HF receive signals to form at least two noise suppressed HF signals, and
said at least two noise suppressed HF signals are further corrected by at least one of
  i) delay corrections using correction delays in a fast time, and
  ii) speckle corrections using speckle corrections in the fast time,
to form at least two corrected noise suppressed HF signals, and
combining said at least two corrected noise suppressed HF signals to form at least one nonlinear scattering HF signal with linear scattering components and pulse reverberation noise substantially suppressed.

3. A method according to claim 2, where said speckle corrections are done with a filter in the fast time.

4. A method according to claim 2, where at least one of said correction delays and said speckle corrections are estimated in a process that uses a mathematical model of LF pulse generated variations in at least one of i) HF receive signal delays, and ii) speckle of the multiple scattered noise signal components in the HF receive signals.

5. A method according to claim 1, where said speckle corrections are done with a filter in the fast time.

6. A method according to claim 5, where said filter is a bandpass filter that reduces the bandwidth of the signals.

7. A method according to claim 1, where the HF transmit and receive beams are matched so that Class I and Class II $3^{rd}$ order scattering noise for zero LF pulse is close to equal.

8. A method according to claim 1, where in addition
multiple transmit beams with matched HF receive beams are transmitted in different beam directions to form HF receive signals for said different beam directions, and one of
  i) processing of the HF receive signals according to point c) and d) of claim 1 to form noise suppressed HF receive signals for said different beam directions, followed by transversal filtering of the noise suppressed HF receive signals for said different beam directions for a set of depths to obtain synthetic noise suppressed HF receive signals with synthetic HF image beam foci for said set of depths, and
  ii) transversal filtering of the HF receive signals from said different beam directions for a set of depths to obtain synthetic HF receive signals with synthetic HF image beam foci for said set of depths, followed by processing of the synthetic HF receive signals according to point c) and d) of claim 1 to form synthetic noise suppressed HF receive signals with synthetic HF image beam foci for said set of depths.

9. A method according to claim 7, comprising the image of more than one depth region where each depth region is imaged with different HF receive signals from different transmitted pulse complexes with HF transmit and receive beam focus selected within said each depth region.

10. A method according to claim 1, comprising
a) transmitting more than one pulse complex with different directions towards the object, and
b) receiving and storing HF receive array element signals for each HF receive array element and each transmitted pulse complex, and
c) combining said HF receive array element signals from said transmitted pulse complexes for a group of image points to provide synthetic HF receive signals with synthetic HF transmit and receive beams for each image point, said synthetic HF transmit and receive beams are constructed so that a difference between Class I and Class II $3^{rd}$ order scattered noise-signals in said synthetic HF receive signals is substantially minimized in each image point for pulse complexes with zero LF pulse.

11. A method according to claim 10, where each said more than one transmitted pulse complex have wave fronts that are substantially plane in at least one direction.

12. A method according to claim 1, where at least one of said correction delays and said speckle corrections are estimated in a process that uses a mathematical model of LF pulse generated variations in at least one of i) HF receive signal delays, and ii) speckle of the multiple scattered noise signal components in the HF receive signals.

13. A method according to claim 12, said process comprising
a) obtaining the nonlinear propagation delay and pulse form distortion for the forward propagating HF pulse at multiple depths through simulation of a nonlinear wave equation for the forward propagating HF pulse with the actual transmitted LF/HF pulse complex and defined object material parameters, and
b) obtaining from the measured HF receive signal, parameters relating to relative reflection coefficients as a function of depth along the beam, and
c) estimating said correction delays and speckle corrections in processes that include combining one or both of said nonlinear propagation delays and pulse form distortions for the HF pulse obtained under point a) with said parameters relating to relative reflection coefficients as a function of depth obtained under point b) in a mathematical model for multiple scattered HF noise signals.

14. A method according to claim 13, where the process is carried through in steps where each step applies the method according to claim 13, and for each step said defined object material parameters are adjusted to increase the suppression of one or both of i) pulse reverberation noise and ii) $1^{st}$ order linear scattering components in the processed HF receive signal, where said adjustment is carried through as one or both of
    a) manual adjustment based on observation of a displayed image, and
    b) automatic adjustment to optimize a functional on a processed HF receive signal in a region of an image.

15. A method according to claim 14, where said functional is the total power of a processed HF receive signal in a region of an image.

16. A method according to claim 14, where the simulation of a nonlinear wave equation for the forward propagating HF pulse with an actual transmitted LF/HF pulse complex and defined object material parameters is carried through for a set of multiple defined parameters before the measurements and pre-stored in an electronic memory, and in the estimation process the simulation for defined object material parameters is retrieved from memory based on a memory address related to said defined parameters.

17. A method according to claim 13, where for point a) coefficients of series expansions of the nonlinear propagation delay and pulse form distortions dependency on the LF pulse and defined object material parameters are calculated and stored, so that for a given transmitted LF pulse and defined object material parameters, estimates of the nonlinear propagation delays and pulse form distortions can be calculated by said series expansions utilizing said stored coefficients of the series expansions.

18. A method according to claim 17, where said series expansions are one or both of Taylor series and Fourier series expansions.

19. A method according to claim 1, where the LF and HF transmit apertures are defined so that the nonlinear propagation delay $\tau(t)$ for the transmitted HF pulse has a substantially linear variation with the fast time t, and for suppression of pulse reverberation noise said correction delays are approximated by $\tau(t)/2$.

20. A method according to claim 1, where for suppression of pulse reverberation noise in echo weak regions, the same HF receive signal obtained with a non-zero LF pulse is delay corrected with two different correction delays to provide two corrected HF signals, and said two corrected HF signals are combined to provide a noise suppressed HF signal.

21. A method according to claim 1, where transmitting LF array elements are selected so that said LF array aperture has a region around the center with no transmission of the LF pulse, so that manipulation of the object material parameters by the LF pulse observed by the co-propagating HF pulse is very low in a near field region of the HF array aperture.

22. A method according to claim 1, where said noise suppressed HF signals are used in the process of estimating corrections for wave front aberrations in materials with spatial variations in the wave propagation velocity.

23. A method according to claim 1, where in addition multiple transmit beams with matched HF receive beams are transmitted in different beam directions to form HF receive signals for said different beam directions, further including transversal filtering of one of
    i) the HF receive signals from said different beam directions for a set of depths to obtain synthetic HF receive signals with synthetic HF image beam foci for said set of depths, where said set of synthetic HF receive signals is further processed according to c) and d) of claim 1 and
    ii) the noise suppressed HF receive signals for said different beam directions for a set of depths to obtain synthetic noise suppressed HF receive signals with synthetic HF image beam foci for said set of depths.

24. An instrument for measurement or imaging of a region of an object with waves where the object material parameters for wave propagation and scattering are modified by the wave field strength, comprising:
    a) transmit means comprising
        a selectable low frequency (LF) transmit array aperture with LF array elements and a selectable LF transmit focus and LF transmit beam direction, and
        a selectable high frequency (HF) transmit array aperture with HF array elements and a selectable HF transmit focus and HF transmit beam direction, that are used for
    transmitting at least two pulse wave complexes towards said region, each of said pulse complexes being composed of an LF pulse with frequencies in an LF band, and an HF pulse with frequencies in an HF band, where
    the transmitted HF pulse propagates spatially so close to the transmitted LF pulse that the HF pulse observes a manipulation of the object material parameters by the co-propagating LF pulse at least for a part of a propagation depth of the HF pulse, and
    at least the transmitted LF pulse varies for each transmitted pulse complex to produce different manipulations of the object, where the transmitted LF pulse for at least one pulse complex can be zero, and the transmitted LF pulse for at least one pulse complex is non-zero, and
    b) HF receive and receive and HF beam forming means comprising HF receive array elements that for each transmitted pulse complex picks up HF receive element signals from one or both of scattered and transmitted HF components from the transmitted pulse complexes, where the beam forming means combines said HF receive element signals into HF receive signals with a HF receive aperture and a HF receive focus, and
    c) correction means for correcting said HF receive signals by
        i) delay corrections with average correction delays in a fast time where said average correction delays are obtained as a weighted average of an estimate of the nonlinear propagation delay at the $1^{st}$ reflection for the each multiple scattered HF pulses that are found in the composite multiple scattered HF receive noise signal in said fast time interval, where said weighting is obtained from the received HF signal as a function of depth, and selectably in addition also
        ii) speckle corrections in the fast time that compensates-for the LF pressure variations of the speckle of the composite multiple scattered HF receive noise signal in said fast time interval,
    where one or both of said delay corrections and speckle corrections can be zero for at least one HF receive signal, to form corrected HF signals for said fast time interval, and
    d) processing means for further combining said corrected HF signals to form at least one noise suppressed HF signal with suppression of pulse reverberation noise.

25. An instrument according to claim 24, where said transmit means comprises means for transmitting at least 3 pulse complexes with different LF pulses towards the object, and wherein step c) includes means for
    a) correcting and combining the HF receive signals according to claim 21 to form at least two noise suppressed HF signals, and b) means for further processing of said at least two noise suppressed HF signals including at least one of
   i) delay corrections using correction delays in a fast time (depth-time), and
   ii) speckle corrections in the fast time,
to form at least two corrected noise suppressed HF signals, and
c) means for combining said corrected noise suppressed HF signals to suppress linear scattering components to form nonlinear measurement or imaging HF signals.

26. An instrument according to claim 25, including means for speckle corrections in the form of a filter in the fast time.

27. An instrument according to claim 25, comprising estimation means for estimation of at least one of said correction delays and speckle corrections.

28. An instrument according to claim 24, including means for speckle corrections in the form of a filter in the fast time.

29. An instrument according to claim 28, where said filter in the fast time is a bandpass filter that reduces the bandwidth of the signals.

30. An instrument according to claim 24, where said HF transmit, HF receive and HF beam forming means comprise means for matching HF transmit and receive beams so that Class I and Class II $3^{rd}$ order scattering noise for zero LF pulse is close to equal.

31. An instrument according to claim 24, where said transmit, HF receive and HF beam forming means comprise
   means for transmitting multiple pulse complexes with different transmit beam directions with matched HF receive beams to form HF receive signals in said different directions, and one of
   i) means for processing of the HF receive signals according to point c) and d) of claim 1 to form noise suppressed HF receive signals for said different beam directions, followed by
      means for transversal filtering of the noise suppressed HF receive signals for said different beam directions for a set of depths to obtain synthetic noise suppressed HF receive signals with synthetic HF image beam foci for said set of depths, and
   ii) means for transversal filtering of the HF receive signals from said different beam directions for a set of depths to obtain synthetic HF receive signals with synthetic HF image beam foci for said set of depths, followed by
      means for processing of the synthetic HF receive signals according to point c) and d) of claim 1 to form synthetic noise suppressed HF receive signals with synthetic HF image beam foci for said set of depths.

32. An instrument according to claim 24, where
a) said transmit means allows transmitting more than one pulse complex with different directions towards said object, and
b) said HF receive means comprises means for receiving and storing HF receive array element signals for each HF receive array element and each transmitted pulse complex, and
c) said HF beam forming means comprises means for combining said HF receive array element signals from said transmitted pulse complexes for a group of image points to provide synthetic HF receive signals with synthetic HF transmit and receive beams for each image point, said synthetic HF transmit and receive beams are constructed so that a difference between Class I and Class II $3^{rd}$ order scattered noise signals in said synthetic HF receive signals is substantially minimized in each image point of said group of image points for pulse complexes with zero LF pulses.

33. An instrument according to claim 32, where said transmit means allows transmit of LF and HF pulse waves with wave fronts that are substantially plane in at least one direction.

34. An instrument according to claim 24, comprising estimation means for estimation of at least one of said correction delays and speckle corrections.

35. An instrument according to claim 34, where said estimation means uses a mathematical model of LF pulse generated variations in at least one of i) HF receive signal delays, and ii)) speckle of the multiple scattered noise signal components in the HF receive signals.

36. An instrument according to claim 35, where said estimation means comprises
a) means for simulation of a nonlinear wave equation for the forward propagating HF pulse with an actual transmitted LF/HF pulse complex with defined object material parameters, and obtaining the nonlinear propagation delay and pulse form distortion for the simulated HF pulsed wave, and
b) means for obtaining from the measured HF receive signal, parameters relating to relative reflection coefficients as a function of depth along the beam, and
c) means for estimation of said correction delays and speckle corrections in a process that includes combining one or both of said nonlinear propagation delays and pulse form distortions for the simulated HF pulsed wave obtained under point a) with said parameters relating to relative reflection coefficients as a function of depth obtained under point b) in a mathematical model for multiple scattered HF noise signals.

37. An instrument according to claim 36, where said estimation means comprises means for adjusting said defined object material parameters to increase the suppression of one or both of i) pulse reverberation noise and ii) $1^{st}$ order linear scattering components in the processed HF receive signal, where said adjusting is carried through as one or both of
   i) manual adjusting based on observation of the displayed image, and
   ii) automatic adjusting to optimize a functional HF receive signal in a region of an image.

38. An instrument according to claim 36, where said means for simulation of a nonlinear wave equation for the forward propagating HF pulse with an actual transmitted LF/HF pulse complex with defined object material parameters, comprises means for storage of a set of simulations with different defined object material parameters where said set of simulations are carried through before the measurements, and in the estimation process the simulation for defined object material parameters is retrieved from memory based on a memory address related to said defined parameters.

39. An instrument according to claim 36, where said means for simulation comprises means for calculation and storage of coefficients of series expansions of the nonlinear propagation delay and pulse form distortions dependency on the LF pulse and defined object material parameters, so that for a given transmitted LF pulse and defined object material parameters, estimates of the nonlinear propagation delays and pulse form distortions can be calculated by said series expansions utilizing said stored coefficients of the series expansions.

40. An instrument according to claim 24, where said transmit means allow the LF and HF transmit apertures to be defined so that the nonlinear propagation delay $\tau(t)$ for the transmitted HF pulse has a substantially linear variation with the fast time t, so that for suppression of pulse reverberation noise at fast time t, said correction delays can be approximated by $\tau(t)/2$.

41. An instrument according to claim 24, where said correction means delay corrects the same HF receive signal obtained with a non-zero LF pulse with two different correction delays to provide two corrected HF signals, and said two corrected HF signals are combined to provide a noise suppressed HF signal.

42. An instrument according to claim 24, including means for selecting the transmitting LF array aperture to obtain an LF array aperture that has a region around the centre with no transmission of the LF pulse, so that manipulation of the object material parameters by the LF pulse observed by the co-propagating HF pulse is very low in a near field region of the HF array aperture.

43. An instrument according to claim 24, including
means for estimation of corrections for wave front aberrations in materials with spatial variations in the wave propagation velocity, and
means for corrections of the HF receive element signals for wave front aberrations.

44. An instrument according to claim 24, where said transmit, HF receive and HF beam forming means comprise
means for transmitting multiple pulse complexes with different transmit beam directions with matched HF receive beams to form HF receive signals in said different directions, and further including means for transversal filtering of one of
i) the HF receive signals from said different beam directions for a set of depths to obtain synthetic HF receive signals with synthetic HF image beam foci for said set of depths, where said set of synthetic HF receive signals is further processed according to c) and d) of claim 1 and
ii the noise suppressed HF receive signals for said different beam directions for a set of depths to obtain synthetic noise suppressed HF receive signals with synthetic HF image beam foci for said set of depths.

* * * * *